(12) United States Patent (10) Patent No.: US 8,243,130 B2
Kawano (45) Date of Patent: Aug. 14, 2012

(54) CAPSULE MEDICAL DEVICE GUIDANCE SYSTEM

(75) Inventor: Hironao Kawano, Machida (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/053,768

(22) Filed: Mar. 22, 2011

(65) Prior Publication Data

US 2011/0292196 A1 Dec. 1, 2011

Related U.S. Application Data

(63) Continuation of application No. PCT/JP2010/063218, filed on Aug. 4, 2010.

(30) Foreign Application Priority Data

Nov. 9, 2009 (JP) ................................. 2009-256326

(51) Int. Cl.
*A61B 1/04* (2006.01)

(52) U.S. Cl. ....................................................... 348/74

(58) Field of Classification Search .................... 348/74, 348/77; A61B 1/04
See application file for complete search history.

(56) References Cited

U.S. PATENT DOCUMENTS

| | | | |
|---|---|---|---|
| 2006/0063974 | A1 | 3/2006 | Uchiyama et al. |
| 2008/0294006 | A1 | 11/2008 | Uchiyama et al. |
| 2009/0299142 | A1 | 12/2009 | Uchiyama et al. |

FOREIGN PATENT DOCUMENTS

| | | |
|---|---|---|
| JP | 2004-298560 | 10/2004 |
| JP | 2008-168144 | 7/2008 |
| JP | 2008-178693 | 8/2008 |
| JP | 2010-17553 | 1/2010 |
| WO | WO 2006/033306 A1 | 3/2006 |
| WO | WO 2007/074888 A1 | 7/2007 |
| WO | WO 2007/077922 A1 | 7/2007 |
| WO | WO 2008/099851 A1 | 8/2008 |

OTHER PUBLICATIONS

Japanese Office Action dated Jan. 11, 2011.
Abstract of European Patent Publication No. EP 2 143 370 A1, dated Jan. 13, 2010.

*Primary Examiner* — Young Lee
(74) *Attorney, Agent, or Firm* — Scully, Scott, Murphy & Presser, P.C.

(57) ABSTRACT

A capsule medical device guidance system including a magnetic field generator that generates either a trapping magnetic field that attracts a magnetic field response unit at any position on a horizontal plane and traps a capsule medical device or a gradient magnetic field that has a substantially uniform magnetic field gradient and forces the magnetic field response unit. When the control unit switches the magnetic field from the trapping magnetic field to the gradient magnetic field, a control unit causes a storage unit to store a generation position on the horizontal plane, and when the control unit switches a magnetic field from the gradient magnetic field to the trapping magnetic field, the control unit causes the magnetic field generator to generate the trapping magnetic field at the position stored in the storage unit.

4 Claims, 32 Drawing Sheets

2: Magnetic Field Generator
10: Capsule Endoscope

10: Capsule Endoscope
11A-11B: Subject Unit/Imaging Unit
12: Capsule Shaped Casing
12A: Tubular Casing
12B-12C: Dome-Shaped Casing
13A-13B: Illumination Unit
14A-14B: Optical System
15A-15B: Imaging Element
16: Wireless Communication Unit
17: Control Unit
19: Permanent Magnet
S1-S2- Imaging View Field
La- Long Axis 10: Capsule Endoscope
15A: Imaging Element
19: Permanent Magnet
C: Geometrical Center
Dg: Gravitational Force
G: Gravity
La: Long Axis
W: Water
Ws: Water Surface
Ym: Magnetization Direction
Yu: Vertical Direction 10: Capsule Endoscope
15A: Imaging Element
19: Permanent Magnet
M: Image
Pu: Upper Portion
W: Water
Ws: Water Surface
Ym: Magnetization Direction 10: Capsule Endoscope
19: Permanent Magnet
Mp: Peak Magnetic Field
Ms: Uniform Gradient Magnetic Field
Y1-Y3: Arrow

FIG.9

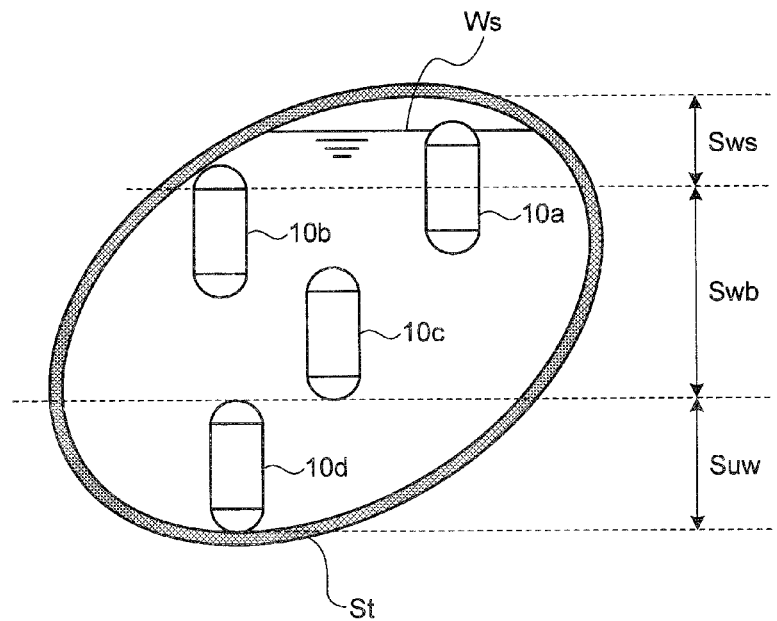

FIG.10

| GUIDANCE AREA | WATER SURFACE (INCLUDING UPPER STOMACH WALL) | UNDERWATER | WATER BOTTOM |
|---|---|---|---|
| TYPE OF MAGNETIC FIELD | PEAK MAGNETIC FIELD + VERTICAL DIRECTION GRADIENT MAGNETIC FIELD | UNIFORM GRADIENT MAGNETIC FIELD + UNIFORM MAGNETIC FIELD | UNIFORM GRADIENT MAGNETIC FIELD + UNIFORM MAGNETIC FIELD |

10a-10d: Capsule Endoscope
Ws: Water Surface
Swb: Underwater Area
Sws: Water Surface Area
Suw: Water Bottom Area
St: Stomach Wall 60: Operation Input Unit
61-62: Joystick
63: Guidance Area Switching Unit
63A: Water Surface Switch
63B: Underwater Switch
63C: Water Bottom Switch
64: Approach Button
64B: Down Button
64U: Up Button
65: Capture Button 10: Capsule Endoscope
61-62: Joystick
63: Guidance Area Switch Unit
64: Approach Button
64B: Down Button
64U: Up Button
65: Capture Button
Az: Vertical Axis
Hp: Horizontal Plane
La: Long Axis
Y11-Y14: Arrow
Y11j-Y14j: Arrow 10: Capsule Endoscope
61-62: Joystick
63: Guidance Area Switching Unit
64: Approach Button
64B: Down Button
64U: Up Button
65: Capture Button
Az: Vertical Axis
Hp: Horizontal Plane
La: Long Axis
Y21-Y25: Arrow
Y21j-Y25j: Arrow 10: Capsule Endoscope
19: Permanent Magnet
Ms4-Ms5: Uniform Gradient Magnet
Y24b-Y25: Arrow 10: Capsule Endoscope
19: Permanent Magnet
Ms3: Uniform Gradient Magnetic Field
Y23u: Arrow 10: Capsule Endoscope
61-62: Joystick
63: Guidance Area Switching Unit
64: Approach Button
64B: Down Button
64U: Up Button
65: Capture Button
Az: Vertical Axis
Hp: Horizontal Plane
La: Long Axis
Y31-Y32: Arrow
Y31j-Y32j: Arrow 10: Capsule Endoscope
61-62: Joystick
63: Guidance Area Switching Unit
64: Approach Button
64B: Down Button
64U: Up Button
65: Capture Button
Az: Vertical Axis
Hp: Horizontal Plane
La: Long Axis
Y122-Y125: Arrow
Y122j-Y125j: Arrow 10: Capsule Endoscope
61-62: Joystick
63: Guidance Area Switching Unit
64: Approach Button
64B: Down Button
64U: Up Button
65: Capture Button
Az: Vertical Axis
Hp: Horizontal Plane
La: Long Axis
Y131-Y134: Arrow
Y131j-Y134j: Arrow 10: Capsule Endoscope
M1: Arrow
M2: Guidance Menu
W: Water
Ws: Water Surface
Y41: Arrow 10: Capsule Endoscope
Ms: Uniform Gradient Magnetic Field
Sp: Imaging Object
St: Stomach Wall
Y42: Arrow (1)          (2)

(1)          (2)

10: Capsule Endoscope
G1-G2: Biological Image
Pr: Boundary
Pt: Contact Portion
St: Stomach Wall
W: Water
Ws: Water Surface 10: Capsule Endoscope
P10-P11: Position
Swb: Underwater Area
Sws: Water Surface Area
Suw: Water Bottom Area
St: Stomach Wall
W: Water
Ws: Water Surface
Y51-Y53: Arrow 10: Capsule Endoscope
St: Stomach Wall
W: Water
Ws: Water Surface
Y61-Y64: Arrow Gp1-Gp2- Posture Diagram
Y11g-Y14g: Arrow
Y21g-Y25g: Arrow Gp1-Gp2: Posture Diagram
Lws: Line
Lst: Line
Y31g-Y32g: Arrow (1)　　　　　　　　(2)　　　　　　　　(3)

(1)　　　　　　　　(2)

Td: Diving Mode Field
Tn: Guidance Area Field

11A: Imaging Unit
12b: Dome-Shaped Casing
13A: Illumination Unit
14A: Optical System
15A: Imaging Element
16: Wireless Communication Unit
17: Control Unit
18: Power Source Unit
19: Permanent Magnet
410: Capsule Endoscope
412: Capsule-Shaped Casing
412a: Tubular Casing
A14: Area
Pc: Capsule Endoscope Image
S1: Imaging View Field

CAPSULE MEDICAL DEVICE GUIDANCE SYSTEM

CROSS REFERENCES TO RELATED APPLICATIONS

This application is a continuation of PCT international application Ser. No. PCT/JP2010/063218 filed on Aug. 4, 2010 which designates the United States, incorporated herein by reference, and which claims the benefit of priority from Japanese Patent Applications No. 2009-256326, filed on Nov. 9, 2009, incorporated herein by reference.

BACKGROUND OF THE INVENTION

1. Field of the Invention

The present invention relates to a capsule medical device guidance system for guiding a capsule medical device introduced into a subject.

2. Description of the Related Art

Previously, in the field of endoscope, capsule medical devices have appeared which include an imaging function and a wireless communication function inside a capsule-shaped casing formed into a size that can be introduced into the digestive tract of a subject such as a patient. The capsule medical device is swallowed from a mouth of the subject, and then moves in the digestive tract by a peristaltic motion or the like. The capsule medical device sequentially captures images inside an organ of the subject (hereinafter, the image may be referred to as an in-vivo image) and sequentially wirelessly transmits the obtained in-vivo images to a receiving device outside the subject during a period from when the capsule medical device is introduced into the inside of the digestive tract of the subject to when the capsule medical device is discharged to the outside of the subject.

The in-vivo images captured by the capsule medical device are taken into an image display device via the receiving device. The image display device displays the taken in-vivo images as a still image or a moving image. A user such as a doctor or a nurse observes each in-vivo image of the subject displayed on the image display device, and examines the inside of the organ of the subject through the observation of the in-vivo images.

On the other hand, in recent years, a capsule medical device guidance system which guides a capsule medical device inside a subject by a magnetic force (hereinafter referred to as magnetic guidance) is proposed. Generally, in the capsule medical device guidance system, the capsule medical device further includes a permanent magnet inside the capsule-shaped casing, and the image display device displays in real time each in-vivo image sequentially captured by the capsule medical device inside the subject. The capsule medical device guidance system applies a magnetic field to the capsule medical device inside the subject and magnetically guides the capsule medical device inside the subject to a desired position by a magnetic force of the applied magnetic field. While observing the in-vivo image displayed on the image display device, the user operates the magnetic guidance of the capsule medical device by using an operating unit of the capsule medical device guidance system.

As the capsule medical device, there is a capsule endoscope which has a specific gravity capable of floating in a water introduced inside an organ so as to observe the inside of the organ having a relatively large space such as a stomach or a large intestine, and sequentially captures in-vivo images while floating in the water. To intensively examine the inside of an organ having a relatively large space such as a stomach, there is a case in which the subject ingests a water to stretch the inside of the organ (specifically, to stretch folds on the inner wall of the organ) and a capsule endoscope having a specific gravity smaller than that of the water (for example, see International Publication No. 2007/077922). In this case, while the capsule endoscope floats on the water surface with a predetermined posture (for example, a vertical posture in which the center axis in the longitudinal direction of the capsule endoscope is substantially perpendicular to the water surface) inside the organ such as a stomach, the capsule endoscope sequentially captures images of the inside of the organ stretched by the water. The capsule endoscope is moved in desired directions while floating on the water surface inside the organ, and thereby the capsule endoscope can capture a wide range of images inside the organ.

SUMMARY OF THE INVENTION

A capsule medical device guidance system according to an aspect of the present invention includes a capsule medical device that includes an imaging unit that captures an image in a subject, a transmitting unit that transmits an image captured by the imaging unit to the outside, and a magnetic field response unit; a magnetic field generator that generates a magnetic field to the magnetic field response unit to guide the capsule medical device; a receiving unit that receives the image in the subject transmitted from the capsule medical device; a display unit that displays the image in the subject received by the receiving unit; an operation input unit for inputting operation information for magnetically guiding the capsule medical device; a control unit that controls the magnetic field generator to guide the capsule medical device in accordance with the operation information input by the operation input unit; and a storage unit that stores control content by the control unit. The magnetic field generator generates, in a space in which the capsule medical device is guided, either a trapping magnetic field that attracts the magnetic field response unit at any position on a horizontal plane and traps the capsule medical device or a gradient magnetic field that has a substantially uniform magnetic field gradient and forces the magnetic field response unit. When the control unit switches the magnetic field generated by the magnetic field generator from the trapping magnetic field to the gradient magnetic field, the control unit causes the storage unit to store a generation position on the horizontal plane of the trapping magnetic field, and when the control unit switches a magnetic field generated by the magnetic field generator from the gradient magnetic field to the trapping magnetic field, the control unit causes the magnetic field generator to generate the trapping magnetic field at the position stored in the storage unit.

A capsule medical device guidance system according to another aspect of the present invention includes a capsule medical device that includes an imaging means for capturing an image in a subject, a transmitting means for transmits an image captured by the imaging unit to the outside, and a magnetic field response means; a magnetic field generating means for generating a magnetic field to the magnetic field response means to guide the capsule medical device; a receiving means for receiving the image in the subject transmitted from the capsule medical device; a display means for displaying the image in the subject received by the receiving means; an operation input means for inputting operation information for magnetically guiding the capsule medical device; a control means for controlling the magnetic field generator to guide the capsule medical device in accordance with the operation information input by the operation input means;

and a storage means for storing control content by the control means. The magnetic field means generates, in a space in which the capsule medical device is guided, either a trapping magnetic field that attracts the magnetic field response means at any position on a horizontal plane and traps the capsule medical device or a gradient magnetic field that has a substantially uniform magnetic field gradient and forces the magnetic field response means. When the control means switches the magnetic field generated by the magnetic field generating means from the trapping magnetic field to the gradient magnetic field, the control means causes the storage means to store a generation position on the horizontal plane of the trapping magnetic field, and when the control means switches a magnetic field generated by the magnetic field generating means from the gradient magnetic field to the trapping magnetic field, the control means causes the magnetic field generating means to generate the trapping magnetic field at the position stored in the storage means.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 9 is a diagram showing a state in which the capsule endoscopes are located inside a stomach of the subject;

FIG. 10 is a diagram showing a table that shows types of magnetic field corresponding to each guidance area shown in FIG. 9;

DETAILED DESCRIPTION OF THE PREFERRED EMBODIMENTS

Figure 1:
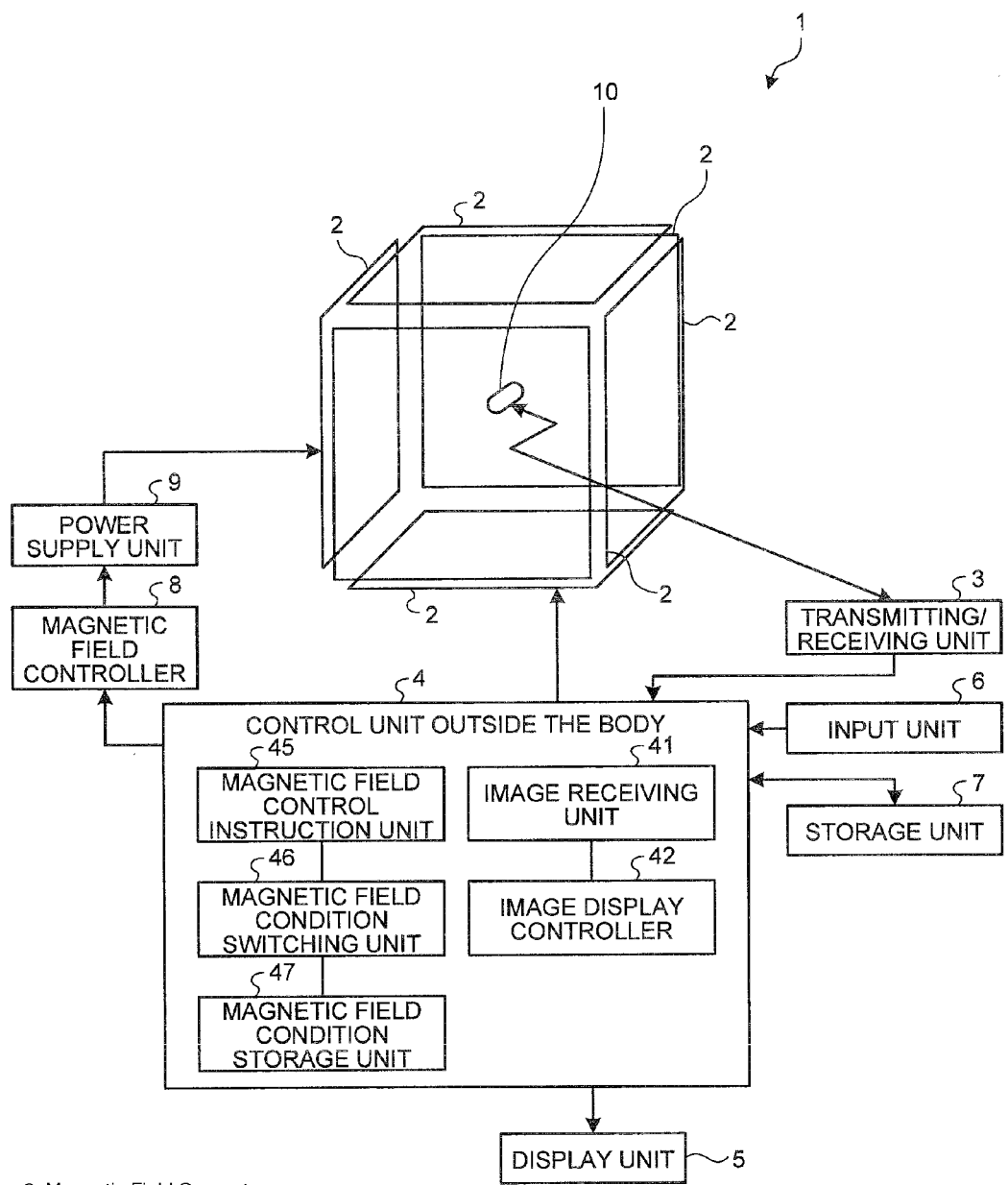
FIG. 1 is a schematic diagram showing an entire configuration of a capsule medical device guidance system according to a first embodiment.

Hereinafter, the capsule medical device guidance system according to embodiments of the present invention will be described by using an example of a capsule medical device system that uses a capsule endoscope which is orally introduced into a subject and floats on a water stored in a stomach, a small intestine, or a large intestine of the subject as a device introduced inside the subject. However, it is not limited to this, and various devices introduced inside the subject can be used, such as, for example, a monocular capsule endoscope or a pantoscopic capsule endoscope which captures in-vivo images inside the subject by performing an image capturing operation while moving through the lumen from the esophagus to the anus. The embodiments do not limit the present invention. In the drawings, the same components are given the same reference numerals.

First Embodiment

First, a first embodiment will be described. FIG. 1 is a schematic diagram showing an entire configuration of the capsule medical device guidance system according to a first embodiment of the present invention. As shown in FIG. 1, a capsule medical device guidance system 1 according to the first embodiment includes a capsule endoscope 10 which is a capsule medical device that is swallowed from a mouth of the subject, introduced into a body cavity in the subject, and communicates with an external device. The capsule medical device guidance system 1 has a magnetic field generator 2 which is provided around the subject and can generate a three-dimensional magnetic field. The capsule medical device guidance system 1 has a transmitting/receiving unit 3 which performs wireless communication with the capsule endoscope 10 and receives a wireless signal including an image captured by the capsule endoscope 10, as well as transmits an operation signal to the capsule endoscope 10. The capsule medical device guidance system 1 has an external control unit 4, which controls each constituent unit of the capsule medical device guidance system 1. The capsule medical device guidance system 1 has a display unit 5 that outputs and displays the image captured by the capsule endoscope 10. The capsule medical device guidance system 1 has an input unit 6 that inputs instruction information for instructing various operations performed in the capsule medical device guidance system 1 such as operation information for magnetically guiding the capsule endoscope 10 into the external control unit 4. The capsule medical device guidance system 1 has a storage unit 7 that stores image information captured by the capsule endoscope 10 and the like. The capsule medical device guidance system 1 has a magnetic field controller 8 that controls a magnetic field related to the magnetic field generator 2. The capsule medical device guidance system 1 has a power supply unit 9 that supplies electric power according to a control of the magnetic field controller 8 to the magnetic field generator 2.

The transmitting/receiving unit 3 may detects a position and a posture of the capsule endoscope 10 in the subject on the basis of received electrical field intensity of a signal transmitted by the capsule endoscope 10. Of course, a position detecting apparatus that detects a position and a posture of the capsule endoscope 10 may be provided separately. For example, a magnetic field generator or a magnetic field reflector is provided in the capsule endoscope 10, a plurality of magnetic field sensors are provided so that the magnetic field sensors surround the capsule endoscope 10 in the same manner as the magnetic field generator 2, and the position and the posture of the capsule endoscope 10 may be detected on the basis of the detection results of the magnetic field sensors.

The capsule endoscope 10 is a capsule type medical device that obtains in-vivo images of the subject. The capsule endoscope 10 includes an image capturing function and a wireless communication function. The capsule endoscope 10 is introduced into the inside of an organ of the subject by an oral intake or the like. Thereafter, the capsule endoscope 10 inside the subject moves inside the digestive tract, and finally, discharged to the outside of the subject. The capsule endoscope 10 sequentially captures in-vivo images of the subject and sequentially transmits the obtained in-vivo images to the external transmitting/receiving unit 3 by wireless communication during a period from when the capsule endoscope 10 is introduced into the inside of the subject to when the capsule endoscope 10 is discharged to the outside of the subject. The capsule endoscope 10 contains a magnetic body such as a permanent magnet. The capsule endoscope 10 floats in water introduced inside of an organ (for example, stomach) of the subject, and the capsule endoscope 10 is magnetically guided by the external magnetic field generator 2.

The magnetic field generator 2 magnetically guides the capsule medical device inside the subject. The magnetic field generator 2 is realized by using a plurality of coils or the like, and generates guidance magnetic field by using the electric power supplied by the power supply unit 9. The magnetic field generator 2 applies the generated guidance magnetic field to the magnetic body inside the capsule endoscope 10 to magnetically capture the capsule endoscope 10 by an action of the guidance magnetic field. The magnetic field generator 2 controls three-dimensional posture of the capsule endoscope 10 inside the subject by changing a magnetic field direction of the guidance magnetic field acting on the capsule endoscope 10 inside the subject.

The transmitting/receiving unit 3 includes a plurality of antennas, and receives the in-vivo images of the subject from the capsule endoscope 10 through the antennas. The transmitting/receiving unit 3 sequentially receives the wireless signal from the capsule endoscope 10 through the antennas. The transmitting/receiving unit 3 selects an antenna which has the highest received electric-field strength from the plurality of antennas, and performs demodulation processing or the like on the wireless signal received from the capsule endoscope 10 through the selected antenna. Thereby, the transmitting/receiving unit 3 extracts image data captured by the capsule endoscope 10, that is to say, in-vivo image data of the subject, from the wireless signal. The transmitting/receiving unit 3 transmits an image signal including the extracted in-vivo image data to the external control unit 4.

The external control unit 4 controls each operation of the magnetic field generator 2, the display unit 5, the storage unit 7, and the magnetic field controller 8, and controls input and output of signals between the constituent units. The external control unit 4 includes an image receiving unit 41 that sequentially obtains the in-vivo images sequentially received by the transmitting/receiving unit 3 and an image display controller 42 that displays the in-vivo images sequentially received by the transmitting/receiving unit 3 in real time on the display unit 5. The external control unit 4 controls the storage unit 7 to store an in-vivo image group of the subject obtained from the transmitting/receiving unit 3. When the input unit 6 inputs instruction information for instructing selective storage of an in-vivo image, the image display controller 42 extracts the in-vivo image which the instruction information instructs to store (that is to say, an image selected by a user) from the in-vivo image group of the subject, and controls the display unit 5 to additionally display a reduced image (thumbnail image or the like) of the in-vivo image.

The external control unit 4 has a magnetic field control instruction unit 45 that provides a magnetic field generation condition to the magnetic field controller 8 to guide the capsule endoscope 10 in accordance with the operation information input by the input unit 6. The external control unit 4 has a magnetic field condition switching unit 46 that switches the magnetic field generated by the magnetic field generator 2. The external control unit 4 has a magnetic field condition storage unit 47 that stores magnetic field conditions. When the input unit 6 inputs the operation information of the capsule endoscope 10, the magnetic field control instruction unit 45 instructs the magnetic field controller 8 to generate a magnetic field in accordance with a magnetic guidance direction and a magnetic guidance position specified by the operation information.

The display unit 5 is realized by using various types of display such as a liquid crystal display, and displays various information which is instructed to be displayed by the external control unit 4. Specifically, the display unit 5 displays, for example, the in-vivo image group of the subject captured by the capsule endoscope 10 on the basis of the control of the image display controller 42 in the external control unit 4. On the other hand, the display unit 5 displays a reduced image of an in-vivo image selected or marked from the in-vivo image group by an input operation of the input unit 6, patient information and examination information of the subject, and the like.

The input unit 6 has input devices such as a keyboard and a mouse, and inputs various information into the external control unit 4 according to an input operation by an operator such as a doctor. The various information input from the input unit 6 to the external control unit 4 includes, for example, instruction information for instructing the external control unit 4, patient information and the examination information of the subject. The patient information of the subject is identification information for identifying the subject, and includes, for example, patient name, patient ID, birth date, sex, and age of the subject. The examination information of the subject is identification information for identifying an examination in which the capsule endoscope 10 is introduced into the digestive tract of the subject and the inside of the digestive tract is observed, and for example, the examination information is examination ID, examination date, and the like. The input unit 6 inputs the operation information for the magnetic field generator 2 to operate the magnetic guidance of the capsule endoscope 10. For example, the input unit 6 includes an operation input unit having joysticks. A doctor or the like operates the joysticks so as to input, for example, the operation information for magnetically guiding the capsule endoscope 10, such as a magnetic guidance direction and a magnetic guidance position of the capsule endoscope 10 that is the target of the magnetic guidance operation, into the external control unit 4.

The storage unit 7 is realized by using a storage media, which rewritably store information, such as a flash memory or a hard disk. The storage unit 7 stores various information instructed to be stored by the control unit 4 outside of body, and transmits information instructed to be read from the stored various information by the external control unit 4 to the external control unit 4. The various information stored by the storage unit 7 includes, for example, each image data in the in-vivo image group of the subject captured by the capsule endoscope 10, data of the in-vivo image group selected from each in-vivo image displayed by the display unit 5 by an input operation of the input unit 6, input information by the input unit 6, such as the patient information of the subject, and the like.

The magnetic field controller 8 controls the amount of current supplied from the power supply unit 9 to the magnetic field generator 2 on the basis of instruction information provided from the external control unit 4, and controls the magnetic field generator 2 to generate a guidance magnetic field necessary for the magnetic guidance of the capsule endoscope 10 in accordance with a magnetic guidance direction and a magnetic guidance position based on the operation information through the control of the power supply unit 9.

The power supply unit 9 supplies electric power (for example, AC power) necessary to generate the above-described guidance magnetic field to the magnetic field generator 2 on the basis of the controls of the external control unit 4 and the magnetic field controller 8. In this case, the power supply unit 9 appropriately supplies necessary electric power to each of the plurality of coils included in the magnetic field generator 2. The magnetic field direction and the magnetic field strength of the guidance magnetic field generated by the magnetic field generator 2 are controlled by the amount of current supplied from the power supply unit 9 to each coil in the magnetic field generator 2.

Figure 2:
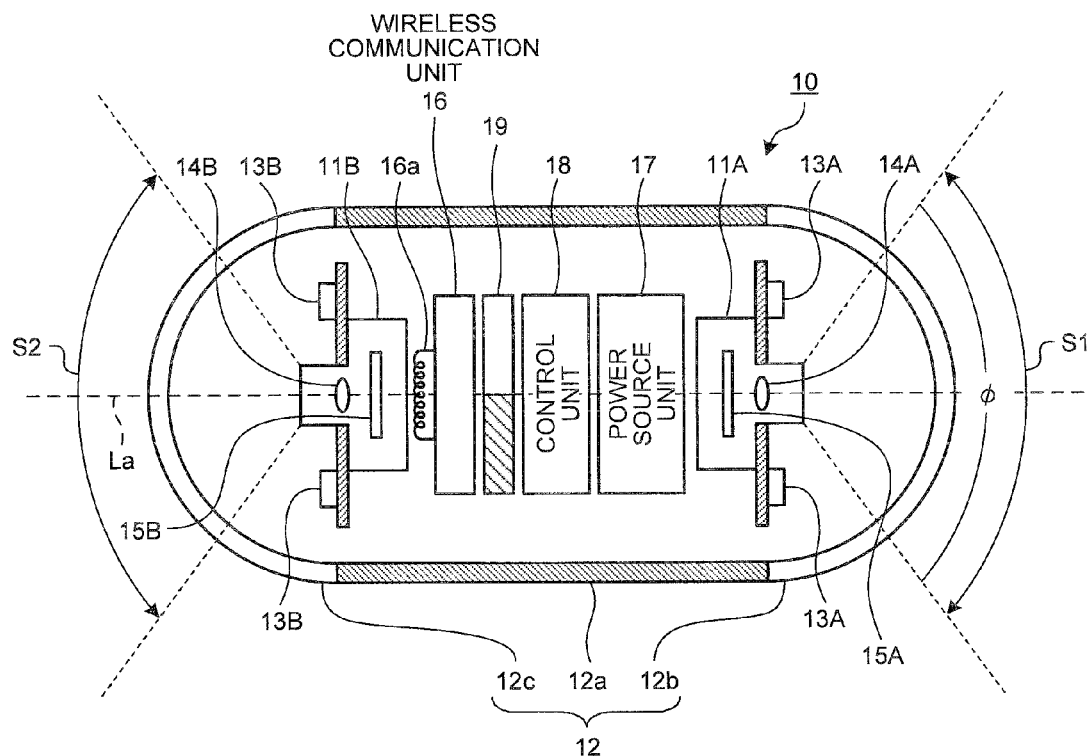
FIG. 2 is a cross-sectional schematic diagram showing a configuration example of a capsule endoscope shown in FIG. 1.

Next, the capsule endoscope 10 will be described. FIG. 2 is a cross-sectional schematic diagram showing a configuration example of the capsule endoscope shown in FIG. 1. As shown in FIG. 2, the capsule endoscope 10 includes a capsule-shaped casing 12 that is an outer covering formed in a size which can be easily introduced into the inside of an organ of the subject and imaging units 11A and 11B that respectively capture images of the subject in the image capturing directions different from each other. The capsule endoscope 10 also includes a wireless communication unit 16 that wirelessly transmits images captured by the imaging units 11A and 11B to the outside, a control unit 17 that controls constituent unit of the capsule endoscope 10, and a power source unit 18 that supplies electric power to constituent unit of the capsule endoscope 10. Further, the capsule endoscope 10 includes a permanent magnet 19 that enables the above-described magnetic guidance by the magnetic field generator 2. The permanent magnet functions as a magnetic field response unit.

The capsule-shaped casing 12 that is an outer case formed in a size capable of being introduced into the inside of an organ of the subject, and has a configuration in which both opening ends of a tubular casing 12a are closed by dome-shaped casings 12b and 12c. The dome-shaped casings 12b and 12c are dome-shaped optical members transparent to light of a predetermined wavelength band such as visible light. The tubular casing 12a is a colored casing that is substantially opaque to visible light. As shown in FIG. 2, the capsule-shaped casing 12 that includes the tubular casing 12a and the dome-shaped casings 12b and 12c liquid-tightly contains the imaging units 11A and 11B, the wireless communication unit 16, the control unit 17, the power source unit 18, and the permanent magnet 19.

The imaging units 11A and 11B respectively capture images in the image capturing directions different from each other. Specifically, the imaging unit 11A has an illumination unit 13A such as an LED, an optical system 14A such as a condenser lens, and an imaging element 15A such as a CMOS image sensor or a CCD. The illumination unit 13A emits illumination light such as white light to a imaging view field S1 of the imaging element 15A and illuminates the subject in the imaging view field S1 (for example, inner wall of an organ in the imaging view field S1 inside the subject) through the dome-shaped casing 12b. The optical system 14A collects reflected light from the imaging view field S1 on an imaging surface of the imaging element 15A and forms a subject image of the imaging view field S1 on the imaging surface of the imaging element 15A. The imaging element 15A receives the reflected light from the imaging view field S1 via the imaging surface and photoelectrically converts the received light signal to capture the subject image of the imaging view field S1, which is an in-vivo image of the subject. The imaging unit 11B has an illumination unit 13B such as an LED, an optical system 14B such as a condenser lens, and an imaging element 15B such as a CMOS image sensor or a CCD. The illumination unit 13B emits illumination light such as white light to a imaging view field S2 of the imaging element 15B and illuminates the subject in the imaging view field S2 (for example, inner wall of an organ in the imaging view field S2 inside the subject) through the dome-shaped casing 12c. The optical system 14B collects reflected light from the imaging view field S2 on an imaging surface of the imaging element 15B and forms a subject image of the imaging view field S2 on the imaging surface of the imaging element 15B. The imaging element 15B receives the reflected light from the imaging view field S2 via the imaging surface and photoelectrically converts the received light signal to capture the subject image of the imaging view field S2, which is an in-vivo image of the subject.

As shown in FIG. 2, when the capsule endoscope 10 is a two-lens capsule medical device that captures images in the front and the rear of the device in the long axis La direction, the optical axes of the imaging units 11A and 11B are substantially in parallel with the long axis La or substantially correspond to the long axis La which is the central axis in the longitudinal direction of the capsule-shaped casing 12. The directions of the imaging view fields S1 and S2 of the imaging units 11A and 11B, in other words, the image capturing directions of the imaging units 11A and 11B, are opposite to each other.

The wireless communication unit 16 includes an antenna 16a and sequentially wirelessly transmits images captured by the above-described imaging units 11A and 11B to the outside via the antenna 16a. Specifically, the wireless communication unit 16 obtains an image signal of an in-vivo image of the subject captured by the imaging unit 11A or the imaging unit 11B from the control unit 17, performs modulation processing or the like on the obtained image signal, and generates a wireless signal modulated from the image signal. The wireless communication unit 16 transmits the wireless signal to the external transmitting/receiving unit 3 via the antenna 16a.

The control unit 17 controls each operation of the imaging units 11A and 11B and the wireless communication unit 16 that are constituent units of the capsule endoscope 10, and controls input and output of signals between the constituent units. Specifically, the control unit 17 causes the imaging element 15A to capture an image of the subject in the imaging view field S1 illuminated by the illumination unit 13A and causes the imaging element 15B to capture an image of the subject in the imaging view field S2 illuminated by the illumination unit 13B. The control unit 17 has a signal processing function to generate an image signal. The control unit 17 obtains in-vivo image data of the imaging view field S1 from the imaging element 15A, and each time the control unit 17 obtains the in-vivo image data, the control unit 17 performs predetermined signal processing on the in-vivo image data and generates an image signal including the in-vivo image data of the imaging view field S1. Similarly, the control unit 17 obtains in-vivo image data of the imaging view field S2 from the imaging element 15B, and each time the control unit 17 obtains the in-vivo image data, the control unit 17 performs predetermined signal processing on the in-vivo image data and generates an image signal including the in-vivo image data of the imaging view field S2. The control unit 17 controls the wireless communication unit 16 to sequentially wirelessly transmit the image signals to the outside in a chronological order.

The power source unit 18 is an electric accumulator such as a button-shaped battery or a capacitor, and the power source unit 18 includes a switch unit such as a magnetic switch. The ON/OFF state of the power source unit 18 is switched by a magnetic field applied from the outside. During the ON-state, the power source unit 18 appropriately supplies the power in the electric accumulator to each constituent unit (imaging units 11A and 11B, wireless communication unit 16, and control unit 17) in the capsule endoscope 10. During the OFF-state, the power source unit 18 stops the supply of the power to each constituent unit in the capsule endoscope 10.

The permanent magnet 19 enables the magnetic guidance of the capsule endoscope 10 by the above-described magnetic field generator 2. The permanent magnet 19 is disposed and fixed inside the capsule-shaped casing 12 in a state in which the permanent magnet 19 is relatively fixed to the above-described imaging units 11A and 11B. In this case, the permanent magnet 19 is magnetized in a known direction relatively fixed to the vertical direction of each imaging surface of the imaging elements 15A and 15B.

Figure 3:
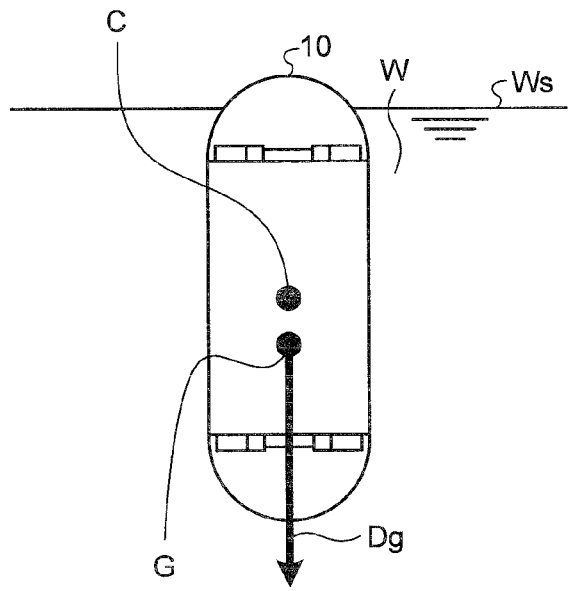
FIG. 3 is a conceptual diagram for explaining a state in which the capsule endoscope floats in water introduced into a subject.

Here, a state in which the capsule endoscope 10 floats in water W introduced into the subject will be described with reference to FIG. 3. FIG. 3 is a conceptual diagram for explaining the state in which the capsule endoscope 10 floats in the water W introduced into the subject. However, in an example shown in FIG. 3, a case in which the magnetic field for controlling the posture (orientation of the long axis La) of the capsule endoscope 10 is not applied to the permanent magnet 19 is illustrated.

The specific gravity of the capsule endoscope 10 illustrated in the first embodiment relative to the water W is smaller than 1. Therefore, as shown in FIG. 3, the capsule endoscope 10 floats in the water W. In this case, the center of gravity G of the capsule endoscope 10 is shifted from the geometrical center C of the capsule endoscope 10 along the long axis La (see FIG. 2) of the capsule endoscope 10. Specifically, the center of gravity G of the capsule endoscope 10 is set at a position that is on the long axis La and shifted from the geometrical center C of the capsule-shaped casing 12 toward the imaging unit 11B by adjusting the arrangement of the constituent units of the capsule endoscope 10 such as the power source unit 18 and the permanent magnet 19. Based on this, the long axis La of the capsule endoscope 10 floating in the water W becomes in parallel with the vertical direction (that is, the direction of gravitational force Dg). In other words, it is possible to float the capsule endoscope 10 in the water W in an upright posture. The upright posture mentioned above is a posture in which the long axis La of the capsule-shaped casing 12 (a line connecting the geometrical center C and the center of gravity G) is substantially in parallel with the vertical direction. In the upright posture, the capsule endoscope 10 sets the imaging view field S1 of the imaging unit 11A in the upper vertical direction and the imaging view field S2 of the imaging unit 11B in the lower vertical direction. The long axis La of the capsule endoscope 10 is the central axis in the longitudinal direction of the capsule endoscope 10. The water W is a liquid harmless to the human body such as water or physiological saline. The capsule endoscope 10 is not necessarily needed to be partially above the water surface Ws, and the specific gravity of the capsule endoscope 10 relative to the water W may be set so that the capsule endoscope 10 sinks into the water.

Figure 4:
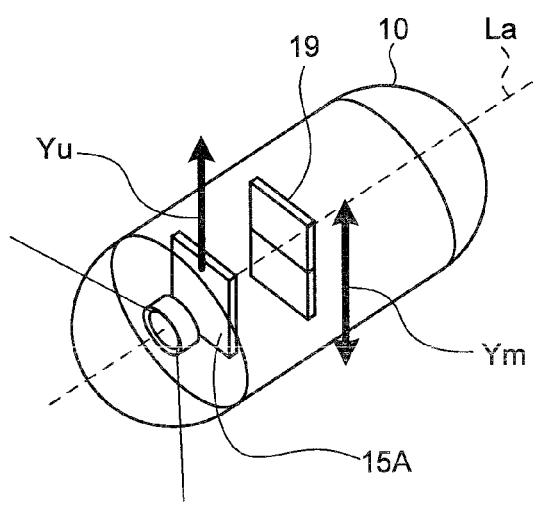
FIG. 4 is a diagram for explaining a magnetization direction of a permanent magnet in the capsule endoscope.

As shown in FIG. 4, the permanent magnet 19 is fixed in the casing 12 so that the magnetization direction Ym of the permanent magnet 19 has an angle (for example, a right angle) relative to the long axis La of the capsule endoscope 10. Specifically, the permanent magnet 19 is fixed in the capsule-shaped casing 12 so that the magnetization direction Ym is perpendicular to the long axis La. Based on this configuration, when the capsule endoscope 10 floats in the water W, the magnetization direction Ym of the permanent magnet 19 in the capsule endoscope 10 is the horizontal direction. A plane that includes the magnetization direction Ym of the permanent magnet 19 and a direction (a displacement direction) from the geometrical center C of the capsule-shaped casing 12 to the center of gravity G of the capsule endoscope 10, which is shifted from the geometrical center C, is a vertical plane. Therefore, when applying a magnetic field, the posture of the capsule endoscope 10 changes so that the vertical plane with respect to the magnetic field includes the magnetization direction Ym. The permanent magnet 19 moves following the magnetic field applied from the outside, and as a result, the magnetic guidance of the capsule endoscope 10 by the magnetic field generator 2 is implemented. In this case, the capsule endoscope 10 performs an operation to change at least one of the position, the posture, and the direction of the capsule endoscope 10 in the subject by an action of the permanent magnet 19. For example, by applying a rotating magnetic field that rotates around a certain point on the vertical axis to the permanent magnet 19, it is possible to oscillate the distal end of the capsule endoscope 10. Also, by applying a magnetic field that rotates around the vertical axis to the permanent magnet 19, it is possible to rotate the capsule endoscope 10 around the vertical axis. Or, the capsule endoscope 10 maintains a state in which the capsule endoscope 10 is stopped at a desired position in the subject by an action of the permanent magnet 19.

Next, a relative relationship between the imaging elements 15A, 15B and the permanent magnet 19 that are contained in the capsule endoscope 10 will be described. As shown in FIGS. 2 and 4, the two imaging units 11A and 11B are disposed so that, for example, the optical central axes of the imaging elements 15A and 15B, which are respectively included in the imaging units 11A and 11B, overlap the long axis La and the imaging directions of the imaging elements 15A and 15B are opposite to each other. In other words, the imaging units 11A and 11B are mounted so that the imaging surfaces of the imaging elements 15A and 15B are perpendicular to the long axis La. The permanent magnet 19 is disposed inside the capsule-shaped casing 12 in a state in which the permanent magnet 19 is relatively fixed to the imaging elements 15A and 15B. In this case, the permanent magnet 19 is disposed in the capsule endoscope 10 so that the magnetization direction Ym of the permanent magnet 19 is in parallel with the vertical direction Yu of the imaging surfaces of the imaging elements 15A and 15B as shown in FIG. 4. By setting the center of gravity G on the long axis La and mounting the imaging units 11A and 11B so that the imaging surfaces of the imaging elements 15A and 15B are perpendicular to the long axis La, it is possible to orthogonalize the imaging surfaces of the imaging elements 15A and 15B to a plane that includes the magnetization direction of the permanent magnet 19 and the displacement direction from the geometrical center C to the center of gravity G.

Figure 5:
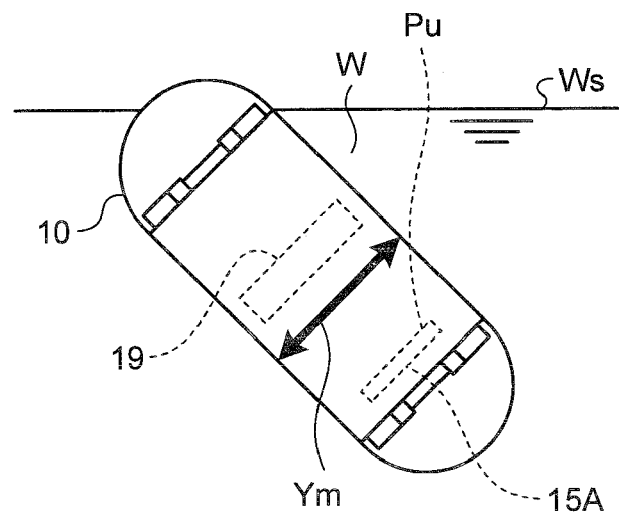
FIG. 5 is a conceptual diagram for explaining an example of a posture of the capsule endoscope in the water introduced into the subject.

An angle of the long axis La of the capsule endoscope 10 relative to the direction of gravitational force Dg can be controlled by applying a magnetic field from the outside to the permanent magnet 19 of the capsule endoscope 10. As shown in FIG. 5, by applying a magnetic field whose magnetic line of force has an angle relative to the horizontal plane, the capsule endoscope 10 can be tilted from the direction of gravitational force Dg so that the magnetization direction Ym of the permanent magnet 19 is substantially in parallel with the magnetic line. Therefore, in a state in which the capsule endoscope 10 is tilted, only by applying a rotating magnetic field that rotates around the vertical axis to the permanent magnet 19 and rotating the capsule endoscope 10 around the vertical axis, it is possible to easily obtain the in-vivo images around the capsule endoscope 10.

Figure 6:
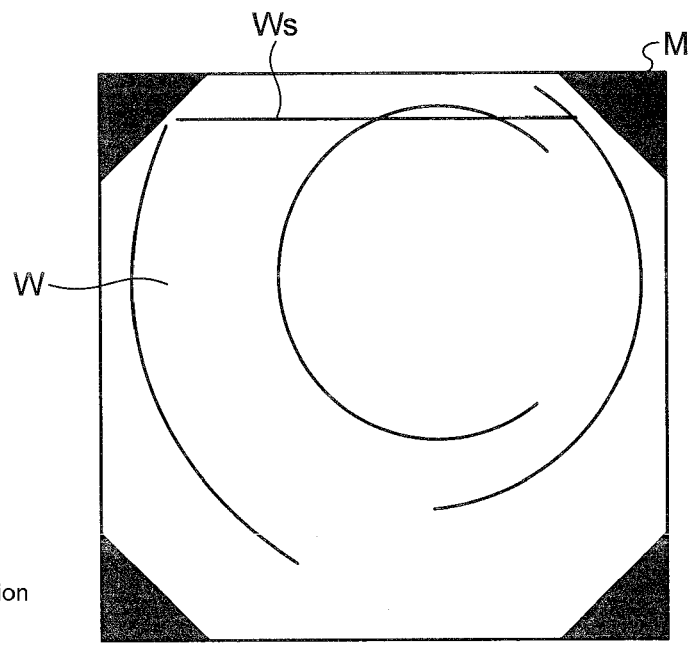
FIG. 6 is a diagram showing an example of an image displayed on a display screen of a display unit shown in FIG. 1.

The display unit 5 displays the in-vivo image of the subject obtained by the capsule endoscope 10 in a display mode in which the up/down direction of the subject in the in-vivo image following the magnetic guidance of the capsule endoscope 10 is matched to the up-down direction of the display screen. For example, as illustrated in FIG. 6, the display unit 5 displays an image M on the display screen so that the water surface (an upper boundary between the water and the outside, hereinafter the water surface indicates the same) Ws captured by the element in the upper portion Pu of the imaging element 15A of the capsule endoscope 10 is located in the upper portion of the image M. Since the magnetization direction Ym of the permanent magnet 19 is in parallel with the up/down direction Yu of the imaging surfaces of the imaging elements 15A and 15B, a direction in parallel with the magnetization direction Ym of the permanent magnet 19 matches the up/down direction of the display screen.

Figure 7:
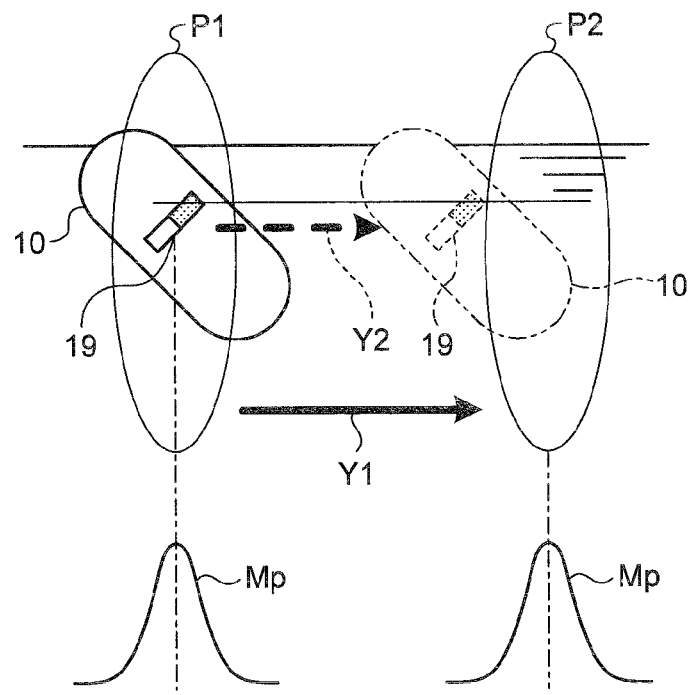
FIG. 7 is a diagram for explaining a peak magnetic field generated by a magnetic field generator shown in FIG. 1.

Next, the types of the magnetic field generated by the magnetic field generator 2 will be described. The magnetic field generator 2 can generate a peak magnetic field and a uniform gradient magnetic field in addition to a so-called uniform magnetic field. As shown by a peak magnetic field Mp in FIG. 7, the peak magnetic field is a magnetic field that has a peak of magnetic field strength in a direction perpendicular to the horizontal plane. The peak magnetic field can attract the permanent magnet 19 to the peak position of the magnetic field strength and trap the capsule endoscope 10. In other words, the peak magnetic field is a trapping magnetic field that attracts the permanent magnet 19 of the capsule endoscope 10 to an arbitrary position in the horizontal direction and traps the capsule endoscope 10. For example, the magnetic field generator 2 can move the capsule endoscope 10 from the position P1 to the position P2 as shown by the arrow Y2 by moving the peak position of the peak magnetic field Mp from the position P1 to the position P2 as shown by the arrow Y1.

Figure 8:
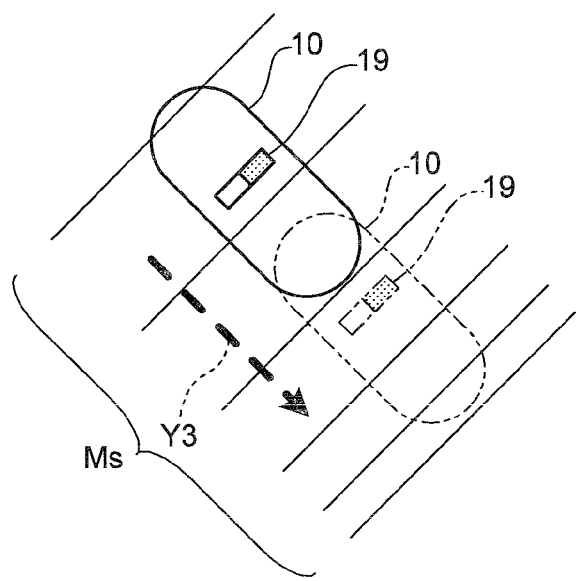
FIG. 8 is a diagram for explaining a uniform gradient magnetic field generated by a magnetic field generator shown in FIG. 1.

The uniform gradient magnetic field has a substantially uniform magnetic field gradient as shown by the uniform gradient magnetic field Ms in FIG. 8. The uniform gradient magnetic field forces the permanent magnet 19 in a direction in which the distribution of magnetic field strength varies from sparse to dense. For example, the magnetic field generator 2 generates a uniform gradient magnetic field Ms in which the distribution of magnetic field strength varies from sparse to dense in a direction from upper left to lower right so as to force the permanent magnet 19 to the direction shown by the arrow Y3, and thereby moves the capsule endoscope 10 in the direction shown by the arrow Y3.

Here, in the first embodiment, the magnetic field generated by the magnetic field generator 2 is switched depending on which position the capsule endoscope 10 is guided to; the water surface, the underwater, or the water bottom (an lower boundary between the water and the outside, hereinafter the water bottom indicates the same), First, a guidance area to which the capsule endoscope 10 is guided will be described with reference to FIG. 9 by using an example in which the capsule endoscope 10 floats inside a stomach. As shown in FIG. 9, as the guidance areas, the water surface area Sws where a capsule endoscope 10a near the water surface is located, the underwater area Swb where a capsule endoscope 10c floating under the water is located, and the water bottom area Suw where a capsule endoscope 10d in contact with the bottom surface of stomach wall are set. The water surface area Sws includes a case in which a capsule endoscope is in contact with an upper portion of the stomach wall St as shown by a capsule endoscope 10b. The magnetic fields to be generated are set respectively for each guidance area of the water surface area Sws, the underwater area Swb, and the water bottom area Suw, and magnetic field conditions respectively corresponding to each guidance area are stored in the magnetic field condition storage unit 47.

When the input unit 6 inputs selection information for selecting one guidance area from the water surface area Sws, the underwater area Swb, and the water bottom area Suw, the magnetic field condition switching unit 46 reads a magnetic field condition corresponding to the selected guidance area from the magnetic field conditions stored in the magnetic field condition storage unit 47 and switches the magnetic field generated by the magnetic field generator 2 to a magnetic field corresponding to the selected guidance area on the basis of the selection information. The magnetic field condition switching unit 46 switches at least one of the guidance direction of the capsule endoscope 10 by the magnetic field generated by the magnetic field generator 2, the type of the magnetic field generated by the magnetic field generator 2, and the amplitude and the direction of the magnetic field gradient generated in a direction perpendicular to the direction of the magnetic field generated by the magnetic field generator 2 according to the guidance area selected by the selection information input from the input unit 6. The magnetic field condition switching unit 46 switches the type of the magnetic field generated by the magnetic field generator 2 to either the peak magnetic field or the uniform gradient magnetic field according to the guidance area selected by the selection information input from the input unit 6. Then the magnetic field control instruction unit 45 instructs the magnetic field controller 8 to cause the magnetic field generator 2 to generate a magnetic field according to the operation information input from the input unit 6 for magnetically guiding the capsule endoscope 10.

Next, the types of magnetic field corresponding to each guidance area will be described. FIG. 10 is a diagram illustrating a table T1 showing the types of magnetic field corresponding to each guidance area. As shown in table T1 in FIG. 10, the types of magnetic field corresponding to the water surface area (including a case in which the capsule endoscope 10 is in contact with an upper portion of the stomach wall) among the guidance areas are a peak magnetic field and a vertical direction gradient magnetic field having a gradient in the vertical direction. In the water surface area, the capsule endoscope 10 needs to be moved along the water surface. Since the peak magnetic field can trap the capsule endoscope 10 at a position in the horizontal direction and perform a stable guidance on the water surface, the peak magnetic field is suitable to guide the capsule endoscope 10 in the horizontal direction in the water surface area. Here, although the uniform gradient magnetic field can generate a large force, the uniform gradient magnetic field technically includes a magnetic field distortion, so that the movement of the capsule endoscope 10 by the uniform gradient magnetic field becomes unstable in an environment without friction such as the water surface, and it is not possible to hold the capsule endoscope 10 at a position instructed by an operation. Therefore, in the water surface area, it is set that the uniform gradient magnetic field is not applied.

The types of magnetic field corresponding to the underwater area are the uniform gradient magnetic field and the uniform magnetic field. Although the peak magnetic field can trap the capsule endoscope 10 at a position in the horizontal direction, the peak magnetic field cannot hold the capsule endoscope 10 at a position in the vertical direction under the water. Since the guidance principles in the horizontal direction and the vertical direction are different from each other, it is difficult to generate, under the water, a peak magnetic field in which movements of each control axis are accurately combined as shown by a movement direction under the water described below. Therefore, the capsule endoscope 10 is guided by applying the uniform gradient magnetic field and the uniform magnetic field instead of the peak magnetic field.

The types of magnetic field corresponding to the water bottom area are the uniform gradient magnetic field and the uniform magnetic field in the same manner as in the underwater area. In the water bottom area, it is difficult to move the position of the capsule endoscope 10 in the horizontal direction along the surface of the stomach wall due to the friction of the surface of the stomach wall and the influence of the shape of the surface of the stomach wall. Therefore, it is set that the capsule endoscope 10 is not guided in the horizontal direction in the water bottom area, and accordingly, the peak magnetic field is excluded from the types of magnetic field corresponding to the water bottom area.

As described above, in the first embodiment, the type of the magnetic field applied to the permanent magnet 19 is automatically switched for each guidance area, and the guidance of the capsule endoscope 10 suitable for each guidance area can be implemented. Further, in the first embodiment, an operator can correctly guide the capsule endoscope 10 with an easy operation because the operator only has to select a desired guidance area without setting an appropriate type of magnetic field selecting from many conditions of the guidance areas.

Figure 11:
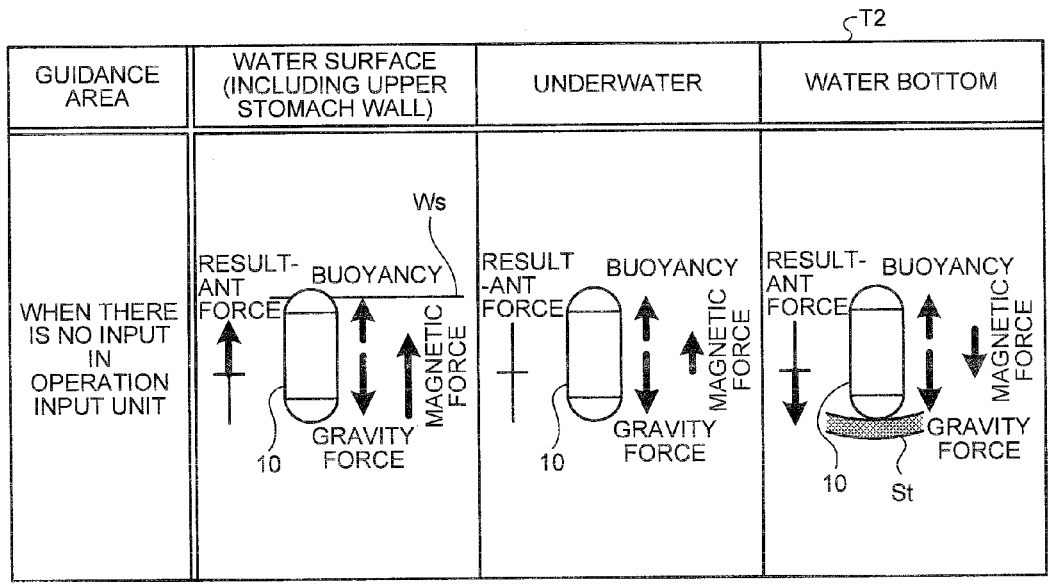
FIG. 11 is a diagram showing a table that shows magnetic fields generated in each guidance area when there is no operation information for magnetic guidance in an operation input unit.

When the input unit 6 selects a guidance area, the magnetic fields described below are automatically generated from the magnetic field generator 2 corresponding to each selected guidance area. FIG. 11 is a diagram showing a table T2 that shows magnetic fields generated in each guidance area when the guidance area to which the capsule endoscope 10 is guided is selected and there is no information for the magnetic guidance in the operation input unit.

When the water surface area is selected as the guidance area, under the controls of the magnetic field control instruction unit 45 and the magnetic field controller 8, the magnetic field generator 2 generates the vertical direction gradient magnetic field having a gradient in the vertical direction, and as shown in table T2 in FIG. 11, the magnetic field generator 2 generates an upward magnetic field gradient with respect to the vertical axis so that a resultant force of the buoyancy, the gravity force of the capsule endoscope 10, and a magnetic attracting force generated by the magnetic field gradient has a strength in the upward direction with respect to the vertical axis. In this way, the magnetic field generator 2 generates a magnetic field for trapping (pressing) the capsule endoscope 10 on the water surface Ws or an upper portion of the stomach wall. As a result, the capsule endoscope 10 is located on the water surface Ws or an upper portion of the stomach wall.

When the underwater area is selected as the guidance area, under the controls of the magnetic field control instruction unit 45 and the magnetic field controller 8, the magnetic field generator 2 generates the uniform gradient magnetic field in the vertical direction, and as shown in table T2 in FIG. 11, the magnetic field generator 2 generates an upward magnetic field gradient with respect to the vertical axis so that the gravity force and the buoyancy of the capsule endoscope 10 and the magnetic attracting force in the vertical direction are approximately balanced. In this way, the magnetic field generator 2 causes the capsule endoscope 10 to generate a magnetic force to suspend the capsule endoscope 10 under the water. As a result, the capsule endoscope 10 is located under the water.

When the water bottom area is selected as the guidance area, under the controls of the magnetic field control instruction unit 45 and the magnetic field controller 8, the magnetic field generator 2 generates the uniform gradient magnetic field in the vertical direction, and as shown in table T2 in FIG. 11, the magnetic field generator 2 generates a downward magnetic field gradient with respect to the vertical axis so that a resultant force of the buoyancy, the gravity force of the capsule endoscope 10, and the magnetic attracting force has a strength in the downward direction with respect to the vertical axis. In this way, the magnetic field generator 2 generates a magnetic field for trapping (pressing) the capsule endoscope 10 on the stomach wall in the water bottom area. As a result, the capsule endoscope 10 is located on the water bottom.

In this way, by applying a magnetic field having a strength and a direction suited to each guidance area to the permanent magnet 19, it is possible to automatically correctly locate the capsule endoscope 10 in the selected guidance area even when the operation information for magnetically guiding the capsule endoscope 10 is not input from the input unit 6. Therefore, the operation input processing by an operator to maintain the capsule endoscope 10 in each guidance area is not required, so that the operability is improved.

Figure 12A:
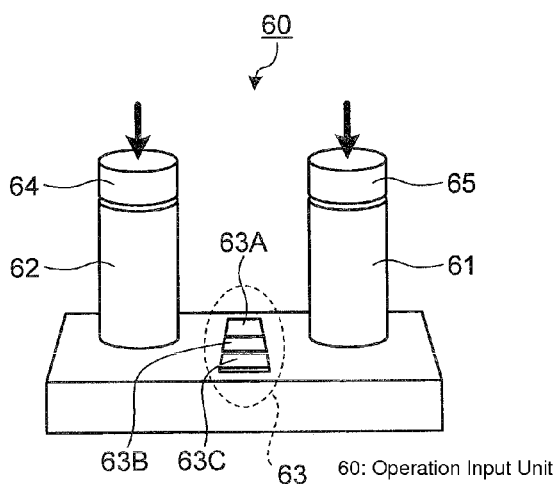
FIG. 12A is a front view showing the operation input unit included in an input unit shown in FIG. 1.
Figure 12B:
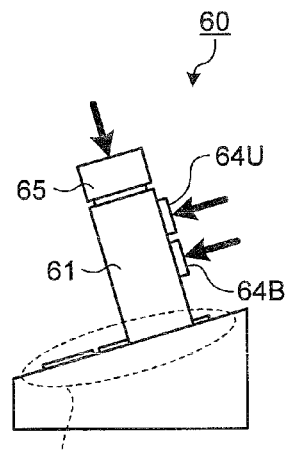
FIG. 12B is a right side view of the operation input unit shown in FIG. 12A.

Next, what magnetic field is applied to the permanent magnet 19 and how the capsule endoscope 10 moves by the operation of the operation input unit will be described. First, the operation input unit for operating the magnetic guidance of the capsule endoscope 10 will be described. FIGS. 12A and 12B are schematic diagrams showing an example of the operation input unit included in the input unit 6 shown in FIG. 1. FIG. 12A is a front view of the operation input unit and FIG. 12B is a right side view of the operation input unit.

As shown in FIG. 12A, an operation input unit 60 includes two joysticks 61 and 62 for three-dimensionally operating the magnetic guidance of the capsule endoscope 10 by the magnetic field generator 2. The joysticks 61 and 62 are capable of a tilt operation in the vertical direction and the horizontal direction.

The operation input unit 60 includes a guidance area switching unit 63 having a water surface switch 63A, an underwater switch 63B, and a water bottom switch 63C. When pressing the water surface switch 63A, the water surface switch 63A inputs selection information for selecting the water surface area as the guidance area into the external control unit 4. When pressing the underwater switch 63B, the underwater switch 63B inputs selection information for selecting the underwater area as the guidance area into the external control unit 4. When pressing the water bottom switch 63C, the water bottom switch 63C inputs selection information for selecting the water bottom area as the guidance area into the external control unit 4.

As shown in FIG. 12B, the joystick 61 has an up button 64U and a down button 64B on the rear surface thereof. When pressing the up button 64U, the up button 64U inputs operation information for instructing an upward guidance of the capsule endoscope 10 into the external control unit 4. When pressing the down button 64B, the down button 64B inputs operation information for instructing a downward guidance of the capsule endoscope 10 into the external control unit 4. The joystick 62 has an approach button 64 on the top thereof. When pressing the approach button 64, the approach button 64 inputs operation information for guiding the capsule endoscope 10 so that the imaging unit 11A of the capsule endoscope 10 approaches an imaging object of the imaging unit 11A into the external control unit 4. The joystick 61 has a capture button 65 on the top thereof. When pressing the capture button 65, the capture button 65 captures an in-vivo image displayed on the display unit 5.

Figure 13A:
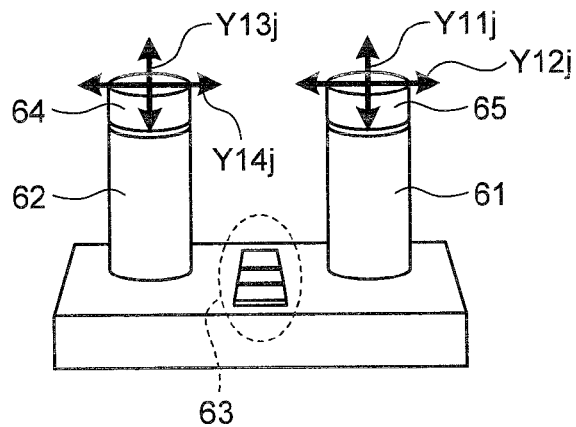
FIG. 13A is a front view of the operation input unit for explaining the magnetic guidance of the capsule medical device, which can be operated by the operation input unit, in a water surface area.
Figure 13B:
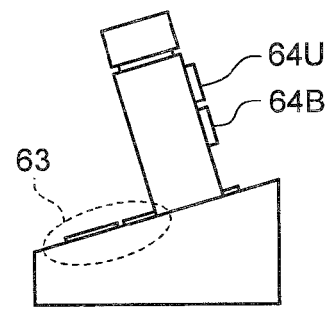
FIG. 13B is a right side view of the operation input unit for explaining the magnetic guidance of the capsule medical device, which can be operated by the operation input unit, in the water surface area.
Figure 13C:
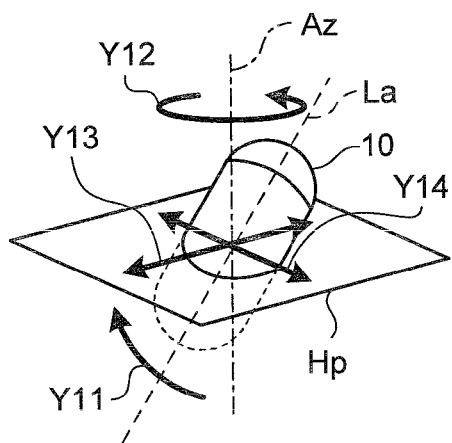
FIG. 13C is a diagram showing movements of the capsule endoscope instructed by operations of each constituent unit of the operation input unit.

Next, operations of each constituent unit of the operation input unit 60 by an operator and magnetic fields generated by the magnetic field generator 2 responding to each operation will be described. First, a case in which the water surface area is selected will be described. FIGS. 13A to 13C are diagrams for explaining the magnetic guidance of the capsule medical device, which can be operated by the operation input unit 60, in the water surface area. FIG. 13A is a front view of the operation input unit 60. FIG. 13B is a right side view of the operation input unit 60. FIG. 13C is a diagram showing the movements of the capsule endoscope 10 instructed by operations of each constituent unit of the operation input unit 60.

First, as shown in FIG. 13A, the tilt direction in the vertical direction of the joystick 61 shown by the arrow Y11*j* corresponds to a direction of a tilting operation in which the distal end of the capsule endoscope 10 oscillates through the vertical axis Az as shown by the arrow Y11 in FIG. 13C. When the operation input unit 60 inputs operation information corresponding to the tilt operation of the joystick 61 shown by the arrow Y11*j* into the external control unit 4, on the basis of the operation information, the magnetic field control instruction unit 45 calculates a guidance direction of the distal end of the capsule endoscope 10 on the absolute coordinate system in accordance with the tilt direction of the joystick 61 and calculates a guidance speed in accordance with the tilt operation of the joystick 61. The magnetic field control instruction unit 45 selects the peak magnetic field switched by the magnetic field condition switching unit 46 as an applied magnetic field, causes the magnetic field generator 2 to generate the peak magnetic field in a direction corresponding to the calculated guidance direction, and changes the angle between the direction of the peak magnetic field and the vertical axis Az in a vertical plane including the vertical axis Az and the long axis La of the capsule endoscope 10 at the calculated guidance speed.

As shown in FIG. 13A, the tilt direction in the horizontal direction of the joystick 61 shown by the arrow Y12*j* corresponds to a direction of a rotation operation in which the capsule endoscope 10 rotates around the vertical axis Az as shown by the arrow Y12 in FIG. 13C. When the operation input unit 60 inputs operation information corresponding to the tilt operation of the joystick 61 shown by the arrow Y12*j* into the external control unit 4, on the basis of the operation information, the magnetic field control instruction unit 45 calculates a guidance direction of the distal end of the capsule endoscope 10 on the absolute coordinate system in accordance with the tilt direction of the joystick 61, calculates a guidance speed in accordance with the tilt operation of the joystick 61, causes the magnetic field generator 2 to generate the peak magnetic field in a direction corresponding to the calculated guidance direction, and rotates the direction of the peak magnetic field around the vertical axis Az at the calculated guidance speed.

As shown in FIG. 13A, the tilt direction in the vertical direction of the joystick 62 shown by the arrow Y13*j* corresponds to a horizontal backward operation direction or a horizontal forward operation direction in which the capsule endoscope 10 moves in a direction indicated by a line obtained by projecting the long axis La of the capsule endoscope 10 to the horizontal plane Hp as shown by the arrow Y13 in FIG. 13C. When the operation input unit 60 inputs operation information corresponding to the tilt operation of the joystick 62 shown by the arrow Y13*j* into the external control unit 4, on the basis of the operation information, the magnetic field control instruction unit 45 calculates a guidance direction and a guidance position of the distal end of the capsule endoscope 10 on the absolute coordinate system in accordance with the tilt direction of the joystick 62, calculates a guidance speed in accordance with the tilt operation of the joystick 62, causes the magnetic field generator 2 to generate the peak magnetic field in a direction corresponding to the calculated guidance direction, and moves the peak of the peak magnetic field to the guidance position at the calculated guidance speed.

As shown in FIG. 13A, the tilt direction in the horizontal direction of the joystick 62 shown by the arrow Y14*j* corresponds to a horizontal right operation direction or a horizontal left operation direction in which the capsule endoscope 10 moves perpendicular to a direction indicated by a line obtained by projecting the long axis La of the capsule endoscope 10 to the horizontal plane Hp as shown by the arrow Y14 in FIG. 13C. When the operation input unit 60 inputs operation information corresponding to the tilt operation of the joystick 62 shown by the arrow Y14*j* into the external control unit 4, on the basis of the operation information, the magnetic field control instruction unit 45 calculates a guidance direction and a guidance position of the distal end of the capsule endoscope 10 on the absolute coordinate system in accordance with the tilt direction of the joystick 62, calculates a guidance speed in accordance with the tilt operation of the joystick 62, causes the magnetic field generator 2 to generate the peak magnetic field in a direction corresponding to the calculated guidance direction, and moves the peak of the peak magnetic field to the guidance position at the calculated guidance speed.

In this way, when the water surface area is selected as the guidance area, the guidance operations for guiding the capsule endoscope 10 are set according to each operation of the operation input unit 60 so that the capsule endoscope 10 can be guided along the water surface. In the water surface area, it is set that the up button 64U is not used because the capsule endoscope 10 cannot be guided further upward.

Figure 14A:
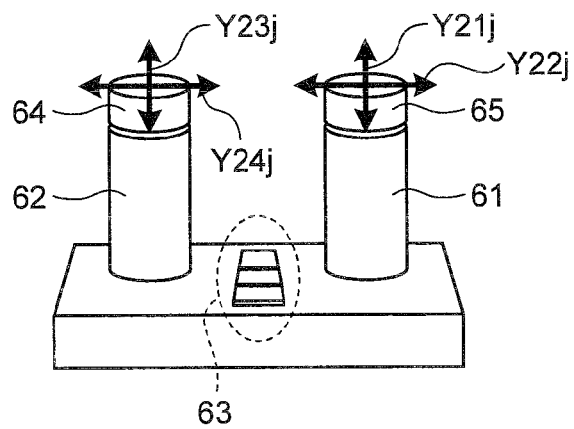
FIG. 14A is a front view of the operation input unit for explaining the magnetic guidance of the capsule medical device, which can be operated by the operation input unit, in an underwater area.
Figure 14B:
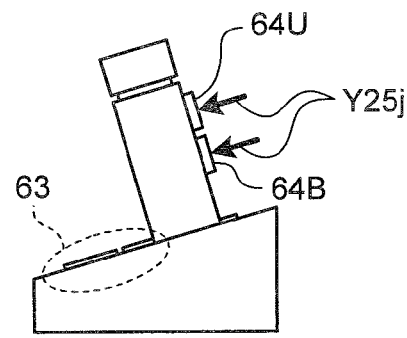
FIG. 14B is a right side view of the operation input unit for explaining the magnetic guidance of the capsule medical device, which can be operated by the operation input unit, in the underwater area.
Figure 14C:
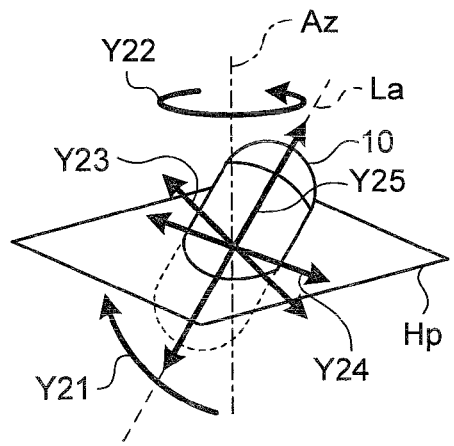
FIG. 14C is a diagram showing the movements of the capsule endoscope instructed by operations of each constituent unit of the operation input unit.

Next, a case in which the underwater area is selected will be described. FIGS. 14A to 14C are diagrams for explaining the magnetic guidance of the capsule medical device, which can be operated by the operation input unit 60, in the underwater area. FIG. 14A is a front view of the operation input unit 60. FIG. 14B is a right side view of the operation input unit 60. FIG. 14C is a diagram showing the movements of the capsule endoscope 10 instructed by operations of each constituent unit of the operation input unit 60.

First, as shown in FIG. 14A, the tilt direction in the vertical direction of the joystick 61 shown by the arrow Y21*j* corresponds to a direction of a tilting operation of the capsule endoscope 10 shown by the arrow Y21 in FIG. 14C. When the operation input unit 60 inputs operation information corresponding to the tilt operation of the joystick 61 shown by the arrow Y21*j* into the external control unit 4, on the basis of the operation information, the magnetic field control instruction unit 45 calculates a guidance direction of the distal end of the capsule endoscope 10 on the absolute coordinate system in accordance with the tilt direction of the joystick 61 and calculates a guidance speed in accordance with the tilt operation of the joystick 61. The magnetic field control instruction unit 45 selects the uniform gradient magnetic field and the uniform magnetic field switched by the magnetic field condition switching unit 46 as applied magnetic fields, causes the magnetic field generator 2 to generate the uniform magnetic field in a direction corresponding to the calculated guidance direction, and changes the angles between the direction of the uniform magnetic field, the vertical axis Az, and the long axis La of the capsule endoscope 10 in a vertical plane including the vertical axis Az at the calculated guidance speed.

As shown in FIG. 14A, the tilt direction in the horizontal direction of the joystick 61 shown by the arrow Y22*j* corresponds to a direction of a rotation guidance of the capsule endoscope 10 shown by the arrow Y22 in FIG. 14C. When the operation input unit 60 inputs operation information corresponding to the tilt operation of the joystick 61 shown by the arrow Y22*j* into the external control unit 4, on the basis of the operation information, the magnetic field control instruction unit 45 calculates a guidance direction of the distal end of the capsule endoscope 10 on the absolute coordinate system in accordance with the tilt direction of the joystick 61, calculates a guidance speed in accordance with the tilt operation of the joystick 61, causes the magnetic field generator 2 to generate the uniform magnetic field in a direction corresponding to the calculated guidance direction, and rotates the direction of the uniform magnetic field around the vertical axis Az at the calculated guidance speed.

As shown in FIG. 14A, the tilt direction in the vertical direction of the joystick 62 shown by the arrow Y23*j* corresponds to a down operation direction or an up operation direction in which the capsule endoscope 10 moves in a direction indicated by the arrow Y23 in a plane perpendicular to the long axis La of the capsule endoscope 10 shown in FIG. 14C. When the operation input unit 60 inputs operation information corresponding to the tilt operation of the joystick 62 shown by the arrow Y23*j* into the external control unit 4, on the basis of the operation information, the magnetic field control instruction unit 45 calculates an operation direction of the distal end of the capsule endoscope 10 on the absolute coordinate system in accordance with the tilt direction of the joystick 62, calculates an operation speed in accordance with the tilt operation of the joystick 62, and causes the magnetic field generator 2 to generate the uniform gradient magnetic field having a gradient whose direction corresponds to the calculated operation direction and which corresponds to the calculated operation speed.

As shown in FIG. 14A, the tilt direction in the horizontal direction of the joystick 62 shown by the arrow Y24*j* corresponds to a right operation direction or a left operation direction in which the capsule endoscope 10 moves in a direction indicated by the arrow Y24 in a plane perpendicular to the long axis La of the capsule endoscope 10 shown in FIG. 14C. When the operation input unit 60 inputs operation information corresponding to the tilt operation of the joystick 62 shown by the arrow Y24*j* into the external control unit 4, on the basis of the operation information, the magnetic field control instruction unit 45 calculates an operation direction of the distal end of the capsule endoscope 10 on the absolute coordinate system in accordance with the tilt direction of the joystick 62, calculates an operation speed in accordance with the tilt operation of the joystick 61, and causes the magnetic field generator 2 to generate the uniform gradient magnetic field having a gradient whose direction corresponds to the calculated operation direction and which corresponds to the calculated operation speed.

Further, as shown in FIG. 14B, when pressing the up button 64U or the down button 64B as shown by the arrow Y25*j*, the up button 64U or the down button 64B instructs a forward operation direction or a backward operation direction in which the imaging elements 15A and 15B move forward or backward as shown by the arrow Y25 along the long axis La of the capsule endoscope 10 shown in FIG. 14C. When the operation input unit 60 inputs operation information corresponding to the pressing operation of the up button 64U or the down button 64B shown by the arrow Y25*j* into the external control unit 4, on the basis of the operation information, the magnetic field control instruction unit 45 calculates an operation direction of the distal end of the capsule endoscope 10 on the absolute coordinate system according to which button is pressed, and causes the magnetic field generator 2 to generate the uniform gradient magnetic field having a gradient along the long axis La according to the calculated operation direction.

Figure 15:
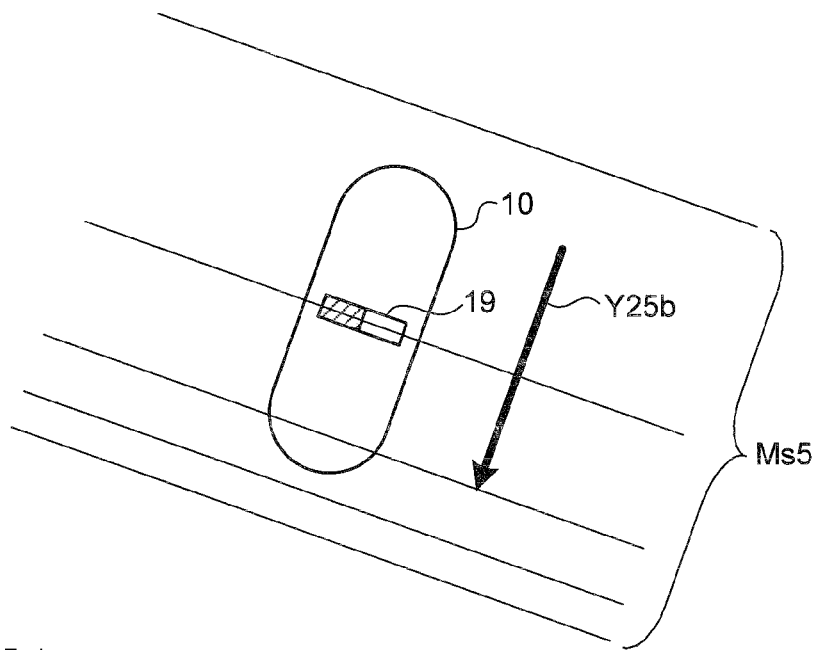
FIG. 15 is a diagram for explaining an example of the uniform gradient magnetic field generated by the magnetic field generator shown in FIG. 1.
Figure 16:
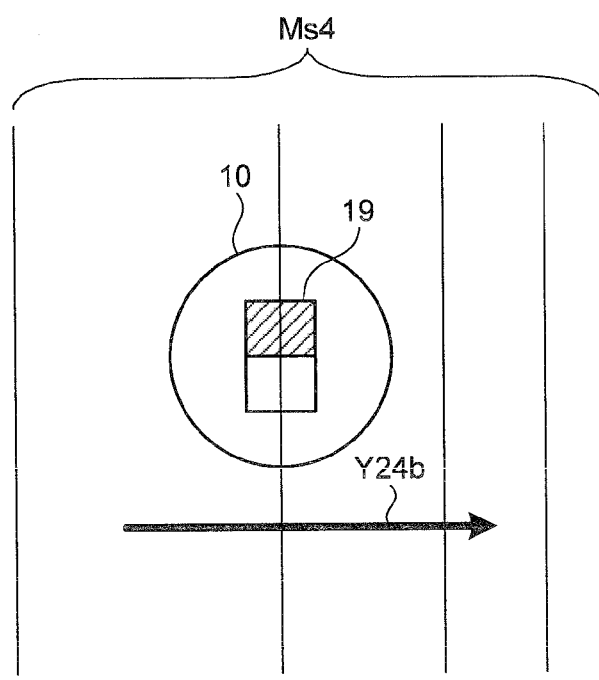
FIG. 16 is a diagram for explaining an example of the uniform gradient magnetic field generated by the magnetic field generator shown in FIG. 1.
Figure 17:
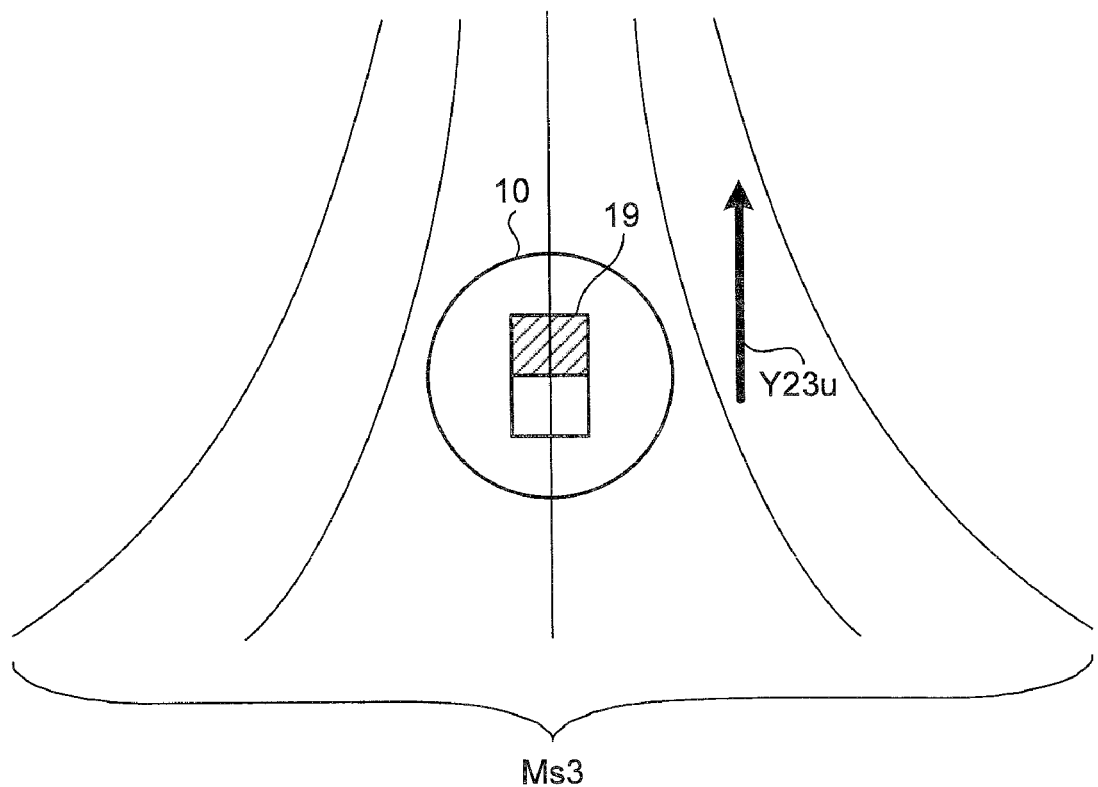
FIG. 17 is a diagram for explaining an example of the uniform gradient magnetic field generated by the magnetic field generator shown in FIG. 1.

Specifically, when the down button 64B is pressed, as shown in FIG. 15, the magnetic field generator 2 generates a uniform gradient magnetic field Ms5 having a gradient in which the density of the magnetic field increases in the downward direction of the long axis La of the capsule endoscope 10, and thereby moves the capsule endoscope 10 downward along the long axis La of the capsule endoscope 10 as shown by the arrow Y25*b*. When the joystick 62 is operated and a right operation is input, as shown in FIG. 16, if a plane perpendicular to the long axis La of the capsule endoscope 10 is seen from below, the magnetic field generator 2 generates a uniform gradient magnetic field Ms4 in which the density of the magnetic field in parallel with the magnetization direction of the permanent magnet 19 increases in the right direction, and thereby moves the capsule endoscope 10 in the right direction of the plane perpendicular to the long axis La of the capsule endoscope 10 as shown by the arrow Y24*b*. When the joystick 62 is operated and an up operation is input, as shown in FIG. 17, if a plane perpendicular to the long axis La of the capsule endoscope 10 is seen from below, the magnetic field generator 2 generates a uniform gradient magnetic field Ms3 in which the density of the magnetic field in parallel with the magnetization direction of the permanent magnet 19 increases in the upward direction, and thereby moves the capsule endoscope 10 in the upward direction of the plane perpendicular to the long axis La of the capsule endoscope 10 as shown by the arrow Y23*u*.

In this way, when the underwater area is selected as the guidance area, each operation of the operation input unit 60 is set in association with the guidance operations of the capsule endoscope 10 so that the capsule endoscope 10 can be guided along the plane perpendicular to the long axis of the capsule endoscope 10 instead of the water surface. That is to say, it is set that the capsule endoscope 10 can be guided along the imaging surfaces of the imaging units 11A and 11B. In other words, the capsule endoscope 10 is guided to move in the left, right, up, and down directions with respect to an image. Therefore, an operator can guide the capsule endoscope 10 as if the operator actually observed the inside of the stomach with his or her own eyes, so that it is possible to implement a more intuitive guidance. When the underwater area is selected as the guidance area, the capsule endoscope 10 can be guided upward and downward along the long axis La of the capsule endoscope 10 in the water, so that it is possible to observe an observation object while approaching the object or moving away from the object.

Figure 18A:
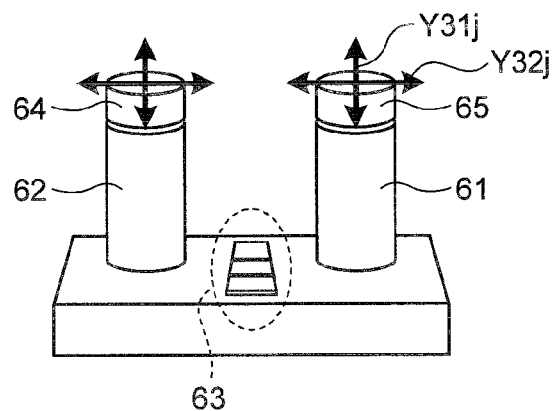
FIG. 18A is a front view of the operation input unit for explaining the magnetic guidance of the capsule medical device, which can be operated by the operation input unit, in a water bottom area.
Figure 18B:
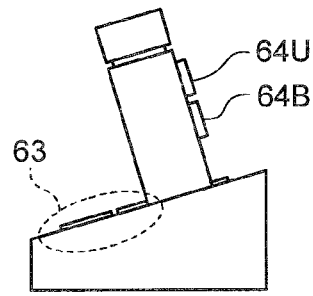
FIG. 18B is a right side view of the operation input unit for explaining the magnetic guidance of the capsule medical device, which can be operated by the operation input unit, in the water bottom area.
Figure 18C:
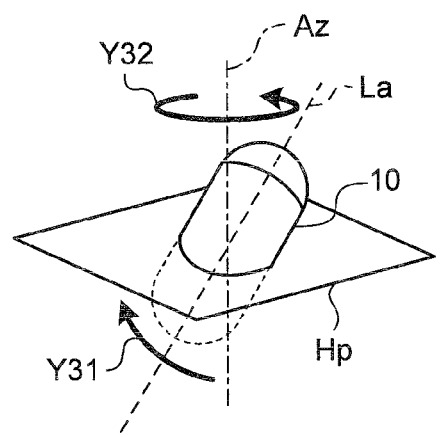
FIG. 18C is a diagram showing the movements of the capsule endoscope instructed by operations of each constituent unit of the operation input unit.

Next, a case in which the water bottom area is selected will be described. FIGS. 18A to 18C are diagrams for explaining the magnetic guidance of the capsule medical device, which can be operated by the operation input unit 60, in the water bottom area. FIG. 18A is a front view of the operation input unit 60. FIG. 18B is a right side view of the operation input unit 60. FIG. 18C is a diagram showing the movements of the capsule endoscope 10 instructed by operations of each constituent unit of the operation input unit 60.

First, as shown in FIG. 18A, the tilt direction in the vertical direction of the joystick 61 shown by the arrow Y31*j* corresponds to a direction of a tilting operation of the capsule endoscope 10 shown by the arrow Y31 in FIG. 18C. When the operation input unit 60 inputs operation information corresponding to the tilt operation of the joystick 61 shown by the arrow Y31*j* into the external control unit 4, on the basis of the operation information, the magnetic field control instruction unit 45 calculates a guidance direction of the distal end of the capsule endoscope 10 on the absolute coordinate system in accordance with the tilt direction of the joystick 61 and calculates a guidance speed in accordance with the tilt operation of the joystick 61. The magnetic field control instruction unit 45 selects the uniform gradient magnetic field and the uniform magnetic field switched by the magnetic field condition switching unit 46 as applied magnetic fields, causes the magnetic field generator 2 to generate the uniform magnetic field in a direction corresponding to the calculated guidance direction, and changes the angles between the direction of the uniform magnetic field, the vertical axis Az, and the long axis La of the capsule endoscope 10 in a vertical plane including the vertical axis Az at the calculated guidance speed.

As shown in FIG. 18A, the tilt direction in the horizontal direction of the joystick 61 shown by the arrow Y32$j$ corresponds to a direction of a rotation guidance of the capsule endoscope 10 shown by the arrow Y32 in FIG. 18C. When the operation input unit 60 inputs operation information corresponding to the tilt operation of the joystick 61 shown by the arrow Y32$j$ into the external control unit 4, on the basis of the operation information, the magnetic field control instruction unit 45 calculates a guidance direction of the distal end of the capsule endoscope 10 on the absolute coordinate system in accordance with the tilt direction of the joystick 61, calculates a guidance speed in accordance with the tilt operation of the joystick 61, causes the magnetic field generator 2 to generate the uniform magnetic field in a direction corresponding to the calculated guidance direction, and rotates the direction of the uniform magnetic field around the vertical axis Az at the calculated guidance speed.

In this way, when the water bottom area is selected as the guidance area, the tilting operation and the rotation operation are set so that the water bottom, that is, the stomach wall St can be observed in detail. In the water surface area, the up operation and the backward operation, in which the capsule endoscope 10 moves away from the surface of the stomach wall, are not set so that the surface of the stomach wall can be observed in detail. It is often difficult to move the capsule endoscope 10 along the surface of the stomach wall due to the friction with the surface of the stomach wall and the shape of the surface of the stomach wall, so that the forward operation, the right operation, and the left operation are not set either. The down operation is not set either because the capsule endoscope 10 cannot be guided further downward. Therefore, it is set that the joystick 62, the up button 64U, and the down button 64B are not used.

As described above, in the first embodiment, the guidance of the capsule endoscope 10 suitable for each guidance area can be implemented by changing the relationship between the operation input unit 60 and the moving directions of the capsule endoscope 10 in accordance with each guidance area. Specifically, in the first embodiment, the guidance of the capsule endoscope 10 suitable for each guidance area can be implemented by changing the type of the magnetic field, and the amplitude and the direction of the magnetic field gradient generated in the guidance direction of the capsule endoscope 10 and the vertical direction in accordance with each guidance area.

Figure 19:
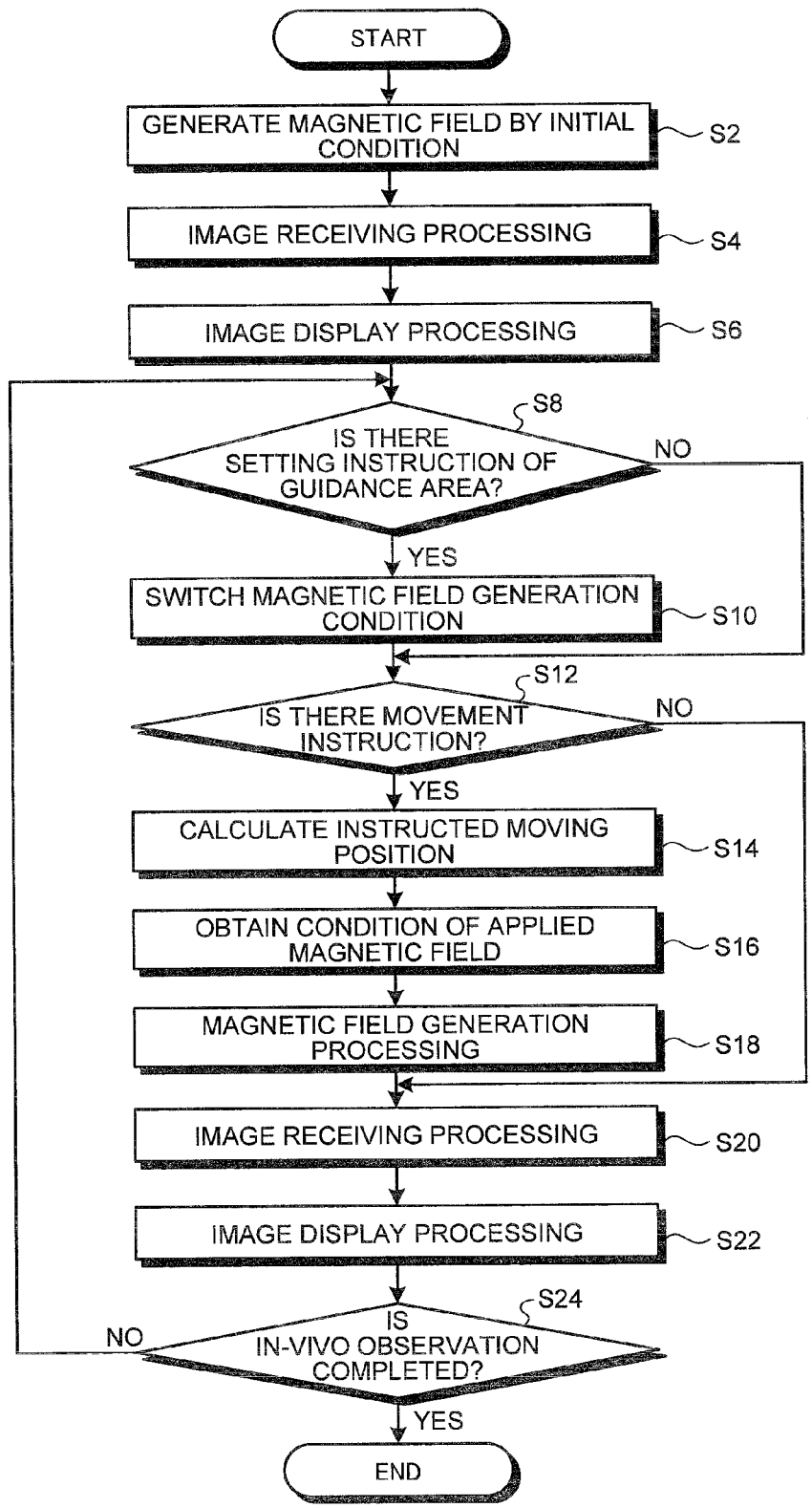
FIG. 19 is a flowchart showing a processing procedure of guidance processing of the capsule endoscope of the capsule medical device guidance system shown in FIG. 1.

Next, the guidance processing of the capsule endoscope 10 of the capsule medical device guidance system 1 will be described. FIG. 19 is a flowchart showing a processing procedure of the guidance processing of the capsule endoscope 10 of the capsule medical device guidance system 1 shown in FIG. 1.

As shown in FIG. 19, when the input unit 6 inputs instruction information for instructing a start of in-vivo observation, the magnetic field control instruction unit 45 transmits instruction information to the magnetic field controller 8 to generate a magnetic field by an initial condition (step S2). For example, the magnetic field control instruction unit 45 causes the magnetic field generator 2 to generate the peak magnetic field having the peak in the center of the magnetic field generation area as the initial condition. In this case, it is easy to find the start position of the guidance processing of the capsule endoscope 10, so that operability when stating the guidance operation is improved. When a predetermined button of the input unit 6 is pressed, the magnetic field control instruction unit 45 my cause the magnetic field generator 2 to generate the peak magnetic field having the peak in the center of the magnetic field generation area by this initial condition. Even if the capsule endoscope 10 is out of the trap of the peak magnetic field and cannot be guided successfully, it is easy to restore the position of the capsule endoscope 10 to the initial state, so that operability is improved.

The image receiving unit 41 performs image receiving processing for sequentially obtaining the in-vivo images sequentially received by the transmitting/receiving unit 3 (step S4) and the image display controller 42 performs image display processing for displaying the in-vivo images sequentially received by the transmitting/receiving unit 3 on the display unit 5 (step S6).

In the external control unit 4, the magnetic field condition switching unit 46 determines whether or not there is a setting instruction of the guidance area on the basis of the presence or absence of an input of selection information from the operation input unit 60 (step S8). If the magnetic field condition switching unit 46 determines that there is a setting instruction of the guidance area (step S8: Yes), the magnetic field condition switching unit 46 switches the magnetic field generation condition of the magnetic field generator 2 according to the guidance area selected by the operation input unit 60 from the input selection information (step S10). As described above, for each guidance area, the magnetic field generation condition in which the type of magnetic field, and the amplitude and the direction of the magnetic field gradient generated in the guidance direction of the capsule endoscope 10 and the vertical direction are set is stored in the magnetic field condition storage unit 47. The magnetic field condition switching unit 46 refers to the magnetic field generation condition corresponding to the set guidance area in the magnetic field generation conditions stored in the magnetic field condition storage unit 47 and switches the magnetic field generation condition to the referred magnetic field generation condition. In this case, the operation information is not input from the operation input unit 60, so that the magnetic field control instruction unit 45 causes the magnetic field generator 2 to generate magnetic fields having the magnetic forces shown in table T2 in FIG. 11. Therefore, the capsule endoscope 10 is stably located in the set guidance area. When the guidance area is switched to another guidance area, the capsule endoscope 10 is guided to the switched new guidance area, and stably located in this guidance area.

On the other hand, if the magnetic field condition switching unit 46 determines that there is no setting instruction of the guidance area (step S8: No), or if the magnetic field condition switching unit 46 switches the magnetic field generation condition (step S10), the magnetic field control instruction unit 45 determines whether or not there is a movement instruction of the capsule endoscope 10 on the basis of the presence or absence of an input of operation information from the operation input unit 60 (step S12). If the magnetic field control instruction unit 45 determines that there is a movement instruction of the capsule endoscope 10 (step S12: Yes), the magnetic field control instruction unit 45 calculates the moving position instructed by the operation information from the operation input unit 60 (step S14), and obtains the condition of the magnetic field applied to the permanent magnet 19 of the capsule endoscope 10 on the basis of the magnetic field generation condition corresponding to the guidance area (step S16). Then the magnetic field control instruction unit 45 instructs the magnetic field controller 8 to generate a magnetic field in the obtained condition of the magnetic field, and the magnetic field generator 2 performs magnetic field generation processing for generating a magnetic field in the instructed condition (step S18). As a result, the capsule endoscope 10 is moved in the direction and the position according to the operation processing of the operation input unit 60.

If the magnetic field control instruction unit 45 determines that there is no movement instruction of the capsule endoscope 10 (step S12: No), or the magnetic field generation processing (step S18) is completed, the image receiving unit 41 performs image receiving processing (step S20) and the image display controller 42 performs image display processing (step S22). As a result, the display unit 5 sequentially displays in-vivo images captured by the capsule endoscope 10. There may be a delay time of several hundreds of milliseconds from when the transmitting/receiving unit 3 receives the image of the capsule endoscope 10 to when the display unit 5 displays the image. In this case, if the guidance speed of the capsule endoscope 10 is too fast, the position operation of the capsule endoscope 10 is performed inaccurately with respect to the target position, so that the operability is degraded. Therefore, it is desired that the capsule endoscope 10 is guided at a guidance speed considering the delay time. For example, it is desired that the capsule endoscope 10 is guided at a speed of 10 mm/sec or less.

Next, the external control unit 4 determines whether or not the in-vivo observation is completed on the basis of instruction information input by the input unit 6 (step S24). If the external control unit 4 determines that the in-vivo observation is not completed (step S24: No), the external control unit 4 returns to step S8 to continue the in-vivo observation and determines whether or not there is a setting instruction of the guidance area. If the external control unit 4 determines that the in-vivo observation is completed (step S24: Yes), the external control unit 4 stores the in-vivo images captured by the capsule endoscope 10 into the storage unit 7 by collecting the in-vivo images into one folder, and then ends the in-vivo observation.

In this way, in the first embodiment, the magnetic field generation condition is automatically switched for each guidance area, and the magnetic field is generated in a condition suitable for each guidance area, so that the capsule endoscope 10 can be correctly guided with an easy operation.

In the first embodiment, although an example is described in which the water surface area, the underwater area, and the water bottom area are set as the guidance areas, of course, the guidance areas are not limited to these areas, but a combination of at least two of the water surface area, the underwater area, and the water bottom area may be set as the guidance area. For example, the guidance area may be limited to the water surface area and the water bottom area. Under the water, the capsule endoscope 10 cannot be held correctly at a desired position due to distortion of the uniform magnetic field, and when distortion of the uniform gradient magnetic field is large, the control performance of the magnetic field generator may be degraded. In this case, by limiting the guidance area to the water surface area and the water bottom area, the capsule endoscope 10 can be guided only in stable areas, so that the operability is improved.

In the underwater area, the backward operation, the forward operation, the right operation, and the left operation are described as operations in a plane perpendicular to the long axis La of the capsule endoscope 10 shown in FIG. 14C, however they are not limited to these. The backward operation, the forward operation, the right operation, and the left operation in the underwater area may be set as moving operations on the horizontal plane Hp in the same manner as the horizontal backward operation, the horizontal forward operation, the horizontal right operation, and the horizontal left operation on the water surface area.

Figure 20A:
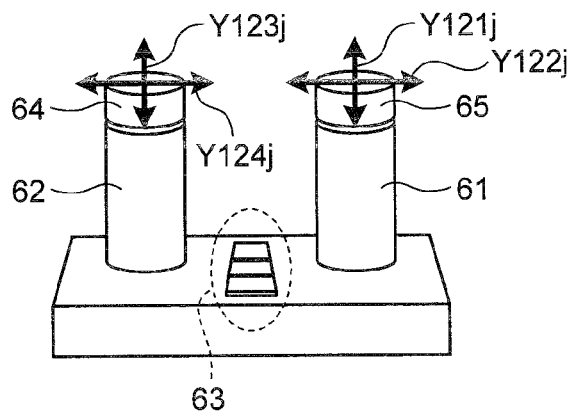
FIG. 20A is a front view of the operation input unit for explaining another example of the magnetic guidance of the capsule medical device, which can be operated by the operation input unit, in the underwater area.

Specifically, as shown in FIG. 20A, when the operation input unit 60 inputs operation information corresponding to the tilt operation of the joystick 62 shown by the arrow Y123*j* into the external control unit 4, on the basis of the operation information, the magnetic field control instruction unit 45 causes the magnetic field generator 2 to generate the uniform magnetic field or the uniform gradient magnetic field so that the capsule endoscope 10 moves as shown by the arrow Y123 (see FIG. 20C) on the horizontal plane Hp. Also, as shown in FIG. 20A, when the operation input unit 60 inputs operation information corresponding to the tilt operation of the joystick 62 shown by the arrow Y124*j* into the external control unit 4, on the basis of the operation information, the magnetic field control instruction unit 45 causes the magnetic field generator 2 to generate the uniform magnetic field or the uniform gradient magnetic field so that the capsule endoscope 10 moves as shown by the arrow Y124 (see FIG. 20C) on the horizontal plane Hp.

Figure 20B:
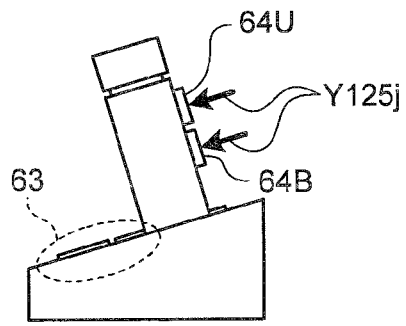
FIG. 20B is a right side view of the operation input unit for explaining another example of the magnetic guidance of the capsule medical device, which can be operated by the operation input unit, in the underwater area.
Figure 20C:
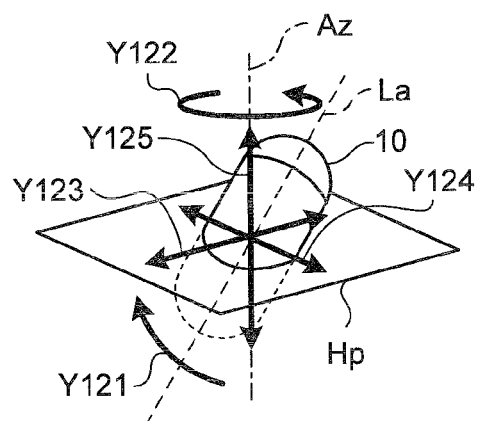
FIG. 20C is a diagram showing the movements of the capsule endoscope instructed by operations of each constituent unit of the operation input unit.

In the underwater area, the up operation and the down operation may be set as moving operations to move upward or downward along the vertical axis Az. In this case, as shown in FIG. 20B, when the operation input unit 60 inputs operation information corresponding to the pressing operation of the up button 64U or the down button 64B shown by the arrow Y125*j* into the external control unit 4, on the basis of the operation information, the magnetic field control instruction unit 45 causes the magnetic field generator 2 to generate the uniform gradient magnetic field so that the capsule endoscope 10 moves as shown by the arrow Y125 (see FIG. 20C) on the vertical axis Az. As shown by the arrows Y121 and Y122 in FIG. 20C, when the operation input unit 60 inputs operation information corresponding to the tilt operation of the joystick 61 shown by the arrow Y121*j* or operation information corresponding to the tilt operation of the joystick 61 shown by the arrow Y122*j* into the external control unit 4, the magnetic field control instruction unit 45 causes the magnetic field generator 2 to generate the uniform magnetic field whose direction is changed so that the capsule endoscope 10 performs the same tilting operation or the same rotation operation as those shown by the arrows Y121 and Y122 in FIG. 14C.

In this way, when the guidance operations of the capsule endoscope 10 are set so that the differences between the moving directions in the underwater area and the moving directions in the water surface area are small, even if the guidance area is switched, it is possible to continue the guidance of the capsule endoscope 10 without confusion. In this case, the underwater area is not set as the guidance area, so that the capsule endoscope 10 can be guided by using only the peak magnetic field because it is assumed that the capsule endoscope 10 is not guided in the underwater area.

In the water bottom area, although a case in which the right operation and the left operation for moving the capsule endoscope 10 with respect to the horizontal plane are not set is described as an example, of course, it is not limited to this, and it is also possible to change the position of the capsule endoscope 10 on the horizontal plane depending on the condition.

Therefore, in the water bottom area, it is possible to set that the forward operation, the backward operation, the right operation, and the left operation for changing the capsule endoscope 10 on the horizontal plane can be performed.

Figure 21A:
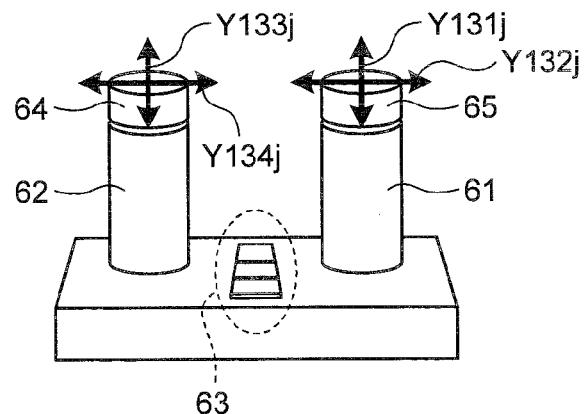
FIG. 21A is a front view of the operation input unit for explaining the magnetic guidance of the capsule medical device, which can be operated by the operation input unit, in the water bottom area.
Figure 21B:
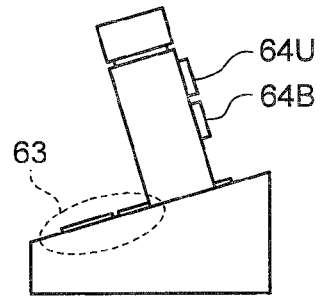
FIG. 21B is a right side view of the operation input unit for explaining the magnetic guidance of the capsule medical device, which can be operated by the operation input unit, in the water bottom area.

Specifically, as shown in FIG. 21A, when the operation input unit 60 inputs operation information corresponding to the tilt operation of the joystick 62 shown by the arrow Y133$j$ into the external control unit 4, on the basis of the operation information, the magnetic field control instruction unit 45 causes the magnetic field generator 2 to generate the uniform magnetic field or the uniform gradient magnetic field so that the capsule endoscope 10 moves as shown by the arrow Y133 (see FIG. 21C) on the horizontal plane Hp. Also, as shown in FIG. 21A, when the operation input unit 60 inputs operation information corresponding to the tilt operation of the joystick 62 shown by the arrow Y134$j$ into the external control unit 4, on the basis of the operation information, the magnetic field control instruction unit 45 causes the magnetic field generator 2 to generate the uniform magnetic field or the uniform gradient magnetic field so that the capsule endoscope 10 moves as shown by the arrow Y134 (see FIG. 21C) on the horizontal plane Hp. FIG. 21B shows a right side view of the operation input unit.

Figure 21C:
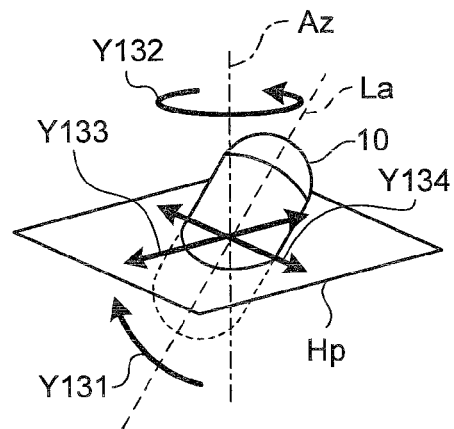
FIG. 21C is a diagram showing the movements of the capsule endoscope instructed by operations of each constituent unit of the operation input unit.

As shown by the arrows Y131 and Y132 in FIG. 21C, when the operation input unit 60 inputs operation information corresponding to the tilt operation of the joystick 61 shown by the arrow Y131$j$ or operation information corresponding to the tilt operation of the joystick 61 shown by the arrow Y132$j$ into the external control unit 4, the magnetic field control instruction unit 45 causes the magnetic field generator 2 to generate the uniform magnetic field whose direction is changed so that the capsule endoscope 10 performs the same tilting operation or the same rotation operation as those shown by the arrows Y131 and Y132 in FIG. 14C. For the forward operation, the backward operation, the right operation, and the left operation for changing the capsule endoscope 10 on the horizontal plane, it is desired to generate the uniform gradient magnetic field that can have a large strength because the capsule endoscope 10 needs to be moved against the friction with the surface of the stomach wall.

In the first embodiment, when moving the capsule endoscope 10 from the water surface area to the underwater area or the water bottom area, a magnetic field having a high strength that can overcome the surface tension of the water surface is generated, and the capsule endoscope 10 is smoothly moved from the water surface area to the underwater area or the water bottom area. A mode for generating the magnetic field having a high strength that can overcome the surface tension of the water surface will be described as a diving mode.

Figure 22:
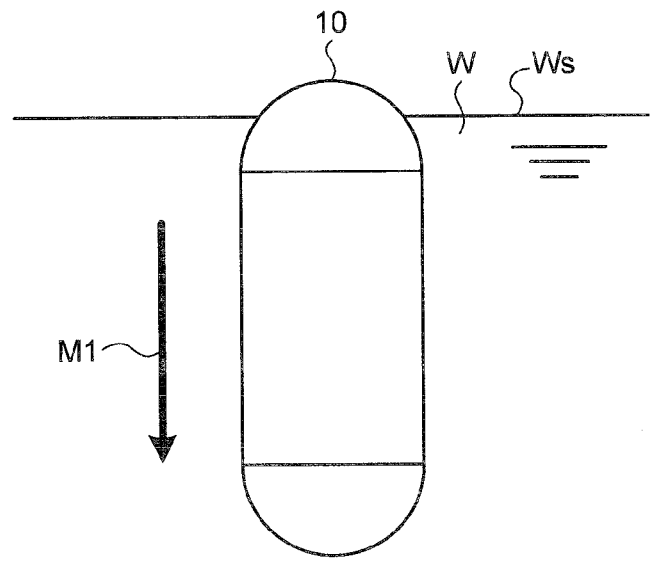
FIG. 22 is a diagram for explaining a diving mode which is an example of the magnetic guidance.
Figure 23:
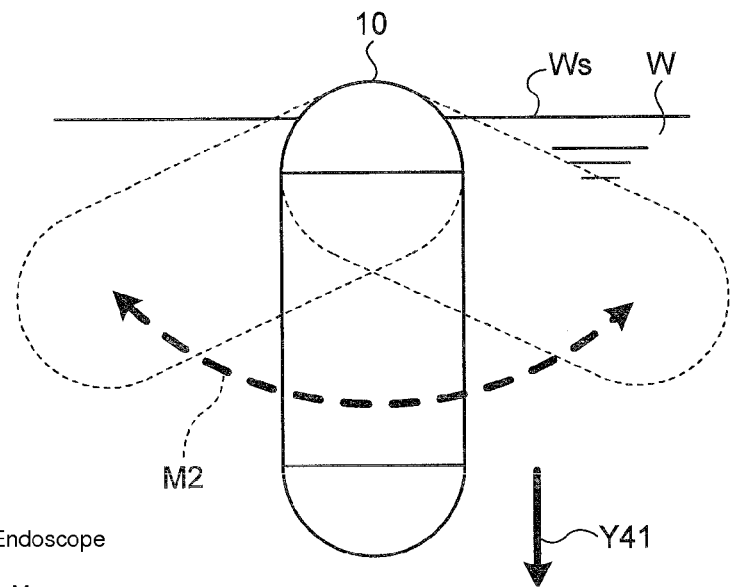
FIG. 23 is a diagram for explaining the diving mode which is an example of the magnetic guidance.

In the diving mode, by the control of the magnetic field generator 2 by the external control unit 4, a strong magnetic field is temporarily generated in the downward direction of the vertical direction and the capsule endoscope 10 is moved from the water surface area to the underwater area or the water bottom area as shown by the arrow M1 in FIG. 22. Also, by the control of the magnetic field generator 2 by the external control unit 4, as shown in FIG. 23, it is possible to generate a magnetic field M2 for causing the capsule endoscope 10 to perform the tilting operation at high speed so as to change the posture of the capsule endoscope 10 at high speed. In this case, by the tilting operation, the water wets the side wall of the capsule endoscope 10 exposed from the water surface, and the effect of the surface tension disappears. Thereafter, by the control of the magnetic field generator 2 by the external control unit 4, a magnetic field for moving the capsule endoscope 10 in the downward direction is generated as shown by the arrow Y41, and thereby the capsule endoscope 10 is moved from the water surface area to the underwater area or the water bottom area. In this method, the capsule endoscope 10 can be guided from the water surface area to the underwater area or the water bottom area even when the strength of the magnetic field is low.

The diving mode is automatically generated when the guidance area is switched from the water surface area to the underwater area or the water bottom area. It is possible to provide a selection button that can select an ON state or an OFF state of the diving mode, and the ON state of the diving mode may be controlled by the operation of the selection button by an operator. When the diving mode is the ON state, if an operation in the vertically downward direction is instructed first, under the control of the external control unit 4, the magnetic field generator 2 generates a magnetic field only once which overcomes the surface tension, and thereafter, the diving mode is automatically becomes the OFF state. Therefore, if the diving mode is the ON state, even when the capsule endoscope 10 moves to the water surface area while the capsule endoscope 10 is guided in the underwater area, the capsule endoscope 10 can be easily returned to the guidance in the underwater area.

In the first embodiment, an approach mode for causing the imaging unit 11A of the capsule endoscope 10 to approach an imaging object is also set. The approach mode is a function to guide the imaging unit 11A of the capsule endoscope 10 in the direction of the long axis La of the capsule endoscope 10, that is, the imaging direction by using the uniform gradient magnetic field.

Figure 24:
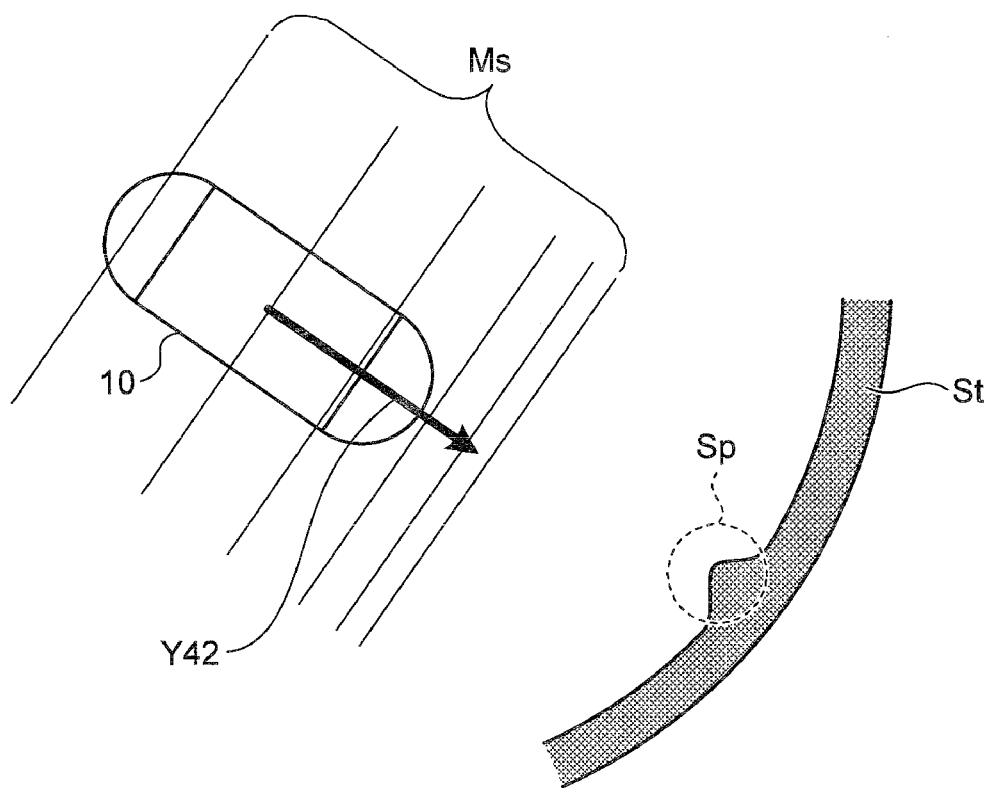
FIG. 24 is a diagram for explaining an approach mode which is an example of the magnetic guidance.

The approach mode becomes the ON state while the approach button 64 of the operation input unit 60 illustrated in FIGS. 12A and 12B is pressed, and becomes the OFF state when the pressing of the approach button 64 is released. For example, a case will be described in which the approach mode becomes the ON state when the capsule endoscope 10 faces downward and captures an image of the imaging object Sp in the water bottom area as shown in FIG. 24.

The magnetic field control instruction unit 45 causes the magnetic field generator 2 to generate the uniform gradient magnetic field Ms having a downward gradient along the long axis La of the capsule endoscope 10 while the approach mode is the ON state. As a result, as shown by the arrow Y42, it is possible to cause the capsule endoscope 10 to approach the imaging object Sp on the stomach wall St whose image is currently captured by the imaging unit 11A. Of course, when the capsule endoscope 10 which faces upward and captures images of the upper stomach wall St is desired to be close to the stomach wall St, the magnetic field control instruction unit 45 causes the magnetic field generator 2 to generate the uniform gradient magnetic field Ms having an upward gradient along the long axis La of the capsule endoscope 10. The imaging direction of the capsule endoscope 10 may be set on the basis of the imaging direction of the imaging unit 11A or the imaging unit 11B which is selected as a basic imaging unit.

Here, operation steps actually performed by an operator will be described. The operator finds the area in which the capsule endoscope 10 is present from the water surface area, the underwater area, and the water bottom area on the basis of the image which is obtained by the capsule endoscope 10 and displayed by the display unit 5. Next, the operator checks whether or not the currently set guidance area matches the area in which the capsule endoscope 10 is present. If the currently set guidance area does not match the area in which the capsule endoscope 10 is present, the operator operates the input unit 6 so that the guidance area matches the area in which the capsule endoscope 10 is present. Thereafter, the operator performs the guidance operation. If the currently set guidance area matches the area in which the capsule endoscope 10 is present, the operator can perform the guidance operation without any change.

When the operator changes the area in which the operator guides the capsule endoscope 10, the operator operates the input unit 6 to change the guidance area to the area in which the operator wants to guide the capsule endoscope 10, and thereby the capsule endoscope 10 moves to the next guidance area. However, when changing the guidance area from the water surface area to the underwater area, an operation for guiding the capsule endoscope 10 from the water surface area to the underwater area by operating the joysticks of the input unit 6 is required.

By the operation steps described above, it is possible to guide the capsule endoscope 10 in a more stable condition while changing the setting of the guidance area.

Second Embodiment

Next, a second embodiment will be described. In the second embodiment, a case will be described in which the area where the capsule endoscope 10 is present is automatically detected from the image of the capsule endoscope 10 and the capsule endoscope 10 is automatically guided to a set guidance area.

Figure 25:
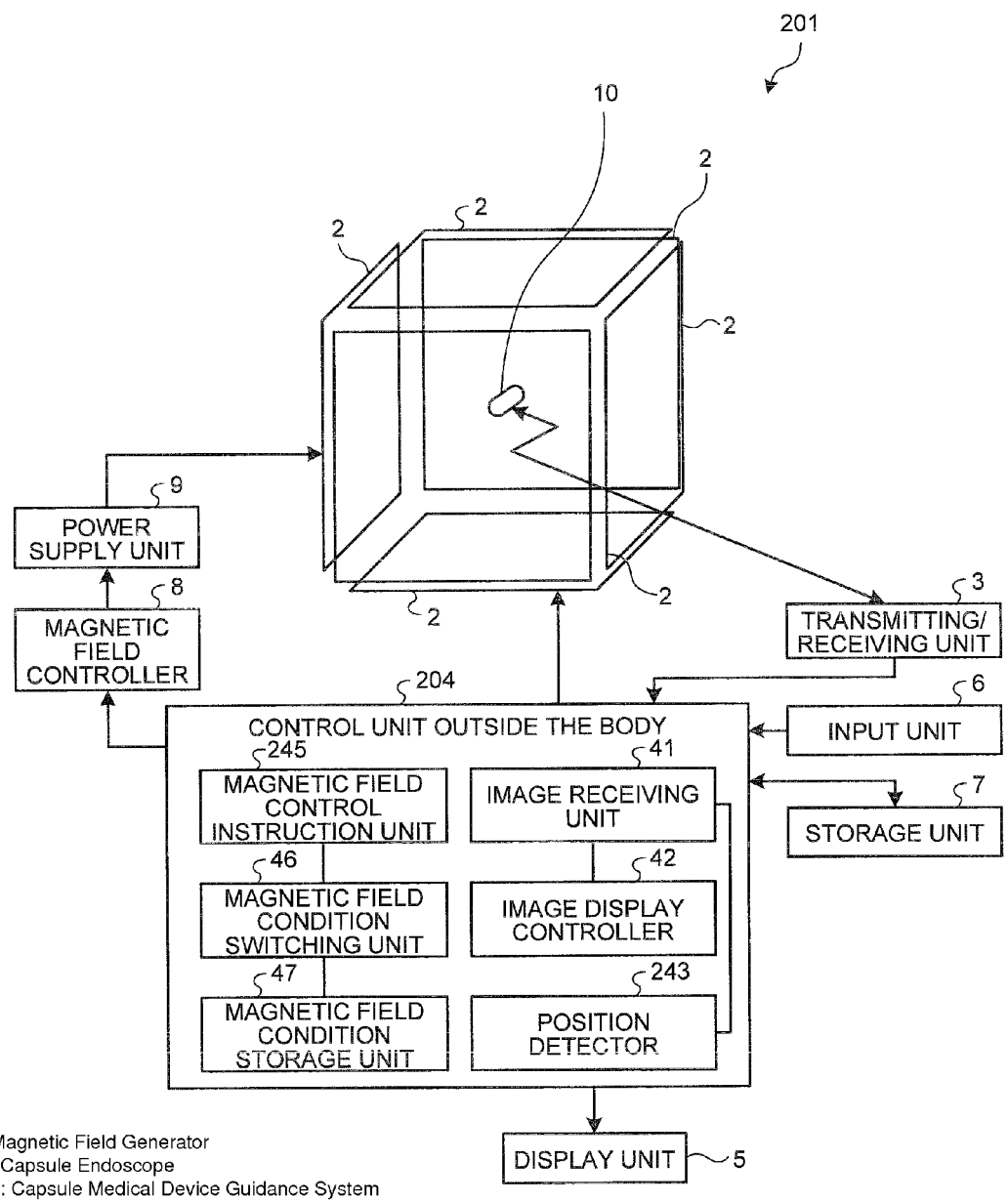
FIG. 25 is a schematic diagram showing an entire configuration of the capsule medical device guidance system according to a second embodiment.

FIG. 25 is a schematic diagram showing an entire configuration of the capsule medical device guidance system according to the second embodiment. As shown in FIG. 25, a capsule medical device guidance system 201 according to the second embodiment has a configuration including an external control unit 204 instead of the external control unit 4 shown in FIG. 1. Compared with the external control unit 4, the external control unit 204 further includes a position detector 243 and includes a magnetic field control instruction unit 245 instead of the magnetic field control instruction unit 45.

The position detector 243 detects in which area of the water surface area, the underwater area, and the water bottom area the capsule endoscope 10 is present from the image captured by the capsule endoscope 10. When the presence area of the capsule endoscope 10 detected by the position detector 243 does not match the guidance area selected by the operation input unit 60 of the input unit 6, the magnetic field control instruction unit 245 causes the magnetic field generator 2 to generate a magnetic field for guiding the capsule endoscope 10 to the guidance area selected by the operation input unit 60.

Figure 26:
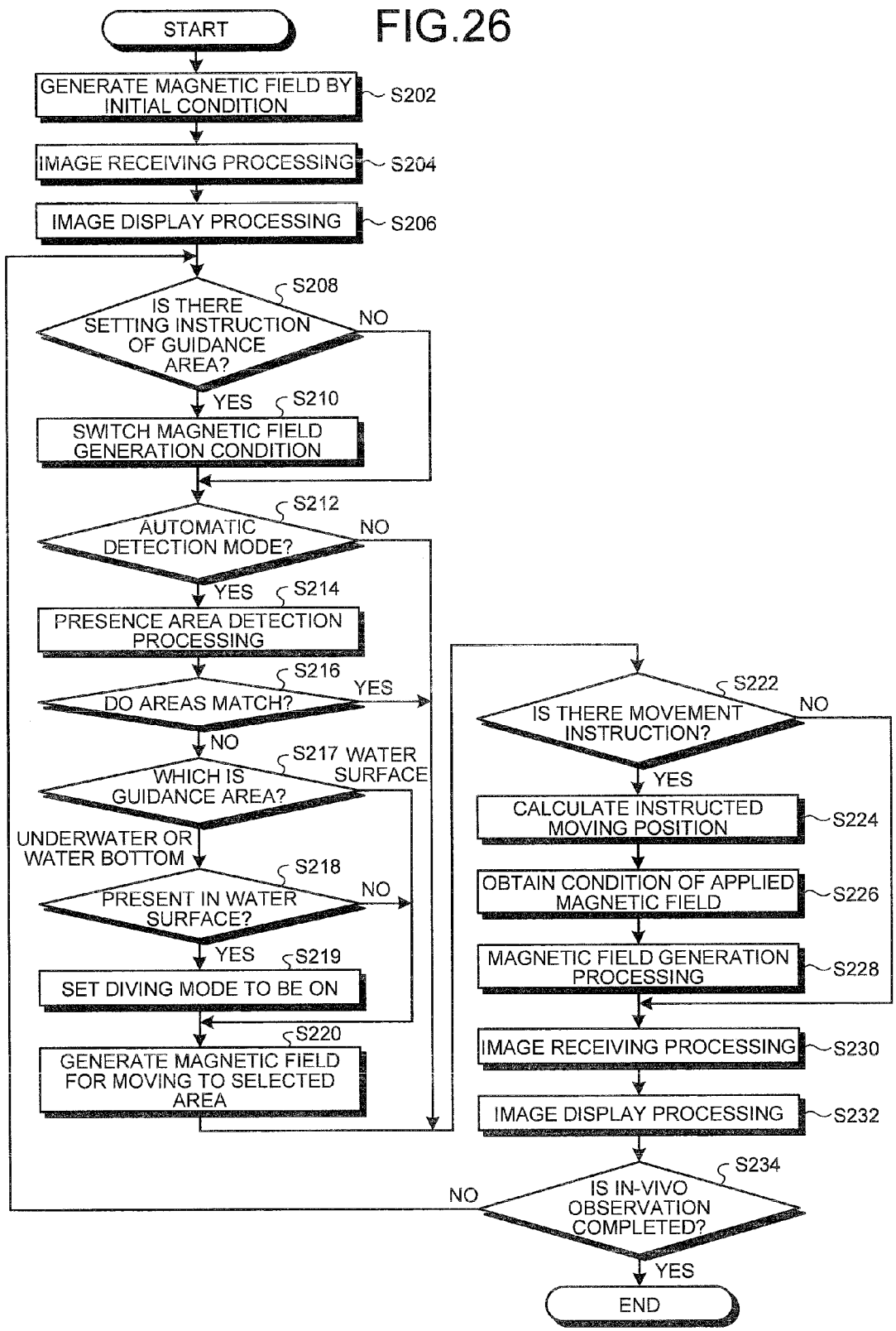
FIG. 26 is a flowchart showing a processing procedure of the guidance processing of the capsule endoscope of the capsule medical device guidance system shown in FIG. 25.

Next, the guidance processing of the capsule endoscope 10 of the capsule medical device guidance system 201 shown in FIG. 25 will be described with reference to FIG. 26. FIG. 26 is a flowchart showing a processing procedure of the guidance processing of the capsule endoscope 10 of the capsule medical device guidance system 201 shown in FIG. 25.

As shown in FIG. 26, first, in the same manner as in step S2 in FIG. 19, when the input unit 6 inputs instruction information for instructing a start of in-vivo observation, the magnetic field control instruction unit 245 transmits instruction information to the magnetic field controller 8 to generate a magnetic field by an initial condition (step S202). Next, in the same manner as in steps S4 and S6 in FIG. 19, the image receiving unit 41 performs image receiving processing (step S204) and the image display controller 42 performs image display processing (step S206).

In the external control unit 204, in the same manner as in step S8 in FIG. 19, the magnetic field condition switching unit 46 determines whether or not there is a setting instruction of the guidance area (step S208). If the magnetic field condition switching unit 46 determines that there is a setting instruction of the guidance area (step S208: Yes), the magnetic field condition switching unit 46 switches the magnetic field generation condition of the magnetic field generator 2 according to the guidance area selected by the operation input unit 60 on the basis of the input selection information (step S210).

Next, if the magnetic field condition switching unit 46 determines that there is no setting instruction of the guidance area (step S208: No), or after the magnetic field generation condition switching processing in step S210 is completed, the external control unit 204 determines whether or not an automatic detection mode for automatically detecting the presence area of the capsule endoscope 10 is set (step S212). If the external control unit 204 determines that the automatic detection mode for automatically detecting the presence area of the capsule endoscope 10 is set (step S212: Yes), the position detector 243 performs presence area detection processing for detecting the presence area of the capsule endoscope 10 (step S214).

The position detector 243 detects the presence area of the capsule endoscope 10 on the basis of whether or not there is an image pattern unique to the water surface or the water bottom from the image that is captured by the capsule endoscope 10 and received by the image receiving unit 41.

Figure 27:
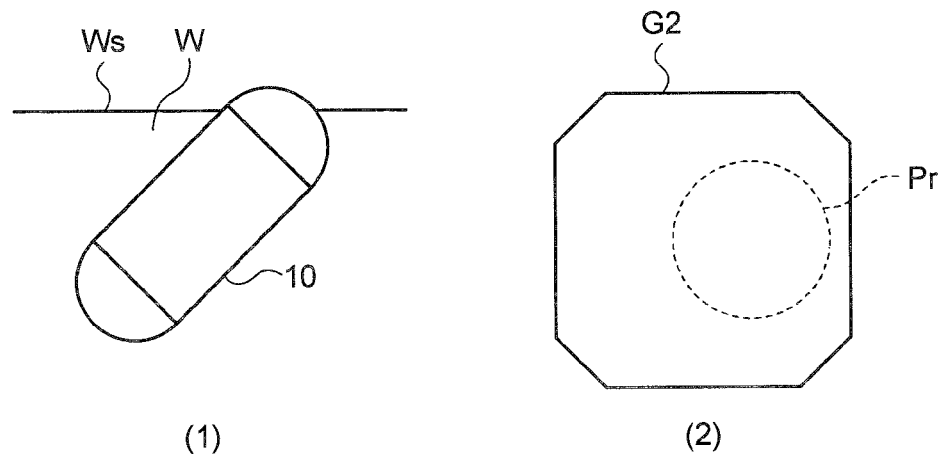
FIG. 27 is a diagram for explaining detection processing of a position detector shown in FIG. 25.

First, a case in which the capsule endoscope 10 is located in the water surface area will be described with reference to FIG. 27. As shown in FIG. 27 (1), when the capsule endoscope 10 is present in the water surface area, the distal end of the capsule endoscope 10 is exposed from the water surface Ws. The imaging view fields of the imaging units 11A and 11B stretch out from the distal ends of the capsule endoscope 10. Therefore, when, as shown in FIG. 27 (1), the distal end of the capsule endoscope 10 is exposed from the water surface Ws, as shown in the image G2 in FIG. 27 (2), the boundary Pr between the water surface Ws and the distal end of the capsule endoscope 10 is displayed as a ring shape by the water rising up on the side surface of the capsule endoscope 10 due to the surface tension and reflection of the illumination from the illumination unit 13A or 13B. Therefore, the position detector 243 determines whether or not there is a ring-shaped image pattern in the image captured by the capsule endoscope 10, and if there is a ring-shaped image pattern, the position detector 243 determines that the capsule endoscope 10 is present in the water surface area.

Figure 28:
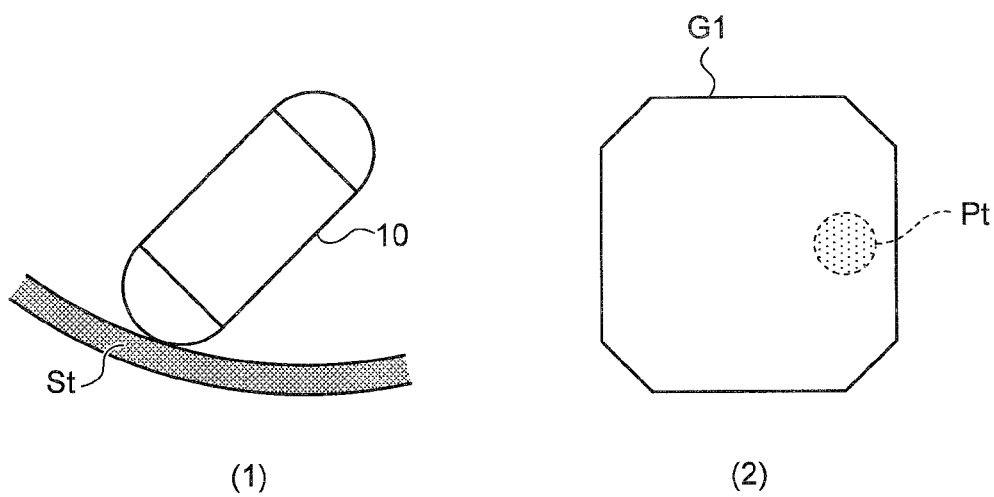
FIG. 28 is a diagram for explaining the detection processing of the position detector shown in FIG. 25.

Next, a case in which the capsule endoscope 10 is located in the water bottom area will be described with reference to FIG. 28. As shown in FIG. 28 (1), when the capsule endoscope 10 is present in the water bottom area, the distal end of the capsule endoscope 10 is pressed onto the stomach wall St. Therefore, in a case of FIG. 28 (1), as shown in the image G1 in FIG. 28 (2), a contact portion Pt between the stomach wall St and the distal end of the capsule endoscope 10 is displayed as a circular shape. Therefore, the position detector 243 determines whether or not there is a circular-shaped image pattern in the image captured by the capsule endoscope 10, and if there is a circular-shaped image pattern, the position detector 243 determines that the capsule endoscope 10 is present in the water bottom area.

If the position detector 243 determines that there is neither a ring-shaped image pattern nor a circular-shaped image pattern in the image captured by the capsule endoscope 10, the position detector 243 determines that the capsule endoscope 10 is present in the underwater area.

Then the magnetic field control instruction unit 245 determines whether or not the presence area of the capsule endoscope 10 matches the guidance area selected by the operation input unit 60 on the basis of the detection result of the position detector 243 (step S216).

If the magnetic field control instruction unit 245 determines that the presence area of the capsule endoscope 10 does not match the guidance area selected by the operation input unit 60 (step S216: No), the magnetic field control instruction unit 245 determines which area is instructed to be set as the guidance area (step S217). If the magnetic field control instruction unit 245 determines that the guidance area instructed to be set is the underwater area or the water bottom area (step S217: underwater or water bottom), the magnetic field control instruction unit 245 determines whether or not the capsule endoscope 10 is currently present in the water surface area (step S218). If the magnetic field control instruction unit 245 determines that the capsule endoscope 10 is currently present in the water surface area (step S218: Yes), the magnetic field control instruction unit 245 sets the diving mode to be the ON state (step S219).

Next, if the magnetic field control instruction unit 245 determines that the guidance area instructed to be set is the water surface area (step S217: water surface), or determines that the capsule endoscope 10 is not currently present in the water surface area (step S218: No), or the ON state of the diving mode set in step S219 is discontinued, the magnetic field control instruction unit 245 instructs the magnetic field controller 8 to generate a magnetic field for guiding the capsule endoscope 10 to the selected guidance area. As a result, the magnetic field generator 2 generates a magnetic field for moving the capsule endoscope 10 to the selected guidance area (step S220). As the magnetic field generated here, the magnetic field control instruction unit 245 causes the magnetic field generator 2 to generate a magnetic field having a magnetic force shown in table T2 in FIG. 11. Further, if the presence area of the capsule endoscope 10 is the water surface area, and the guidance area is set to be the underwater area or the water bottom area, the diving mode is set to be the ON state, so that the magnetic field control instruction unit 245 once causes the magnetic field generator 2 to generate a magnetic field having a high strength that can overcome the surface tension of the water surface so as to move the capsule endoscope 10 in the vertically downward direction with respect to the water surface, and then causes the magnetic field generator 2 to generate a magnetic field having a magnetic force shown in table T2 in accordance with the condition of table T1. In this case, even when an operator does not perform an operation to set the diving mode to be the ON state, the diving mode is automatically set to be the ON state, the operability is further improved. As a result, the capsule endoscope 10 moves to the set guidance area and stably located in the set guidance area.

If the external control unit 204 determines that the automatic detection mode for automatically detecting the presence area of the capsule endoscope 10 is not set (step S212: No), or if the magnetic field control instruction unit 245 determines that the presence area of the capsule endoscope 10 matches the guidance area selected by the operation input unit 60 (step S216: Yes), or if the magnetic field generation processing in step S220 is completed, in the same manner as in step S12 in FIG. 19, the magnetic field control instruction unit 245 determines whether or not there is a movement instruction of the capsule endoscope 10 (step S222).

In the same manner as in the first embodiment, if the magnetic field control instruction unit 245 determines that there is a movement instruction of the capsule endoscope 10 (step S222; Yes), the magnetic field control instruction unit 245 calculates the moving position instructed by the operation information from the operation input unit 60 (step S224), and obtains the condition of the magnetic field applied to the permanent magnet 19 of the capsule endoscope 10 on the basis of the magnetic field generation condition corresponding to the guidance area (step S226). Then the magnetic field control instruction unit 245 instructs the magnetic field controller 8 to generate a magnetic field in the obtained condition of the magnetic field, and the magnetic field generator 2 performs magnetic field generation processing for generating a magnetic field in the instructed condition (step S228). As a result, the capsule endoscope 10 is moved in the direction and the position according to the operation processing of the operation input unit 60. When there is a movement component in the vertically downward direction and the diving mode is the ON state, the magnetic field control instruction unit 245 instructs the magnetic field controller 8 to cause the magnetic field generator 2 to generate a magnetic field that overcomes the surface tension.

If the magnetic field control instruction unit 245 determines that there is no movement instruction of the capsule endoscope 10 (step S222: No), or if the magnetic field generation processing (step S228) is completed, the image receiving unit 41 performs image receiving processing (step S230) and the image display controller 42 performs image display processing (step S232). As a result, the display unit 5 sequentially displays in-vivo images captured by the capsule endoscope 10. Next, the external control unit 204 determines whether or not the in-vivo observation is completed on the basis of instruction information input by the input unit 6 (step S234). If the external control unit 204 determines that the in-vivo observation is not completed (step S234: No), the external control unit 204 returns to step S208 to continue the in-vivo observation and determines whether or not there is a setting instruction of the guidance area. If the external control unit 204 determines that the in-vivo observation is completed (step S234: Yes), the external control unit 204 ends the in-vivo observation.

In this way, in the second embodiment, the area where the capsule endoscope 10 is present is automatically detected from the image of the capsule endoscope 10, and if the detected presence area of the capsule endoscope 10 does not match the set guidance area, a magnetic field for guiding the capsule endoscope 10 to the set guidance area is automatically generated. Therefore, according to the embodiment, the operator need not perform an operation to guide the capsule endoscope 10 to a desired guidance area on the basis of the image displayed on the display unit 5, so that the capsule endoscope 10 can be correctly guided by an operation much easier than that of the first embodiment.

When the combination of the guidance areas is only the combination of the water surface area and the water bottom area, the position detector 243 may determine only whether or not there is a ring-shaped image pattern in the image captured by the capsule endoscope 10 without determining whether or not there is a circular-shaped image pattern. In this case, if the position detector 243 determines that there is a ring-shaped image pattern in the image captured by the capsule endoscope 10, the position detector 243 determines that the presence area of the capsule endoscope 10 is the water surface area, and if the position detector 243 determines that there is no ring-shaped image pattern, the position detector 243 determines that the presence area of the capsule endoscope 10 is the water bottom area. In this case, the detection processing of the capsule endoscope 10 can be further simplified.

Figure 29:
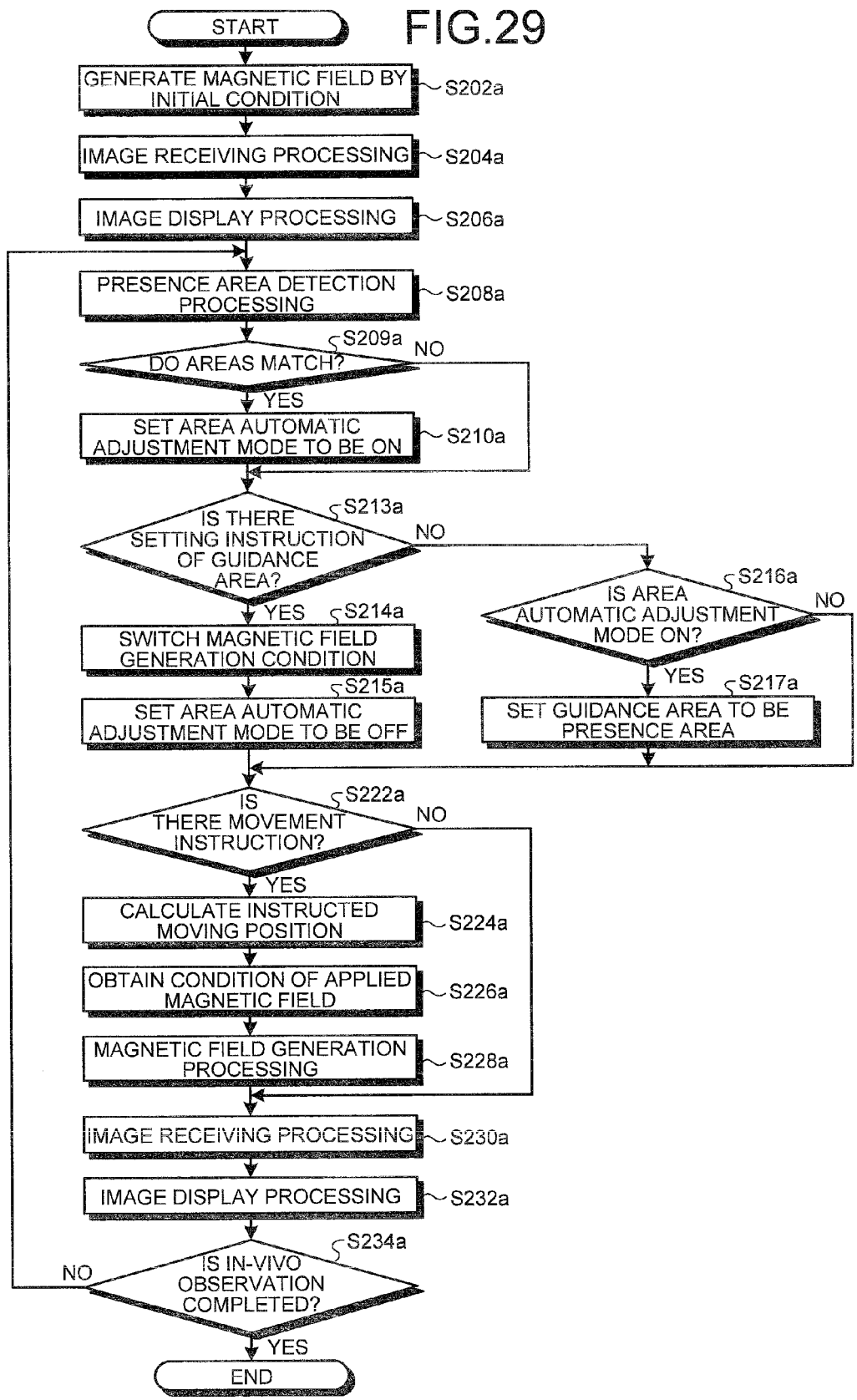
FIG. 29 is a flowchart showing another processing procedure of the guidance processing of the capsule endoscope of the capsule medical device guidance system shown in FIG. 25.

In the second embodiment, by performing processing procedures shown in FIG. 29, the capsule endoscope 10 may be magnetically guided smoothly by setting an area automatic adjustment mode for setting the magnetic field generation condition in accordance with the area in which the capsule endoscope 10 is actually present.

As shown in FIG. 29, first, in the same manner as in step S2 in FIG. 19, when the input unit 6 inputs instruction information for instructing a start of in-vivo observation, the magnetic field control instruction unit 245 transmits instruction information to the magnetic field controller 8 to generate a magnetic field by an initial condition (step S202a). Next, in the same manner as in steps S4 and S6 in FIG. 19, the image receiving unit 41 performs image receiving processing (step S204a) and the image display controller 42 performs image display processing (step S206a).

Thereafter, the position detector 243 performs presence area detection processing for detecting the presence area of the capsule endoscope 10 (step S208a). Then the magnetic field control instruction unit 245 determines whether or not the presence area of the capsule endoscope 10 matches the guidance area selected by the operation input unit 60 on the basis of the detection result of the position detector 243 (step S209a). If the magnetic field control instruction unit 245 determines that the presence area of the capsule endoscope 10 matches the guidance area selected by the operation input unit 60 (step S209a: Yes), the magnetic field control instruction unit 245 sets the area automatic adjustment mode to be the ON state (step S210a).

If the magnetic field control instruction unit 245 determines that the presence area of the capsule endoscope 10 does not match the guidance area selected by the operation input unit 60 (step S209a: No), or after the processing in step S210a is completed, in the same manner as in step S8 in FIG. 19, the magnetic field condition switching unit 46 determines whether or not there is a setting instruction of the guidance area (step S213a).

If the magnetic field condition switching unit 46 determines that there is a setting instruction of the guidance area (step S213a: Yes), the magnetic field condition switching unit 46 switches the magnetic field generation condition of the magnetic field generator 2 according to the guidance area selected by the operation input unit 60 on the basis of the input selection information (step S214a). Then the magnetic field control instruction unit 245 instructs the magnetic field generator 2 to generate a magnetic field for guiding the capsule endoscope 10 to the selected guidance area, and after the area in which the capsule endoscope 10 is actually present moves to the guidance area selected by the operation input unit 60 and the presence area matches the guidance area, the magnetic field control instruction unit 245 sets the area automatic adjustment mode to be the OFF state (step S215a).

On the other hand, if the magnetic field condition switching unit 46 determines that there is no setting instruction of the guidance area (step S213a: No), the magnetic field control instruction unit 245 determines whether or not the area automatic adjustment mode is the ON state (step S216a). If the magnetic field control instruction unit 245 determines that the area automatic adjustment mode is the ON state (step S216a: Yes), the magnetic field control instruction unit 245 sets the guidance area to be the area in which the capsule endoscope 10 is actually present (step S217a). The magnetic field condition switching unit 46 switches the magnetic field generation condition of the magnetic field generator 2 in accordance with the guidance area set by the magnetic field control instruction unit 245 in the setting processing in step S217a.

In the external control unit 204, after the processing in step S215a is completed, or if the magnetic field control instruction unit 245 determines that the area automatic adjustment mode is not the ON state (step S216a: No), or when the processing in step S217a is completed, in the same manner as in step S12 in FIG. 19, the magnetic field control instruction unit 245 determines whether or not there is a movement instruction of the capsule endoscope 10 (step S222a). In the same manner as in the first embodiment, if the magnetic field control instruction unit 245 determines that there is a movement instruction of the capsule endoscope 10 (step S222a: Yes), the magnetic field control instruction unit 245 calculates the moving position instructed by the operation information from the operation input unit 60 (step S224a), and obtains the condition of the magnetic field applied to the permanent magnet 19 of the capsule endoscope 10 on the basis of the magnetic field generation condition corresponding to the guidance area (step S226a). Then the magnetic field control instruction unit 245 instructs the magnetic field controller 8 to generate a magnetic field in the obtained condition of the magnetic field, and the magnetic field generator 2 performs magnetic field generation processing for generating a magnetic field in the instructed condition (step S228a). If the magnetic field control instruction unit 245 determines that there is no movement instruction of the capsule endoscope 10 (step S222a: No), or if the magnetic field generation processing (step S228a) is completed, the image receiving unit 41 performs image receiving processing (step S230a) and the image display controller 42 performs image display processing (step S232a). As a result, the display unit 5 sequentially displays in-vivo images captured by the capsule endoscope 10. Next, the external control unit 204 determines whether or not the in-vivo observation is completed on the basis of instruction information input by the input unit 6 (step S234a). If the external control unit 204 determines that the in-vivo observation is not completed (step S234a: No), the external control unit 204 returns to step S208a to continue the in-vivo observation, and performs presence area detection processing. If the external control unit 204 determines that the in-vivo observation is completed (step S234a: Yes), the external control unit 204 ends the in-vivo observation.

When the area automatic adjustment mode is set by performing processing procedures shown in FIG. 29, the magnetic field generation condition can be automatically switched in accordance with the area in which the capsule endoscope 10 is actually present. As a result, even when the presence area in which the capsule endoscope 10 is actually present is out of the guidance area set by the operation input unit 60, for example, when the capsule endoscope 10 moves to the water surface area while guiding the capsule endoscope 10 with the guidance area being set to be the underwater area, the guidance area is automatically switched to the presence area. Then, as the guidance area is switched to the presence area, the magnetic field generation condition is also switched to a magnetic field generation condition corresponding to the area in which the capsule endoscope 10 is actually present. Therefore, by performing processing procedures shown in FIG. 29, a stable guidance can be always implemented in the area in which the capsule endoscope 10 is present.

Third Embodiment

Next, a third embodiment will be described. When moving the capsule endoscope 10 by generating the uniform gradient magnetic field, the position of the capsule endoscope 10 often becomes unstable, so that, in the third embodiment, the peak position on the horizontal plane of the previously-generated peak magnetic field is stored, and when the magnetic field is switched from the uniform gradient magnetic field to the peak magnetic field, the position of the capsule endoscope 10 is fixed by generating the peak magnetic field whose peak is located at the stored position.

Figure 30:
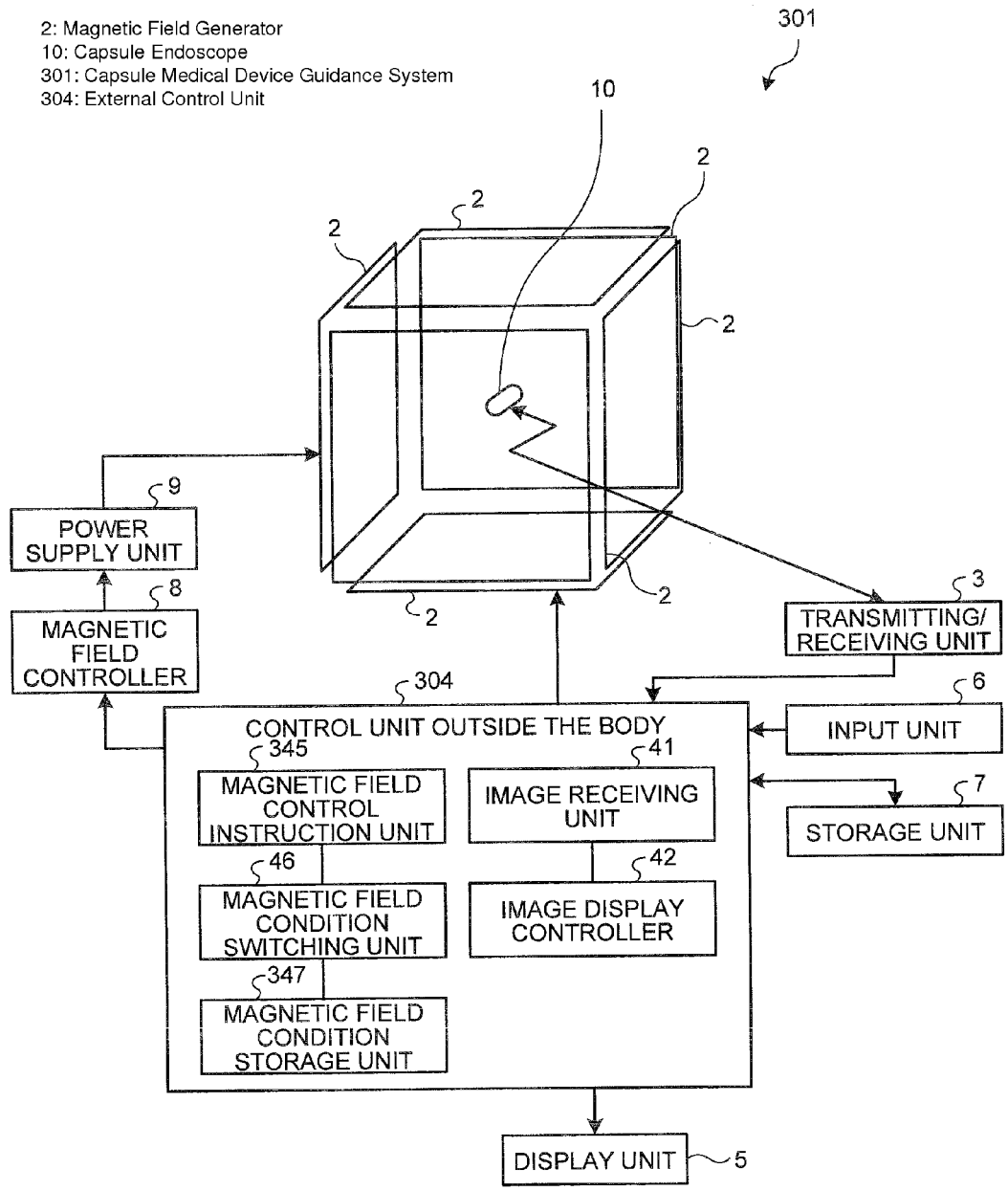
FIG. 30 is a schematic diagram showing an entire configuration of the capsule medical device guidance system according to a third embodiment.

FIG. 30 is a schematic diagram showing an entire configuration of the capsule medical device guidance system according to the third embodiment of the present invention. As shown in FIG. 30, a capsule medical device guidance system 301 according to the third embodiment has a configuration including an external control unit 304 instead of the external control unit 4 shown in FIG. 1. Compared with the external control unit 4, the external control unit 304 includes a magnetic field control instruction unit 345 instead of the magnetic field control instruction unit 45, and a magnetic field condition storage unit 347 instead of the magnetic field condition storage unit 47.

The magnetic field control instruction unit 345 stores each magnetic field condition respectively corresponding to each guidance area into the magnetic field condition storage unit 347, and also causes the magnetic field condition storage unit 347 to store a position on the horizontal plane at which the previously-generated peak magnetic field is generated, that is to say, a position on the horizontal plane of the peak of the peak magnetic field. When the magnetic field control instruction unit 345 switches a magnetic field generated by the magnetic field generator 2 from the peak magnetic field to the uniform gradient magnetic field, the magnetic field control instruction unit 345 causes the magnetic field condition storage unit 347 to store the position on the horizontal plane at which the peak magnetic field is generated, that is to say, the position on the horizontal plane of the peak of the peak magnetic field. Specifically, when the magnetic field control instruction unit 345 switches a magnetic field generated by the magnetic field generator 2 from the peak magnetic field to the uniform gradient magnetic field, the magnetic field control instruction unit 345 causes the magnetic field condition storage unit 347 to store the magnetic field gradient in the vertical direction of the peak magnetic field. When the magnetic field control instruction unit 345 switches a magnetic field generated by the magnetic field generator 2 from the peak magnetic field to the uniform gradient magnetic field, the magnetic field control instruction unit 345 causes the magnetic field condition storage unit 347 to store the direction of the peak magnetic field.

When the magnetic field control instruction unit 345 switches a magnetic field generated by the magnetic field generator 2 from the uniform gradient magnetic field to the peak magnetic field, the magnetic field control instruction unit 345 causes the magnetic field generator 2 to generate the peak magnetic field at the position stored in the magnetic field condition storage unit 347. Specifically, when the magnetic field control instruction unit 345 switches a magnetic field generated by the magnetic field generator 2 from the uniform gradient magnetic field to the peak magnetic field, the magnetic field control instruction unit 345 causes the magnetic field generator 2 to generate the peak magnetic field with the magnetic field gradient in the vertical direction stored in the magnetic field condition storage unit 347. When the magnetic field control instruction unit 345 switches a magnetic field generated by the magnetic field generator 2 from the uniform gradient magnetic field to the peak magnetic field, the magnetic field control instruction unit 345 causes the magnetic field generator 2 to generate the peak magnetic field in the direction stored in the magnetic field condition storage unit 347. When the magnetic field control instruction unit 345 changes the type of magnetic field due to a change of guidance area, the magnetic field control instruction unit 345 performs storage processing and read processing of the magnetic field condition related to the generation position of the peak magnetic field.

The storage processing and the read processing will be specifically described for each change of guidance areas. First, a case will be described in which the guidance area is switched from the water surface area to the underwater area or the water bottom area on the basis of the selection information from the operation input unit 60. This case corresponds to a case in which the generated magnetic field is switched from the peak magnetic field to the uniform gradient magnetic field.

Figure 31:
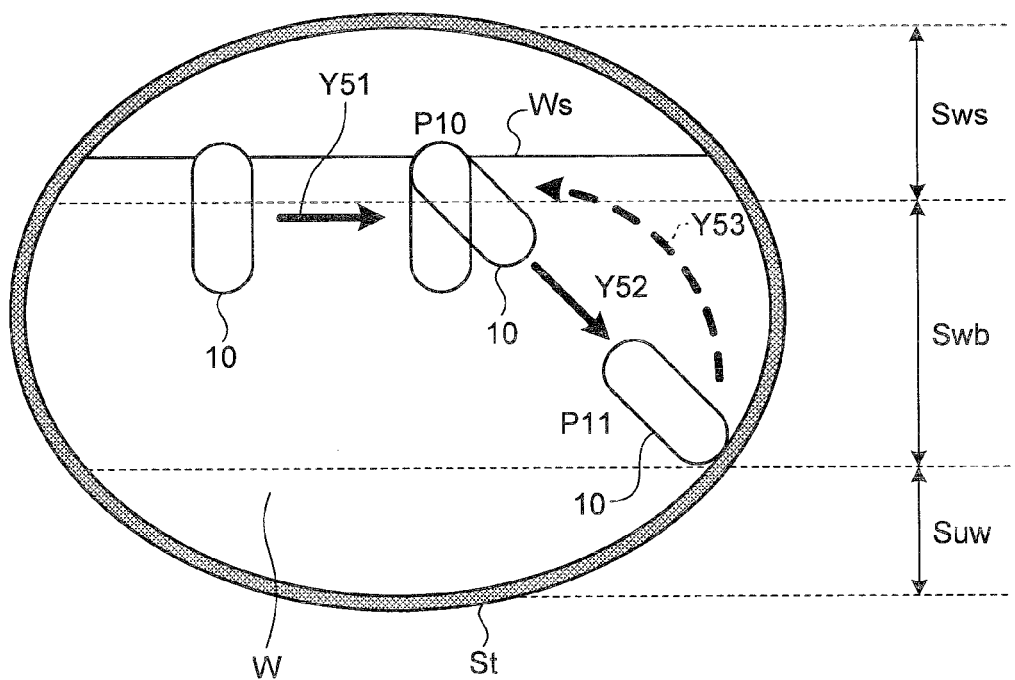
FIG. 31 is a diagram showing a state in which the capsule endoscope is located inside the stomach of the subject.

First, the guidance area of the capsule endoscope 10 is set to the water surface area before the switching, so that the magnetic field generator 2 generates the peak magnetic field, and for example, moves the capsule endoscope 10 to the position P10 as shown by the arrow Y51 in FIG. 31. When there is a switching instruction for changing the guidance area from the water surface area to the underwater area or the water bottom area at this timing, the magnetic field control instruction unit 345 causes the magnetic field condition storage unit 347 to store the generation condition of the peak magnetic field that traps the capsule endoscope 10 at the position P10, such as, for example, the magnetic field gradient in the vertical direction of the peak magnetic field and the direction of the peak magnetic field as the generation position on the horizontal plane of the peak of the peak magnetic field.

Thereafter, the magnetic field condition switching unit 46 switches the magnetic field generation condition of the magnetic field generator 2 in accordance with the newly selected guidance area. This switching of the guidance area requires a movement in the vertically downward direction with respect to the water surface. Therefore, at the timing when the magnetic field control instruction unit 345 receives a movement instruction of the capsule endoscope 10 in the vertically downward direction, the magnetic field control instruction unit 345 once causes the magnetic field generator 2 to generate a magnetic field having a high strength that can overcome the surface tension of the water surface. In this case, even when an operator does not perform an operation to set the diving mode to be the ON state, the capsule endoscope 10 moves automatically in the diving mode, so that the operator can guide the capsule endoscope 10 to the underwater area or the water bottom area without considering the effect of the surface tension.

Thereafter, the magnetic field control instruction unit 345 causes the magnetic field generator 2 to generate the uniform gradient magnetic field in accordance with the condition of table T1 shown in FIG. 10, and for example, downwardly moves the capsule endoscope 10 to the position P11 near the stomach wall St as shown by the arrow Y52. The uniform gradient magnetic field technically includes a magnetic field distortion, so that the movement of the capsule endoscope 10 becomes unstable in an environment without friction such as the water surface. Therefore, the magnetic field control instruction unit 345 may continue the generation of the peak magnetic field by the magnetic field generator 2 so that the position of the capsule endoscope 10 can be fixed for stable operation until the operation input unit 60 inputs operation information. In this case, the magnetic field control instruction unit 345 causes the magnetic field generator 2 to generate the uniform gradient magnetic field after the operation input unit 60 inputs operation information.

Next, a case will be described in which the guidance area is switched from the underwater area or the water bottom area to the water surface area on the basis of the selection information from the operation input unit 60. This case corresponds to a case in which the generated magnetic field is switched from the uniform gradient magnetic field to the peak magnetic field. In this case, the magnetic field condition switching unit 46 switches the magnetic field generation condition from the uniform gradient magnetic field corresponding to the underwater area or the water bottom area to the peak magnetic field corresponding to the water surface area. The magnetic field control instruction unit 345 obtains the generation condition of the previous peak magnetic field stored in the magnetic field condition storage unit 347, and causes the magnetic field generator 2 to generate the peak magnetic field in this condition.

As a result, as shown by the arrow Y53 in FIG. 31, the capsule endoscope 10 that has moved to the position P11 returns to the position P10 that is the position at which the capsule endoscope 10 was located immediately before moving to the water bottom area. In summary, when the guidance area is switched to the water surface area from another area, the capsule endoscope 10 automatically returns to the position in the water surface area at which the capsule endoscope 10 was located immediately before moving to the underwater area or the water bottom area. The operator only has to switch the guidance area to the water surface area from another area, and without performing the guidance operation to return the capsule endoscope 10 to the water surface area, the operator can smoothly restart the in-vivo observation by the capsule endoscope 10 and the guidance of the capsule endoscope 10 from the position P10 in the water surface area that is the position at which the capsule endoscope 10 was located immediately before moving to the underwater area or the water bottom area.

When the guidance area is switched from the underwater area to the water bottom area or switched from the water bottom area to the underwater area, the type of the magnetic field is not switched in the magnetic field generation condition and the magnetic field remains in the uniform gradient magnetic field, so that the magnetic field control instruction unit 345 need not perform the storage processing of the generation condition of the peak magnetic field.

Figure 32:
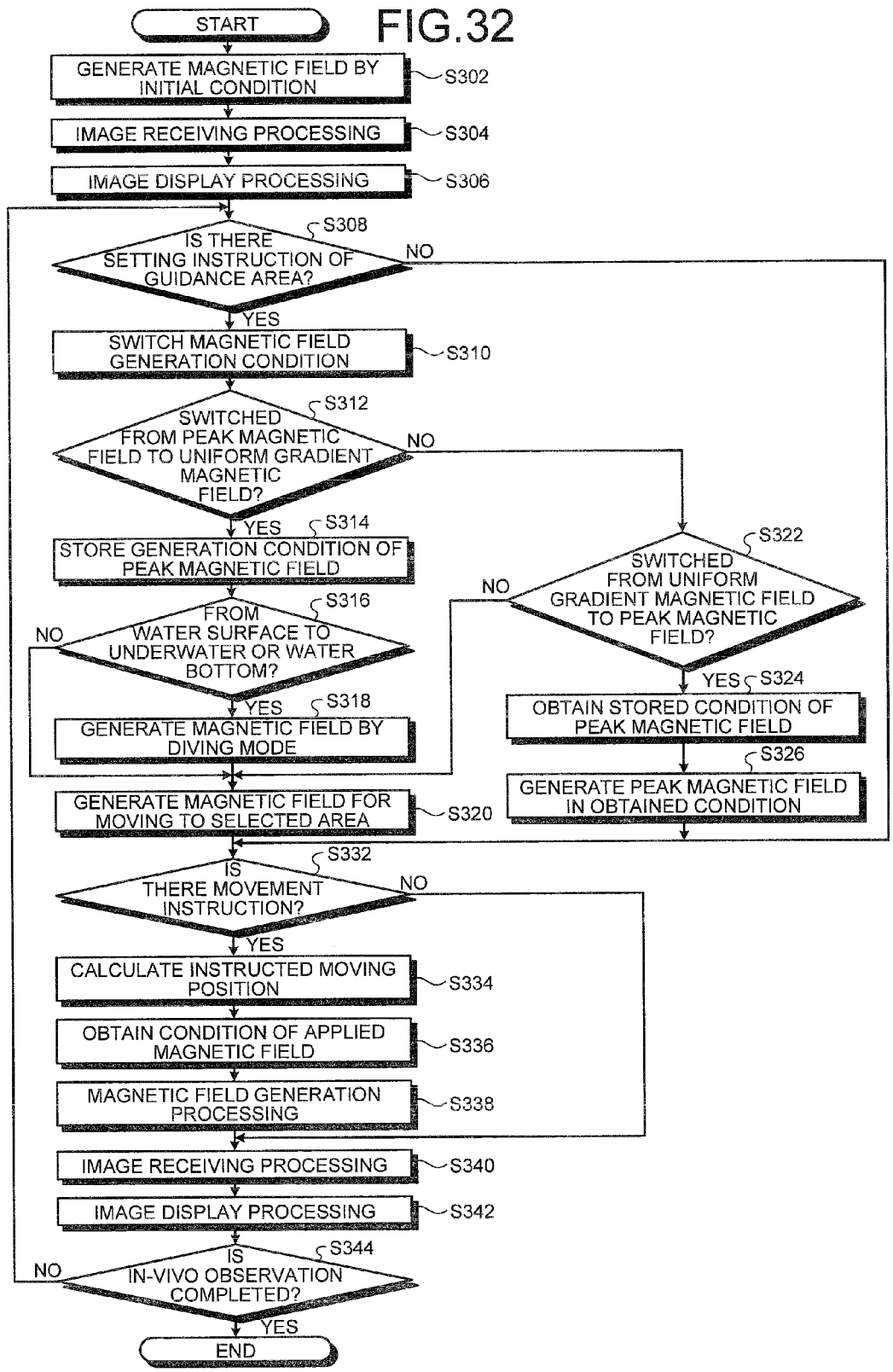
FIG. 32 is a flowchart showing a processing procedure of the guidance processing of the capsule endoscope of the capsule medical device guidance system shown in FIG. 30.

Next, the guidance processing of the capsule endoscope 10 of the capsule medical device guidance system 301 shown in FIG. 30 will be described with reference to FIG. 32. FIG. 32 is a flowchart showing a processing procedure of the guidance processing of the capsule endoscope 10 of the capsule medical device guidance system 301 shown in FIG. 30.

As shown in FIG. 32, first, in the same manner as in step S2 in FIG. 19, when the input unit 6 inputs instruction information for instructing a start of in-vivo observation, the magnetic field control instruction unit 345 transmits instruction information to the magnetic field controller 8 to generate a magnetic field by an initial condition (step S302). Next, in the same manner as in steps S4 and S6 in FIG. 19, the image receiving unit 41 performs image receiving processing (step S304) and the image display controller 42 performs image display processing (step S306).

In the external control unit 304, in the same manner as in step S8 in FIG. 19, the magnetic field condition switching unit 46 determines whether or not there is a setting instruction of the guidance area (step S308). If the magnetic field condition switching unit 46 determines that there is a setting instruction of the guidance area (step S308: Yes), the magnetic field condition switching unit 46 switches the magnetic field generation condition of the magnetic field generator 2 according to the guidance area selected by the operation input unit 60 on the basis of the input selection information (step S310). On the other hand, if the magnetic field condition switching unit 46 determines that there is no setting instruction of the guidance area (step S308: No), the process proceeds to step S332 described below.

Next, the magnetic field control instruction unit 345 determines whether or not the type of the magnetic field in the magnetic field generation condition is switched from the peak magnetic field to the uniform gradient magnetic field in the switching processing of the magnetic field generation condition in step S310 by the setting instruction of the guidance area (step S312).

A case will be described in which the magnetic field control instruction unit 345 determines that the type of the magnetic field in the magnetic field generation condition is switched from the peak magnetic field to the uniform gradient magnetic field (step S312: Yes). This case is a case in which the guidance area is switched from the water surface area to the underwater area or the water bottom area. In this case, the magnetic field control instruction unit 345 causes the magnetic field condition storage unit 347 to store the generation condition of the peak magnetic field that is generated immediately before the switching (step S314). Then the magnetic field control instruction unit 345 determines whether or not there is a movement instruction from the water surface area to the underwater area or the water bottom area (step S316). In other words, the magnetic field control instruction unit 345 determines whether or not the operation input unit 60 inputs the movement instruction of the capsule endoscope 10 in the vertically downward direction as the operation information.

If the magnetic field control instruction unit 345 determines that there is a movement instruction from the water surface area to the underwater area or the water bottom area (step S316: Yes), the magnetic field control instruction unit 345 causes the magnetic field generator 2 to generate a magnetic field by the diving mode described above (step S318), and correctly moves the capsule endoscope 10 from the water surface area to the underwater area or the water bottom area. Then the magnetic field control instruction unit 345 causes the magnetic field generator 2 to generate a magnetic field for moving the capsule endoscope 10 to the underwater area or the water bottom area selected as the guidance area (step S320) by causing the magnetic field generator 2 to generate the uniform gradient magnetic field according to the magnetic field generation condition switched by the magnetic field condition switching unit 46, and moves the capsule endoscope 10 to the selected guidance area.

On the other hand, if the magnetic field control instruction unit 345 determines that the type of the magnetic field in the magnetic field generation condition is not switched from the peak magnetic field to the uniform gradient magnetic field in the switching processing of the magnetic field generation condition in step S310 by the setting instruction of the guidance area (step S312: No), the magnetic field control instruction unit 345 further determines whether or not the type of the magnetic field in the magnetic field generation condition is switched from the uniform gradient magnetic field to the peak magnetic field (step S322).

A case will be described in which the magnetic field control instruction unit 345 determines that the type of the magnetic field in the magnetic field generation condition is switched from the uniform gradient magnetic field to the peak magnetic field (step S322: Yes). This case is a case in which the guidance area is switched from the underwater area or the water bottom area to the water surface area. In this case, the magnetic field control instruction unit 345 obtains the generation condition of the previous peak magnetic field stored in the magnetic field condition storage unit 347 (step S324), and causes the magnetic field generator 2 to generate the peak magnetic field in the obtained condition (step S326). As a result, the capsule endoscope 10 returns to the position in the water surface area at which the capsule endoscope 10 was located at the previous time.

On the other hand, a case in which the magnetic field control instruction unit 345 determines that the type of the magnetic field in the magnetic field generation condition is not switched from the uniform gradient magnetic field to the peak magnetic field (step S322: No), in other words, the type of the magnetic field in the magnetic field generation condition remains in the uniform gradient magnetic field corresponds to a case in which the guidance area is switched from the underwater area to the water bottom area or switched from the water bottom area to the underwater area. In this case, the magnetic field control instruction unit 345 causes the magnetic field generator 2 to generate a magnetic field for moving the capsule endoscope 10 to the underwater area or the water bottom area selected as the guidance area (step S320) by causing the magnetic field generator 2 to generate the uniform gradient magnetic field according to the magnetic field generation condition switched by the magnetic field condition switching unit 46, and moves the capsule endoscope 10 to the selected guidance area.

After the magnetic field control instruction unit 345 causes the magnetic field generator 2 to generate a magnetic field for moving the capsule endoscope 10 to the selected guidance area, in the same manner as in the first embodiment, the magnetic field control instruction unit 345 determines whether or not there is a movement instruction of the capsule endoscope 10 (step S332). In the same manner as in the first embodiment, if the magnetic field control instruction unit 345 determines that there is a movement instruction of the capsule endoscope 10 (step S332; Yes), the magnetic field control instruction unit 345 calculates the moving position instructed by the operation information from the operation input unit 60 (step S334), and obtains the condition of the magnetic field applied to the permanent magnet 19 of the capsule endoscope 10 on the basis of the magnetic field generation condition corresponding to the guidance area (step S336). Then the magnetic field control instruction unit 345 instructs the magnetic field controller 8 to generate a magnetic field in the obtained condition of the magnetic field, and the magnetic field generator 2 performs magnetic field generation processing for generating a magnetic field in the instructed condition (step S338). As a result, the capsule endoscope 10 is moved in the direction and the position according to the operation processing of the operation input unit 60.

If the magnetic field control instruction unit 345 determines that there is no movement instruction of the capsule endoscope 10 (step S332: No), or if the magnetic field generation processing (step S338) is completed, the image receiving unit 41 performs image receiving processing (step S340) and the image display controller 42 performs image display processing (step S342). As a result, the display unit 5 sequentially displays in-vivo images captured by the capsule endoscope 10. Next, the external control unit 304 determines whether or not the in-vivo observation is completed on the basis of instruction information input by the input unit 6 (step S344). If the external control unit 304 determines that the in-vivo observation is not completed (step S344: No), the external control unit 304 returns to step S308 to continue the in-vivo observation and determines whether or not there is a setting instruction of the guidance area. If the external control unit 304 determines that the in-vivo observation is completed (step S334: Yes), the external control unit 304 ends the in-vivo observation.

In this way, in the third embodiment, when the magnetic field is switched from the uniform gradient magnetic field to the peak magnetic field, the peak position on the horizontal plane of the previously-generated peak magnetic field is stored, and when the magnetic field is switched from the uniform gradient magnetic field to the peak magnetic field, the position of the capsule endoscope 10 is fixed by generating the peak magnetic field whose peak is located at the stored position. Therefore, according to the third embodiment, even when an operator moves the capsule endoscope 10 by generating the uniform gradient magnetic field and the operator cannot determine the position of the capsule endoscope 10, the capsule endoscope 10 automatically returns to the original position in the water surface area when the magnetic field is switched from the uniform gradient magnetic field to the peak magnetic field, so that the operator can smoothly restart the in-vivo observation by the capsule endoscope 10 and the guidance of the capsule endoscope 10 from the original position in the water surface area without performing the guidance operation to return the capsule endoscope 10 to the water surface area.

Figure 33:
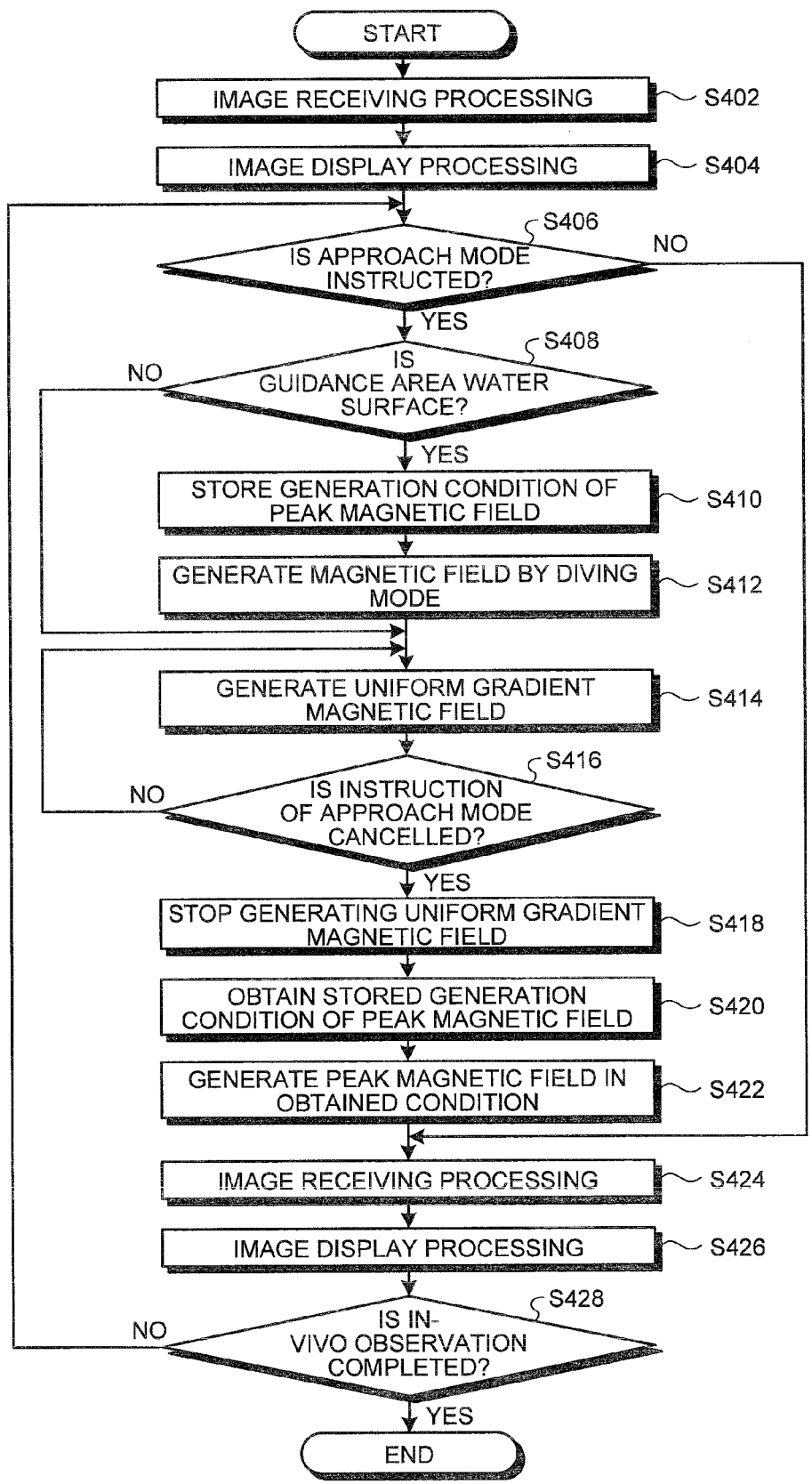
FIG. 33 is a flowchart showing a processing procedure of approach mode processing of the capsule endoscope of the capsule medical device guidance system shown in FIG. 30.

In the capsule medical device guidance system 301, not only when the guidance area is switched, but also when causing the capsule endoscope 10 located in the water surface area to approach an imaging object in the underwater area or the water bottom area by selecting the approach mode during the in-vivo observation by the capsule endoscope 10, the storage processing of the generation condition of the peak magnetic field is performed. This case will be described with reference to FIG. 33. FIG. 33 is a flowchart showing a processing procedure of the approach mode processing in the capsule medical device guidance system shown in FIG. 30.

As shown in FIG. 33, in the external control unit 304, the image receiving unit 41 performs image receiving processing (step S402), the image display controller 42 performs image display processing (step S404), and the magnetic field control instruction unit 345 determines whether or not the approach mode is instructed on the basis of operation information from the operation input unit 60 (step S406). If the magnetic field control instruction unit 345 determines that the approach mode is instructed (step S406: Yes), the magnetic field control instruction unit 345 determines whether or not the set guidance area is the water surface area (step S408). If the magnetic field control instruction unit 345 determines that the set guidance area is the water surface area (step S408: Yes), the position on the horizontal plane of the capsule endoscope 10 is controlled by the peak magnetic field, so that the magnetic field control instruction unit 345 causes the magnetic field condition storage unit 347 to store the peak magnetic field generation condition including the peak position on the horizontal plane of the peak magnetic field (step S410). Then the magnetic field control instruction unit 345 causes the magnetic field generator 2 to generate a magnetic field by the above-described diving mode (step S412). As a result, it is possible to correctly move the capsule endoscope 10 from the water surface area to the underwater area.

When the processing in step S412 is completed, or when the magnetic field control instruction unit 345 determines that the set guidance area is not the water surface area (step S408: No), the magnetic field control instruction unit 345 causes the magnetic field generator 2 to generate the uniform gradient magnetic field having a gradient in the direction of the long axis La of the capsule endoscope 10 (step S414) and causes the capsule endoscope 10 to approach the imaging object.

Next, the magnetic field control instruction unit 345 determines whether or not the instruction of the approach mode is cancelled (step S416). If the magnetic field control instruction unit 345 determines that the instruction of the approach mode is not cancelled (step S416, No), in other words, determines that the instructed approach mode remains in effect, the process returns to step S414, and the magnetic field control instruction unit 345 causes the magnetic field generator 2 to continuously generate the uniform gradient magnetic field. On the other hand, if the magnetic field control instruction unit 345 determines that the instruction of the approach mode is cancelled (step S416, Yes), the magnetic field control instruction unit 345 causes the magnetic field generator 2 to stop generating the uniform gradient magnetic field (step S418). Then the magnetic field control instruction unit 345 obtains the generation condition of the previous peak magnetic field stored in the magnetic field condition storage unit 347 (step S420), and causes the magnetic field generator 2 to generate the peak magnetic field in the obtained condition (step S422). As a result, the capsule endoscope 10 returns to the position in the water surface area at which the capsule endoscope 10 was located before the approach mode.

Therefore, an operator can check the approached image by pressing the approach button 64. When the operator releases his or her finger from the approach button 64, the capsule endoscope 10 automatically returns to the position in the water surface area at which the capsule endoscope 10 was located before the approach button 64 is pressed, so that the operator can restart the guidance of the capsule endoscope 10 from the position in the water surface area at which the capsule endoscope 10 was located before the approach button 64 is pressed.

If the magnetic field control instruction unit 345 determines that the approach mode is not instructed (step S406: No), or if the peak magnetic field generation processing by the magnetic field generator 2 in step S422 is completed, the image receiving unit 41 performs image receiving processing (step S424) and the image display controller 42 performs image display processing (step S426). As a result, the display unit 5 sequentially displays in-vivo images captured by the capsule endoscope 10. Next, the external control unit 304 determines whether or not the in-vivo observation is completed on the basis of instruction information input by the input unit 6 (step S428). If the external control unit 304 determines that the in-vivo observation is not completed (step S428: No), the external control unit 304 returns to step S406 to continue the in-vivo observation and determines whether or not there is an instruction of the approach mode. If the external control unit 304 determines that the in-vivo observation is completed (step S428: Yes), the external control unit 304 ends the in-vivo observation.

Figure 34:
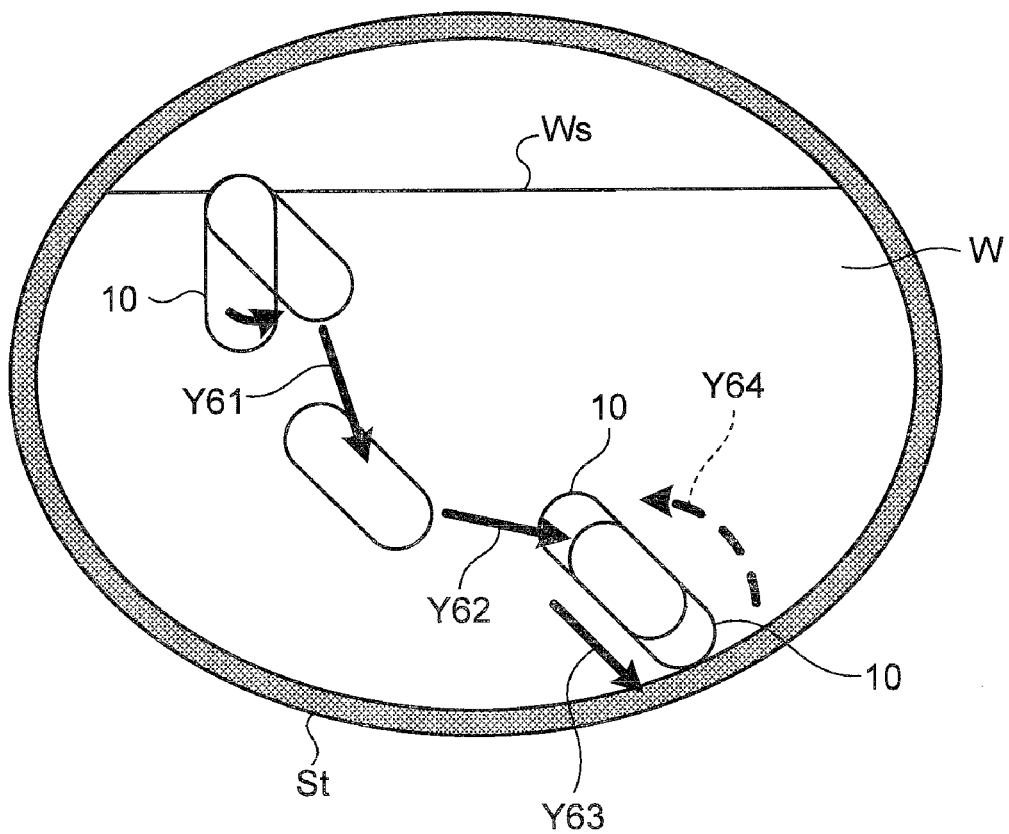
FIG. 34 is a diagram showing a state in which the capsule endoscope is located inside the stomach of the subject.

The approach mode can also be applied when guiding the capsule endoscope 10 in the underwater area by using the peak magnetic field. As shown in FIG. 34, the magnetic field control instruction unit 345 guides the capsule endoscope 10 by using the peak magnetic field in the underwater area, and also when the approach mode is instructed, the generation condition of the previous peak magnetic field is stored and then the uniform gradient magnetic field is generated in the same manner as described above, and thereby the magnetic field control instruction unit 345 causes the capsule endoscope 10 to approach the imaging object on the stomach wall St as shown by the arrow Y63. When the instruction of the approach mode is cancelled, the magnetic field control instruction unit 345 obtains the stored generation condition of the peak magnetic field and causes the magnetic field generator 2 to generate the peak magnetic field in the obtained condition. As a result, the capsule endoscope 10 returns to the position in the underwater area at which the capsule endoscope 10 was located before the approach mode was instructed.

Figure 35:
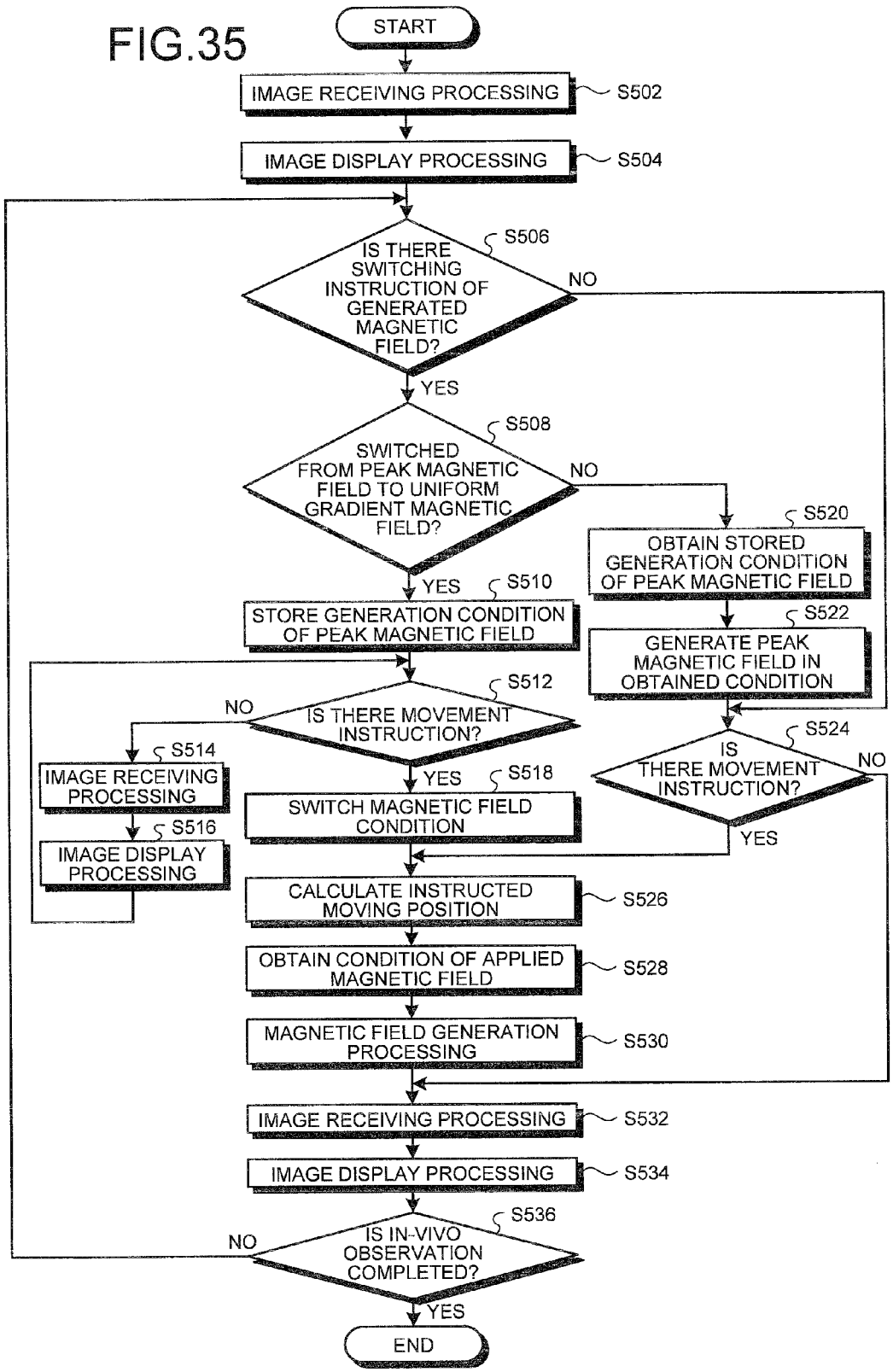
FIG. 35 is a flowchart showing a processing procedure of other guidance processing of the capsule endoscope of the capsule medical device guidance system shown in FIG. 30.

The approach mode can also be applied in a case in which the type of the magnetic field generated by the magnetic field generator 2 is manually switched from the peak magnetic field to the uniform gradient magnetic field or from the uniform gradient magnetic field to the peak magnetic field. This case will be described with reference to FIG. 35. FIG. 35 shows a case in which the type of the magnetic field is manually switched during the in-vivo observation by the capsule endoscope 10.

As shown in FIG. 35, in the external control unit 304, the image receiving unit 41 performs image receiving processing (step S502) and the image display controller 42 performs image display processing (step S504).

In the external control unit 304, the magnetic field control instruction unit 345 determines whether or not there is a switching instruction of the type of the magnetic field being generated on the basis of instruction information or the like from the input unit 6 (step S506). If the magnetic field control instruction unit 345 determines that there is a switching instruction of the type of the magnetic field being generated (step S506: Yes), the magnetic field control instruction unit 345 determines whether or not the type of the magnetic field is switched from the peak magnetic field to the uniform gradient magnetic field (step S508).

If the magnetic field control instruction unit 345 determines that the type of the magnetic field is switched from the peak magnetic field to the uniform gradient magnetic field (step S508: Yes), the magnetic field control instruction unit 345 causes the magnetic field condition storage unit 347 to store the peak magnetic field generation condition including the peak position on the horizontal plane of the peak magnetic field which has been generated until just before the type of the magnetic field is switched (step S510).

Then the magnetic field control instruction unit 345 determines whether or not there is a movement instruction of the capsule endoscope 10 (step S512). If the magnetic field control instruction unit 345 determines that there is no movement instruction of the capsule endoscope 10 (step S512: No), the image receiving unit 41 performs image receiving processing (step S514) and the image display controller 42 performs image display processing (step S516), and after the in-vivo observation by the capsule endoscope 10 is continued, the process returns to step S512. On the other hand, if the magnetic field control instruction unit 345 determines that there is a movement instruction of the capsule endoscope 10 (step S512: Yes), the magnetic field condition switching unit 46 switches a magnetic field generated by the magnetic field generator 2 from the peak magnetic field to the uniform gradient magnetic field (step S518). Then the magnetic field control instruction unit 345 calculates the moving position instructed by the operation information from the operation input unit 60 (step S526), and obtains the condition of the magnetic field applied to the permanent magnet 19 of the capsule endoscope 10 on the basis of the magnetic field generation condition corresponding to the guidance area (step S528). Then the magnetic field control instruction unit 345 instructs the magnetic field controller 8 to generate a magnetic field in the obtained condition of the magnetic field, and the magnetic field generator 2 performs magnetic field generation processing for generating a magnetic field in the instructed condition (step S530). In summary, the magnetic field control instruction unit 345 continues the generation of the peak magnetic field by the magnetic field generator 2 so that the position of the capsule endoscope 10 can be fixed for stable operation until the operation input unit 60 inputs operation information, and causes the magnetic field generator 2 to generate the uniform gradient magnetic field after the operation input unit 60 inputs operation information.

If the magnetic field control instruction unit 345 determines that the type of the magnetic field is not switched from the peak magnetic field to the uniform gradient magnetic field (step S508: No), in other words, if the magnetic field control instruction unit 345 determines that the type of the magnetic field is switched from the uniform gradient magnetic field to the peak magnetic field, the magnetic field control instruction unit 345 obtains the generation condition of the previous peak magnetic field stored in the magnetic field condition storage unit 347 (step S520), and causes the magnetic field generator 2 to generate the peak magnetic field in the obtained condition (step S522). As a result, the capsule endoscope 10 returns to the position in the water surface area at which the capsule endoscope 10 was located before. Then the magnetic field control instruction unit 345 determines whether or not there is a movement instruction of the capsule endoscope 10 (step S524). Also when the magnetic field control instruction unit 345 determines that there is no switching instruction of the type of the magnetic field being generated (step S506: No), the process proceeds to step S524.

If the magnetic field control instruction unit 345 determines that there is a movement instruction of the capsule endoscope 10 (step S524: Yes), the magnetic field control instruction unit 345 calculates the moving position instructed by the operation information from the operation input unit 60 (step S526), and obtains the condition of the magnetic field applied to the permanent magnet 19 of the capsule endoscope 10 on the basis of the magnetic field generation condition corresponding to the guidance area (step S528). Then the magnetic field control instruction unit 345 instructs the magnetic field controller 8 to generate a magnetic field in the obtained condition of the magnetic field, and the magnetic field generator 2 performs magnetic field generation processing for generating a magnetic field in the instructed condition (step S530). As a result, the capsule endoscope 10 is moved in the direction and the position according to the operation processing of the operation input unit 60.

If the magnetic field control instruction unit 345 determines that there is no movement instruction of the capsule endoscope 10 (step S524: No), or if the magnetic field generation processing (step S530) is completed, the image receiving unit 41 performs image receiving processing (step S532) and the image display controller 42 performs image display processing (step S534). As a result, the display unit 5 sequentially displays in-vivo images captured by the capsule endoscope 10. Next, the external control unit 304 determines whether or not the in-vivo observation is completed on the basis of instruction information input by the input unit 6 (step S536). If the external control unit 304 determines that the in-vivo observation is not completed (step S536: No), the external control unit 304 returns to step S506 to continue the in-vivo observation. If the external control unit 304 determines that the in-vivo observation is completed (step S536: Yes), the external control unit 304 ends the in-vivo observation.

Also in this case, even if the position of the capsule endoscope 10 cannot be determined when the capsule endoscope 10 is moved by generating the uniform gradient magnetic field, the capsule endoscope 10 automatically returns to the original position in the water surface area when the magnetic field is switched from the uniform gradient magnetic field to the peak magnetic field, so that the operator can smoothly restart the in-vivo observation by the capsule endoscope 10 and the guidance of the capsule endoscope 10 from the original position in the water surface area without performing the guidance operation to return the capsule endoscope 10 to the water surface area.

Figure 36:
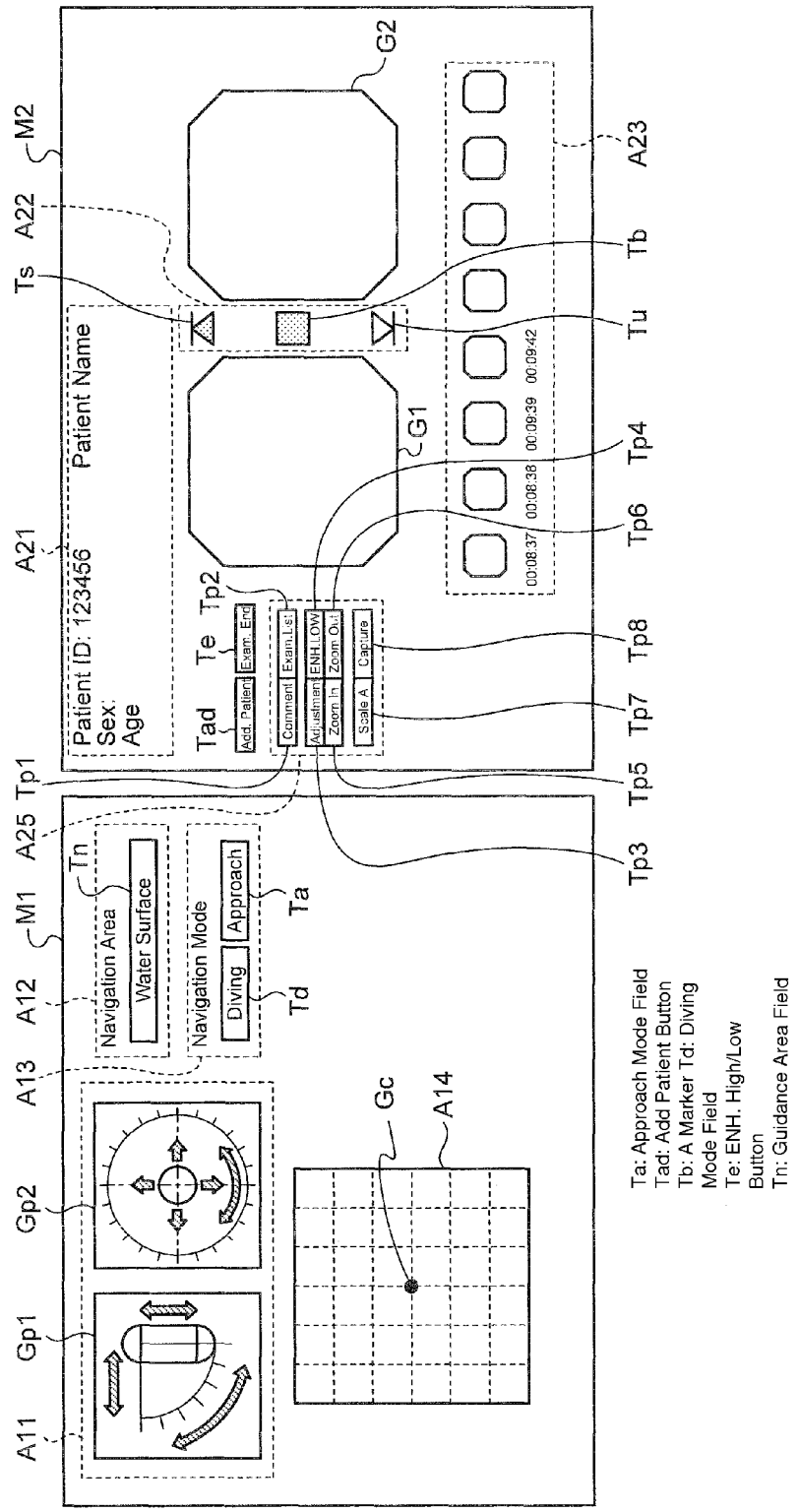
FIG. 36 is a diagram showing an example of a menu screen displayed on the display screen of the display unit shown in FIG. 1.

Next, the display content actually displayed by the display unit 5 will be described. FIG. 36 is a diagram illustrating a menu screen displayed by the display unit 5. As shown in FIG. 36, the display unit 5 displays two menu screens, which are a guidance menu M1 and an observation menu M2. The guidance menu M1 is a menu screen for supporting the guidance of the capsule endoscope 10, and the observation menu M2 is a menu screen for supporting the observation of the in-vivo image transmitted from the capsule endoscope 10.

First, the guidance menu M1 will be described. The display unit 5 displays a posture diagram Gp1 in a vertical plane and a posture diagram Gp2 in a horizontal plane as posture diagrams of the capsule endoscope 10 in the upper left area of the guidance menu M1. The postures of the capsule endoscope 10 displayed in the posture diagrams Gp1 and Gp2 are estimated from the condition of the magnetic field generated by the magnetic field generator 2. In the posture diagrams Gp1 and Gp2, directions in which the capsule endoscope 10 can be guided are indicated by arrows, and when an operation of any guidance direction is input, the display color of the arrow corresponding to the input guidance direction is changed to support the operation of the operator.

Figure 37:
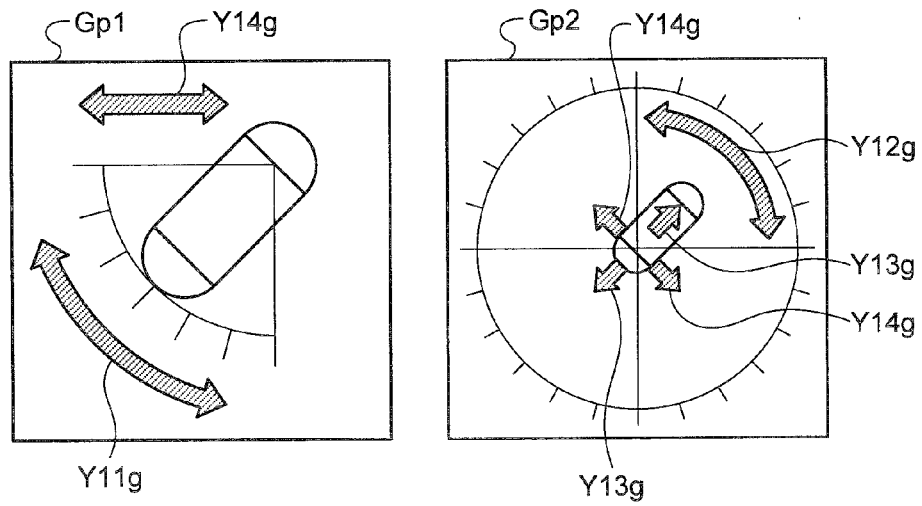
FIG. 37 is a diagram for explaining a posture diagram of the capsule endoscope shown in FIG. 36.
Figure 38:
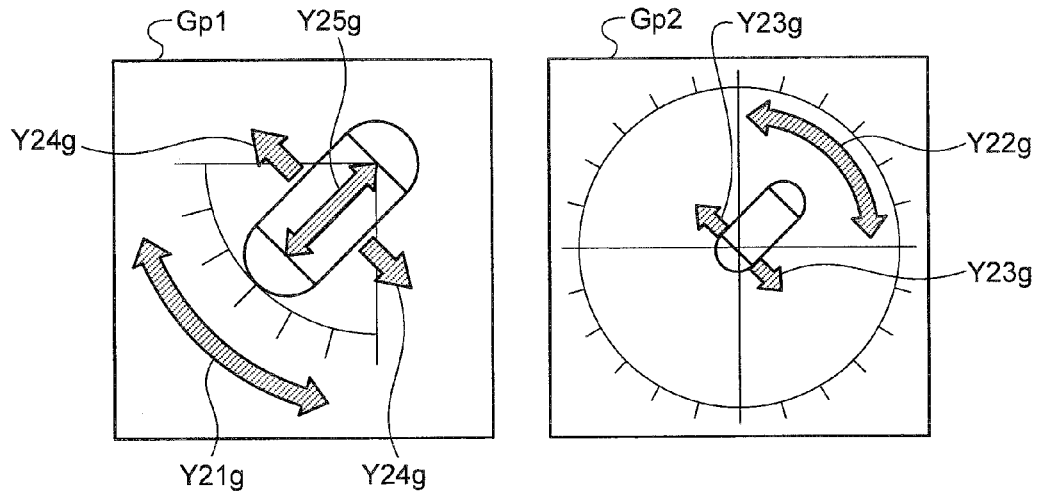
FIG. 38 is a diagram for explaining the posture diagram of the capsule endoscope shown in FIG. 36.
Figure 39:
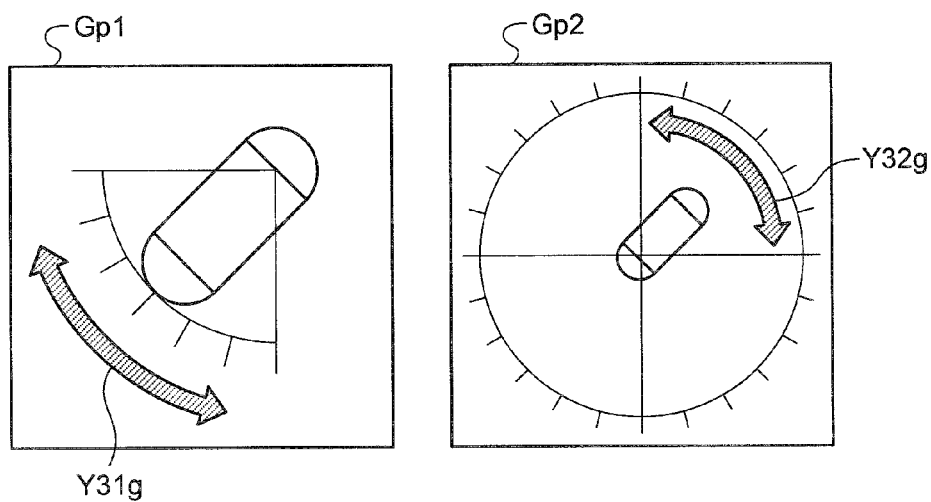
FIG. 39 is a diagram for explaining the posture diagram of the capsule endoscope shown in FIG. 36.
Figure 40:
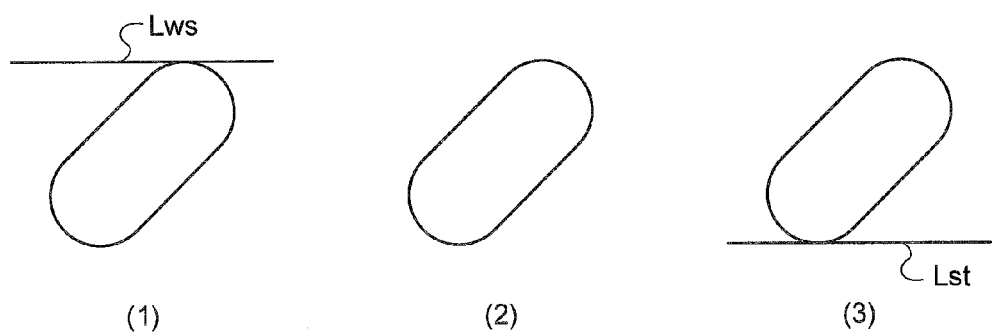
FIG. 40 is a diagram for explaining the posture diagram of the capsule endoscope shown in FIG. 36.

As described above, the directions in which the capsule endoscope 10 can be guided are different among the guidance areas, so that the arrows in the posture diagrams Gp1 and Gp2 are different among the guidance areas. For example, when the water surface area is selected as the guidance area, as illustrated in FIG. 37, an arrow Y11$g$ corresponding to the tilting operation, an arrow Y12$g$ corresponding to the rotation operation, an arrow Y13$g$ corresponding to the horizontal backward operation or the horizontal forward operation, and an arrow Y14$g$ corresponding to the horizontal right operation or the horizontal left operation are displayed in the posture diagrams Gp1 and Gp2. When the underwater area is selected as the guidance area, as illustrated in FIG. 38, an arrow Y21$g$ corresponding to the tilting operation, an arrow Y22$g$ corresponding to the rotation operation, an arrow Y23$g$ corresponding to the backward operation or the forward operation, an arrow Y24$g$ corresponding to the right operation or the left operation, and an arrow Y25$g$ corresponding to the up operation or the down operation are displayed in the posture diagrams Gp1 and Gp2. When the water bottom area is selected as the guidance area, as illustrated in FIG. 39, an arrow Y31$g$ corresponding to the tilting operation and an arrow Y32$g$ corresponding to the rotation operation are displayed in the posture diagrams Gp1 and Gp2. The operator can easily find and select operations operable in the currently selected guidance area by checking the posture diagrams Gp1 and Gp2. When the water surface area is selected as the guidance area, a line Lws indicating the water surface Ws may be displayed in the posture diagrams Gp1 and Gp2 as shown in FIG. 40 (1). When the water bottom area is selected as the guidance area, a line Lst indicating the lower stomach wall may be displayed in the posture diagrams Gp1 and Gp2 as shown in FIG. 40 (3). When the underwater area is selected as the guidance area, no line is displayed as shown in FIG. 40 (2). By displaying in this way, the operator can easily determine which area is the guidance area.

Figure 41:
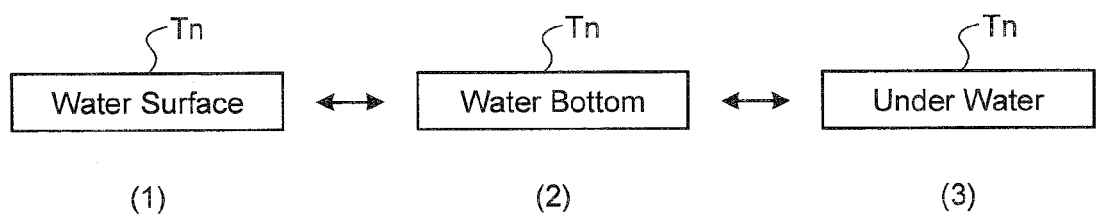
FIG. 41 is a diagram for explaining a guidance area field shown in FIG. 36.

The display unit 5 displays a guidance area field Tn, in which the currently selected guidance area is shown, in the area A12 located in the right of the area A11 in the guidance menu M1 shown in FIG. 36. In the guidance area field Tn, the display unit 5 displays words indicating the water surface area when the water surface area is selected as the guidance area as shown in FIG. 41 (1), displays words indicating the underwater area when the underwater area is selected as the guidance area as shown in FIG. 41 (2), and displays words indicating the water bottom area when the water bottom area is selected as the guidance area as shown in FIG. 41 (3). The operator can easily find the currently selected guidance area by checking the guidance area field Tn.

Figure 42:
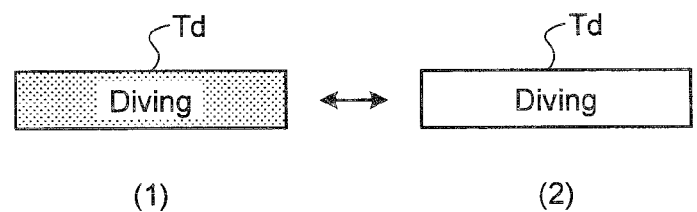
FIG. 42 is a diagram for explaining a diving mode field shown in FIG. 36.

Further, the display unit 5 displays a diving mode field Td in which the ON state or the OFF state of the diving mode is shown and an approach mode field Ta in which the ON state or the OFF state of the approach mode is shown in the area A13, which are located below the area A12 in the guidance menu M1 shown in FIG. 36 and which are described below. When the diving mode is the OFF state, the display unit 5 darkly displays the diving mode field Td as shown in FIG. 42 (1), and when the diving mode is the ON state, the display unit 5 brightly displays the diving mode field Td as shown in FIG. 42 (2). This is the same as for the approach mode field Ta.

The display unit 5 shows a magnetic field generation possible area in the horizontal plane in the area A14 below the area A11. The display unit 5 shows the peak position of the peak magnetic field in the magnetic field generation possible area in the area A14 as illustrated by the point Gc. If the water surface area is selected as the guidance area, when the peak magnetic field is generated, the capsule endoscope 10 is trapped at the peak position, so that it can be considered that the capsule endoscope 10 is located at the peak position displayed in the magnetic field generation possible area. Therefore, the operator can easily find the position in the horizontal direction of the capsule endoscope 10 by checking the peak position displayed in the area A14.

Figure 43:
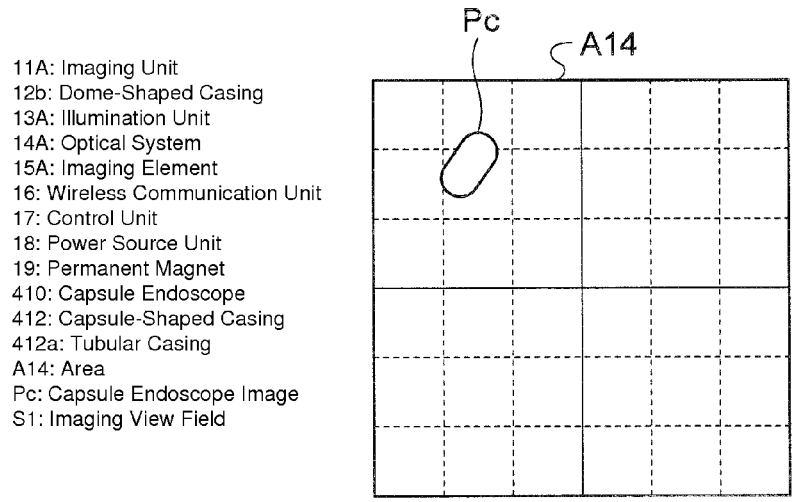
FIG. 43 is a diagram for explaining an area in which a magnetic field can be generated shown in FIG. 36.

As shown by a capsule endoscope image Pc in FIG. 43, by displaying the image of the capsule endoscope 10 when seen from the vertical direction at the peak position, the operator may find the position and the posture of the capsule endoscope 10 at the same time. The posture of the capsule endoscope 10 is estimated on the basis of the direction of the magnetic field generated by the magnetic field generator 2. When the capsule endoscope 10 is guided by the uniform gradient magnetic field, the peak position in the magnetic field generation possible area is not displayed. When the magnetic field is switched from the uniform gradient magnetic field to the peak magnetic field, the peak position is displayed again in the magnetic field generation possible area.

Next, the observation menu M2 will be described. The display unit 5 displays subject information such as patient name, patient ID, sex, and age of the subject in the upper left area A21 in the observation menu M2. The display unit 5 displays a biological image G1 captured by the imaging unit 11A in the center left of the observation menu M2 and a biological image G2 captured by the imaging unit 11B in the center right of the observation menu M2. The display unit 5 displays a marker Ts corresponding to the water surface area, a marker Tb corresponding to the underwater area, and a marker Tu corresponding to the water bottom area, between the biological images G1 and G2, and the marker of the selected guidance area is displayed brighter than the other guidance area markers that are not selected. In the example of FIG. 36, the marker Tu corresponding to the water bottom area is brightly displayed. Therefore, the operator can easily find the currently selected guidance area by checking the images G1 and G2 captured by the capsule endoscope 10 and the display status of the markers Ts, Tb, and Tu displayed near the images G1 and G2 without checking the guidance area field Tn in the guidance menu M1. The display unit 5 displays reduced images of the images captured by the pressing operation of the capture button 65 in the area A23 below the images G1 and G2 along with the times when the images are captured.

The display unit 5 displays various buttons related to operations other than the guidance operation of the capsule endoscope 10 in the area A25 below the area A21 in the observation menu M2. While the magnetic field generator 2 generates a magnetic field, in other words, while the capsule endoscope 10 is guided, only the operations related to the guidance are enabled, and inputs related to the other operations are disabled. As a result, the operator can concentrate on only the guidance operation, so that it is possible to provide a stable guidance operation environment. When the image display controller 42 receives communication data indicating that the magnetic field generator 2 generates a magnetic field from the external control unit 4, the image display controller 42 causes the buttons displayed in the area A25 not to be able to be used, in other words, to be disabled. On the other hand, when the image display controller 42 receives communication data indicating that the magnetic field generator 2 stops generating a magnetic field from the external control unit 4, the image display controller 42 causes the buttons displayed in the area A25 to be able to be used, in other words, to be enabled.

In the area A25, the display unit 5 displays, for example, a Comment button Tp1 having a function to write a comment during the examination, an Exam.List button Tp2 having a function to display a list of examination data in the past, an Adjustment button Tp3 having a function to adjust a color tone and a level of structure enhancement of the displayed image, an ENH.HIGH/LOW (HIGH/LOW of the level of structure enhancement of the displayed image) button Te (in the example of FIG. 36, a case in which the LOW level is selected is displayed), a Zoom In button Tp5 having a function to enlarge the size of the displayed image, a Zoom Out button Tp6 having a function to reduce the size of the displayed image, a Scale A button Tp7 having a function to select a type of posture information (dial gauge) displayed around the image, and a Capture button Tp8 having a function to capture the displayed image. The display unit 5 displays a reduced image of the image captured by the Capture button Tp8 in the area A23.

The display unit 5 displays an Exam.End button Te having a function to end the examination and store the examination data in an area above the area A25 in the observation menu M2. The image display controller 42 always causes the Exam.End button Te to be able to be operated, in other words, to be enabled. Therefore, it is possible to fix (store) the examination data even when the magnetic field generator 2 generates a magnetic field, in other words, when the capsule endoscope 10 is guided, or in any other situations. Based on this, even when a failure occurs in the communication with the magnetic field controller 8 and the communication cannot be restored immediately, the examination data can be protected by selecting the Exam.End button Te. The display unit 5 displays an Add Patient button Tad having a function to register patient information and start the examination in the left of the Exam.End button Te.

Figure 44:
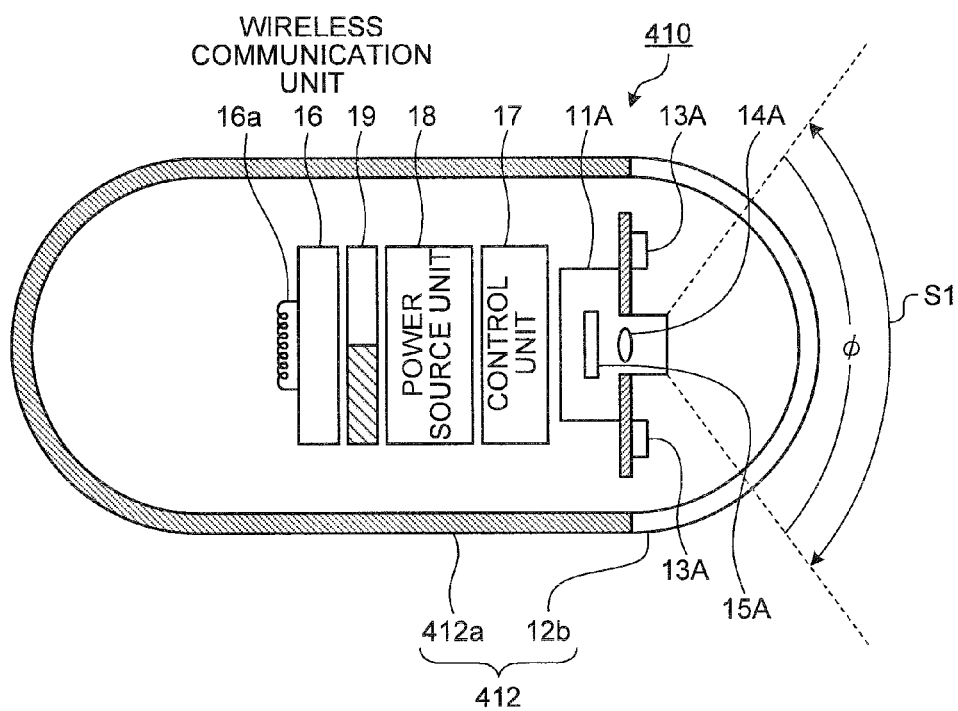
FIG. 44 is a cross-sectional schematic diagram showing another configuration example of the capsule endoscope shown in FIG. 1.

Although, in the first to the third embodiments, examples in which the capsule endoscope 10 having a plurality of imaging units is used are described, as shown in FIG. 44, a capsule endoscope 410 having a single imaging unit 11A may be used. In this case, a capsule-shaped casing 412 has a configuration in which one opening end of a tubular casing 412a is closed by the dome-shaped casing 12b.

Although, in the first to the third embodiments, the capsule endoscope 10 in which the permanent magnet 19 is used is described as an example, of course, it is not limited to this, and a capsule endoscope including an electromagnet instead of the permanent magnet 19 may be used.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical device guidance system comprising:
    a capsule medical device that includes an imaging unit that captures an image in a subject, a transmitting unit that transmits an image captured by the imaging unit to the outside, and a magnetic field response unit;
    a magnetic field generator that generates a magnetic field to the magnetic field response unit to guide the capsule medical device;
    an operation input unit for inputting operation information for magnetically guiding the capsule medical device;
    a control unit that controls the magnetic field generator to guide the capsule medical device in accordance with the operation information input by the operation input unit; and
    a storage unit that stores control content by the control unit, wherein
    the magnetic field generator selectively generates, in a space in which the capsule medical device is guided, either:
        a trapping magnetic field that is a magnetic field having, at an arbitrary peak position on a horizontal plane, a peak of magnetic field strength in a direction perpendicular to the horizontal plane, such that the trapping magnetic field attracts the magnetic field response unit to the peak position on the horizontal plane and traps the capsule medical device at the peak position, or
        a gradient magnetic field that is a magnetic field having a substantially uniform magnetic field gradient in which the distribution of magnetic field strength varies in a direction from sparse to dense, such that the gradient magnetic field forces the magnetic field response unit in the direction in which the distribution of magnetic field strength varies from sparse to dense, and
    when the control unit switches the magnetic field generated by the magnetic field generator from the trapping magnetic field to the gradient magnetic field, the control unit causes the storage unit to store a generation position on the horizontal plane of the trapping magnetic field, and when the control unit switches a magnetic field generated by the magnetic field generator from the gradient magnetic field to the trapping magnetic field, the control unit causes the magnetic field generator to generate the trapping magnetic field at the position stored in the storage unit.

2. The capsule medical device guidance system according to claim 1, wherein
    when the control unit switches a magnetic field generated by the magnetic field generator from the trapping magnetic field to the gradient magnetic field, the control unit causes the storage unit to store a magnetic field gradient in a vertical direction of the trapping magnetic field, and when the control unit switches a magnetic field generated by the magnetic field generator from the gradient magnetic field to the trapping magnetic field, the control unit causes the magnetic field generator to generate the trapping magnetic field with the magnetic field gradient in the vertical direction stored in the storage unit.

3. The capsule medical device guidance system according to claim 1, wherein
    when the control unit switches a magnetic field generated by the magnetic field generator from the trapping magnetic field to the gradient magnetic field, the control unit causes the storage unit to store a magnetic field gradient in a direction of the trapping magnetic field, and when the control unit switches a magnetic field generated by the magnetic field generator from the gradient magnetic field to the trapping magnetic field, the control unit causes the magnetic field generator to generate the trapping magnetic field with the magnetic field gradient in the direction stored in the storage unit.

4. The capsule medical device guidance system according to claim 1, further comprising:
    a receiving unit that receives the image in the subject transmitted from the capsule medical device; and
    a display unit that displays the image in the subject received by the receiving unit.

* * * * *